United States Patent
Bindschaedler et al.

(10) Patent No.: US 10,273,231 B2
(45) Date of Patent: Apr. 30, 2019

(54) AZOLINE COMPOUNDS SUBSTITUTED BY A CONDENSED RING SYSTEM

(71) Applicant: BASF SE, Ludwigshafen (DE)

(72) Inventors: Pascal Bindschaedler, Roemerberg (DE); Gopal Krishna Datta, Goettingen (DE); Wolfgang von Deyn, Neustadt (DE); Matthias Pohlman, Research Triangle Park, NC (US); Franz-Josef Braun, Durham, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/154,019

(22) Filed: Oct. 8, 2018

(65) Prior Publication Data

US 2019/0040050 A1    Feb. 7, 2019

Related U.S. Application Data

(63) Continuation of application No. 15/538,499, filed as application No. PCT/EP2015/080819 on Dec. 21, 2015, now Pat. No. 10,093,662.

(60) Provisional application No. 62/095,071, filed on Dec. 22, 2014.

(51) Int. Cl.
C07D 413/04    (2006.01)
C07D 413/14    (2006.01)
A01N 43/80    (2006.01)

(52) U.S. Cl.
CPC ........... *C07D 413/04* (2013.01); *A01N 43/80* (2013.01); *C07D 413/14* (2013.01)

(58) Field of Classification Search
None
See application file for complete search history.

(56) References Cited

U.S. PATENT DOCUMENTS

| 8,410,153 B2 * | 4/2013 | Lahm ............... C07D 261/04 514/378 |
|---|---|---|
| 2016/0145222 A1 | 5/2016 | Bindschaedler et al. |
| 2016/0145223 A1 | 5/2016 | Bindschaedler et al. |
| 2016/0355466 A1 | 12/2016 | Bindschaedler et al. |
| 2016/0366887 A1 | 12/2016 | Bindschaedler et al. |

FOREIGN PATENT DOCUMENTS

| EP | 1731512 A1 | 12/2006 |
|---|---|---|
| JP | 2007091708 A | 4/2007 |
| JP | 2008133273 A | 6/2008 |
| WO | 2008154528 A2 | 12/2008 |
| WO | 2009080250 A2 | 7/2009 |
| WO | 2010020522 A1 | 2/2010 |
| WO | 2010149506 A1 | 12/2010 |
| WO | 2011067272 A1 | 6/2011 |
| WO | 2012007426 A1 | 1/2012 |
| WO | 2012163959 A1 | 12/2012 |
| WO | 2013026929 A1 | 2/2013 |
| WO | 2016102488 A1 | 6/2016 |
| WO | 2016102490 A1 | 6/2016 |

OTHER PUBLICATIONS

International Search Report and Written Opinion for International Patent Application No. PCT/EP2015/080819, dated May 2, 2016, 8 pp.

* cited by examiner

*Primary Examiner* — Kamal A Saeed
(74) *Attorney, Agent, or Firm* — Brinks Gilson & Lione

(57) ABSTRACT

The present invention relates to compounds of formula I wherein the variables are as defined in the claims and the description. The invention further relates to the use of these compounds for controlling invertebrate pests and to plant propagation material and [o an agricultural and a veterinary composition comprising said compounds. The invention also relates to novel compounds useful as intermediate compounds in the preparation of compounds I.

19 Claims, No Drawings

AZOLINE COMPOUNDS SUBSTITUTED BY A CONDENSED RING SYSTEM

This application is a continuation of U.S. application Ser. No. 15/538,499, filed Jun. 21, 2017 (now U.S. Pat. No. 10,093,662). U.S. application Ser. No. 15/538,499 is a National Stage Application of International Application No. PCT/EP2015/080819, filed Dec. 21, 2015. U.S. application Ser. No. 15/538,499 also claims the priority benefit of U.S. Provisional Application No. 62/095,071, filed Dec. 22, 2014, the entirety of all of which are hereby incorporated herein by reference.

The present invention relates to azoline compounds substituted by a condensed ring system which are useful for combating or controlling invertebrate pests, in particular arthropod pests and nematodes. The invention also relates to a method for controlling invertebrate pests by using these compounds and to plant propagation material and to an agricultural and a veterinary composition comprising said compounds.

Invertebrate pests and in particular arthropods and nematodes destroy growing and harvested crops and attack wooden dwelling and commercial structures, causing large economic loss to the food supply and to property. While a large number of pesticidal agents are known, due to the ability of target pests to develop resistance to said agents, there is an on-going need for new agents for combating invertebrate pests, in particular insects, arachnids and nematodes.

Related compounds are described in WO 2013/026929, WO 2012/163959, WO 2012/007426, WO 2011/067272, WO 2010/149506, WO 2010/020522, WO 2009/080250, EP-A-1731512, JP-A-2007091708 and JP-A-2008133273. However, these documents do not describe compounds having the characteristic substituents and substituents' arrangement as claimed in the present invention.

It is an object of the present invention to provide compounds that have a good pesticidal activity, in particular insecticidal activity, and show a broad activity spectrum against a large number of different invertebrate pests, especially against difficult to control arthropod pests and/or nematodes.

The object of the present invention is moreover to provide compounds which are less persistent, bioaccumulative and/or toxic than the compounds of the prior art. Especially isoxazoline insecticides of the prior art show a high persistency in the soil and thus accumulate there.

It has been found that these objectives can be achieved by azoline compounds of the formula I below, by their stereoisomers, their N-oxides and by their salts, in particular their agriculturally or veterinarily acceptable salts.

Therefore, in a first aspect, the invention relates to azoline compounds of the formula I

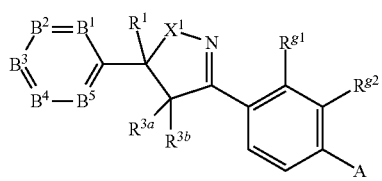

(I)

wherein
$X^1$ is O or $CH_2$;
A is a group $A^1$ or $A^2$;

wherein
$A^1$ is a group of following formula:

($A^1$)

wherein
# denotes the bond to the aromatic ring of formula (I); and
W is selected from O and S; and
$A^2$ is a group $-C(R^{7a})(R^{7b})-N(R^{52})-C(=O)-R^{62}$
$B^1$, $B^2$, $B^3$, $B^4$ and $B^5$ are independently selected from the group consisting of N and $CR^2$, with the proviso that at most one of $B^1$, $B^2$, $B^3$, $B^4$ and $B^5$ is N;
$R^{g1}$ and $R^{g2}$ form together a bridging group selected from $-CH_2CH_2O-$, $-OCH_2CH_2-$, $-CH_2OCH_2-$, $-OCH_2O-$, $-CH_2CH_2S(O)_p-$, $-S(O)_pCH_2CH_2-$, $-CH_2S(O)_pCH_2-$, $-S(O)_pCH_2S(O)_p-$, $-OCH_2S(O)_p-$, $-S(O)_pCH_2O-$, $-OCH_2CH_2CH_2-$, $-CH_2CH_2CH_2O-$, $-CH_2OCH_2CH_2-$, $-CH_2CH_2OCH_2-$, $-OCH_2CH_2O-$, $-OCH_2OCH_2-$, $-CH_2OCH_2O-$, $-S(O)_pCH_2CH_2CH_2-$, $-CH_2CH_2CH_2S(O)_p-$, $-CH_2S(O)_pCH_2CH_2-$, $-CH_2CH_2S(O)_pCH_2-$, $-S(O)_pCH_2CH_2S(O)_p-$, $-S(O)_pCH_2S(O)_pCH_2-$, $-CH_2S(O)_pCH_2S(O)_p-$, $-S(O)_pCH_2CH_2O-$, $-OCH_2CH_2S(O)_p-$, $-S(O)_pCH_2OCH_2-$, $-OCH_2S(O)_pCH_2-$, $-CH_2OCH_2S(O)_p-$ and $-CH_2S(O)_pCH_2O-$;
where p is 0, 1 or 2
where the hydrogen atoms of the above groups may be replaced by one or more substituents selected from halogen, methyl, halogenated methyl, hydroxyl, methoxy and halogenated methoxy; and/or one or two $CH_2$ groups of the above groups may be replaced by a $C=O$ group;

$R^1$ is $C_1$-haloalkyl;
each $R^2$ is independently selected from the group consisting of hydrogen, halogen, $C_1$-$C_2$-haloalkoxy and $C_1$-$C_2$-haloalkyl;
$R^{3a}$ and $R^{3b}$, independently of each other, are selected from hydrogen and halogen;
$R^{7a}$ and $R^{7b}$, independently of each other, are selected from hydrogen, cyano, methyl and $C_1$-haloalkyl;
$R^{51}$ and $R^{52}$, independently of each other, are selected from the group consisting of hydrogen, $C_1$-$C_3$-alkyl, $C_2$-$C_3$-alkenyl, $C_2$-$C_3$-alkynyl, $C_1$-$C_6$-alkoxymethyl and $CH_2$—CN;
$R^{61}$ is selected from the group consisting of hydrogen, $C_1$-$C_6$-alkyl, $C_1$-$C_6$-haloalkyl, $C_1$-$C_6$-alkyl which carries one or two radicals $R^{81}$, $C_1$-$C_6$-haloalkyl which carries one radical $R^{81}$, $C_2$-$C_6$-alkenyl, $C_2$-$C_6$-haloalkenyl, $C_2$-$C_6$-alkynyl, $C_3$-$C_6$-cycloalkyl which may be substituted by 1 or 2 CN substituents; $C_3$-$C_6$-halocycloalkyl; $-N(R^{110a})R^{101b}$, $-CH=NOR^{91}$, phenyl which may be substituted with 1, 2, 3, 4, or 5 substituents $R^{16}$, and a heterocyclic ring selected from rings E-1 to E-63

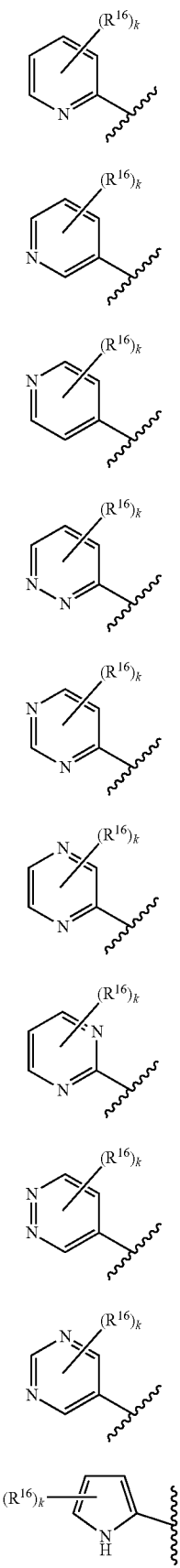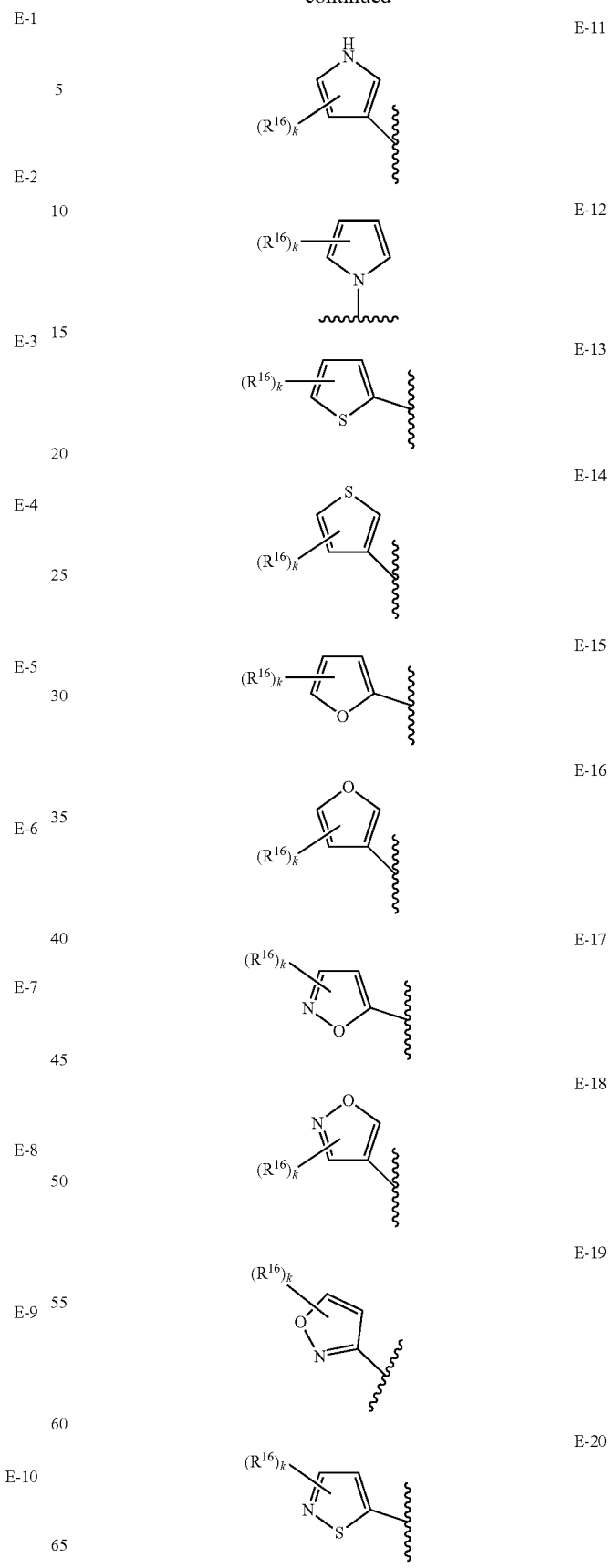

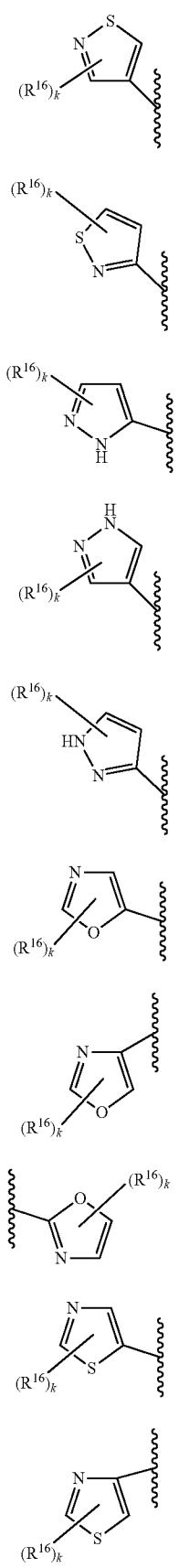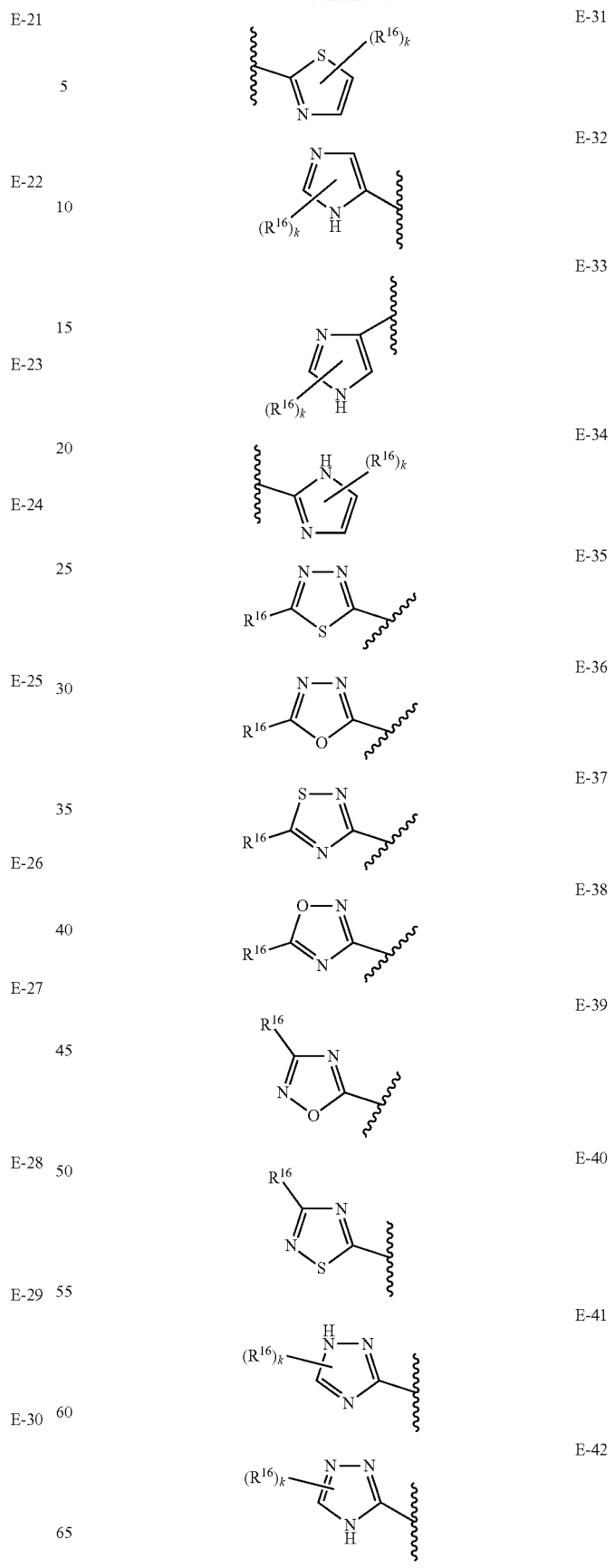

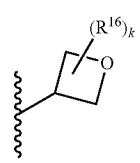 E-43
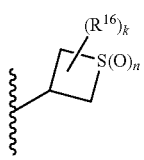 E-44
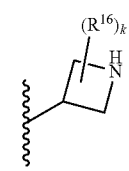 E-45
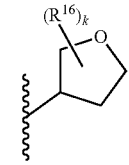 E-46
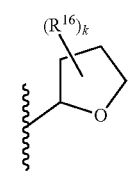 E-47
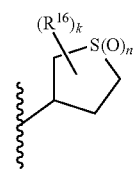 E-48
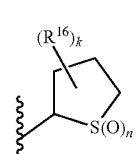 E-49
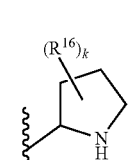 E-50
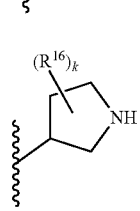 E-51
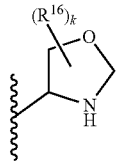 E-52
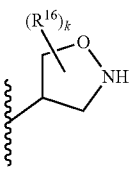 E-53
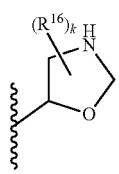 E-54
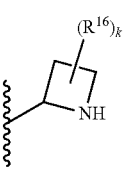 E-55
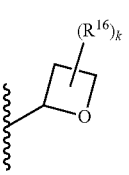 E-56
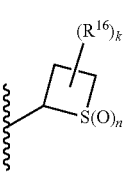 E-57
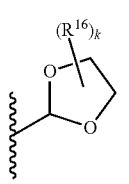 E-58
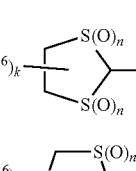 E-59
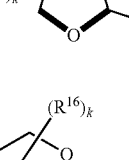 E-60
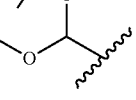 E-61

-continued

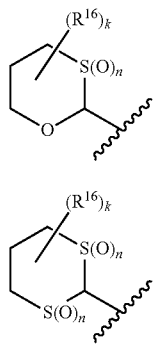

E-62

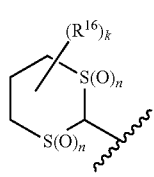

E-63 where in rings E-1 to E-63
the zigzag line denotes the attachment point to the remainder of the molecule;
k is 0, 1, 2 or 3;
n is 0, 1 or 2; and
$R^{16}$ is as defined below;
$R^{62}$ is selected from the group consisting of hydrogen, $C_1$-$C_6$-alkyl, $C_1$-$C_6$-haloalkyl, $C_1$-$C_6$-alkyl substituted by one or two radicals $R^{82}$, $C_1$-$C_6$-haloalkyl which carries one radical $R^{82}$, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl which optionally carries a CN substituent, $C_3$-$C_6$-halocycloalkyl, —N($R^{102a}$)$R^{102b}$, —C(=O)N($R^{112a}$)$R^{112b}$, —CH=NOR$^{92}$, phenyl which is optionally substituted with 1, 2, 3, 4 or 5 substituents $R^{16}$; and a heterocyclic ring selected from rings of formulae E-1 to E-63 as defined above;
each $R^{81}$ is independently selected from OH, CN, $C_3$-$C_8$-cycloalkyl which optionally carries a CN or $C_1$-haloalkyl substituent, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —C(=O)N($R^{101c}$)$R^{101d}$, phenyl, optionally substituted with 1, 2, 3, 4 or 5 substituents $R^{16}$, and a heterocyclic ring selected from rings E-1 to E-63 as defined above;
each $R^{82}$ is independently selected from OH, CN, $C_3$-$C_6$-cycloalkyl which optionally carries a CN or $C_1$-haloalkyl substituent, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —C(=O)N($R^{102c}$)$R^{102d}$, phenyl, optionally substituted with 1, 2, 3, 4 or 5 substituents $R^{16}$, and a heterocyclic ring selected from rings E-1 to E-63 as defined above;
$R^{91}$ and $R^{92}$, independently of each other, are selected from hydrogen, $C_1$-$C_6$-alkyl and $C_1$-$C_6$-haloalkyl;
$R^{101a}$, $R^{102a}$, $R^{102c}$ and $R^{112a}$, independently of each other, are selected from hydrogen and $C_1$-$C_6$-alkyl;
$R^{101b}$ is selected from hydrogen,
—C(=O)N($R^{14a}$)$R^{14b}$, phenyl, optionally substituted with 1, 2, 3, 4 or 5 substituents $R^{16}$; and a heterocyclic ring selected from rings of formulae E-1 to E-42 as defined above;
$R^{102b}$ is selected from hydrogen, $C_1$-$C_6$-alkyl, $C_1$-$C_6$-haloalkyl, $CH_2$—CN, $C_2$-$C_4$-alkenyl, $C_2$-$C_4$-alkynyl, $C_3$-$C_6$-cycloalkyl, $C_3$-$C_6$-halocycloalkyl, $C_3$-$C_6$-cycloalkylmethyl, $C_3$-$C_6$-halocycloalkylmethyl, phenyl, optionally substituted with 1, 2, 3, 4 or 5 substituents $R^{16}$;

and a heterocyclic ring selected from rings of formulae E-1 to E-42 as defined above;
$R^{101c}$ is selected from the group consisting of hydrogen, $C_1$-$C_6$-alkyl, $C_2$-$C_3$-alkynyl and $CH_2$—CN;
$R^{101d}$ is selected from the group consisting of hydrogen, $C_1$-$C_6$-alkyl, $C_2$-$C_4$-alkenyl, $C_2$-$C_4$-alkynyl, $CH_2$—CN, $C_1$-$C_6$-haloalkyl, $C_3$-$C_6$-cycloalkyl, $C_3$-$C_6$-halocycloalkyl, $C_3$-$C_6$-cycloalkylmethyl, $C_3$-$C_6$-halocycloalkylmethyl, $C_1$-$C_6$-alkoxy, $C_1$-$C_6$-haloalkoxy, phenyl which is optionally substituted with 1, 2, 3, 4 or 5 substituents selected from the group consisting of halogen, cyano, nitro, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio and $C_1$-$C_4$-haloalkylthio; and a heterocyclic ring selected from rings of formulae E-1 to E-63 as defined above;
$R^{102d}$ and $R^{112b}$, independently of each other, are selected from hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl which optionally carries a CN substituent, $C_3$-$C_6$-halocycloalkyl, $C_3$-$C_6$-cycloalkylmethyl and $C_3$-$C_6$-halocycloalkylmethyl;
$R^{14a}$ is selected from the group consisting of hydrogen and $C_1$-$C_6$-alkyl;
$R^{14b}$ is selected from the group consisting of hydrogen, $C_1$-$C_6$-alkyl, $C_2$-$C_4$-alkenyl, $C_2$-$C_4$-alkynyl, $CH_2$—CN, $C_1$-$C_6$-haloalkyl, $C_3$-$C_6$-cycloalkyl, $C_3$-$C_6$-halocycloalkyl, $C_3$-$C_6$-cycloalkylmethyl, $C_1$-$C_4$-alkoxy and $C_1$-$C_4$-haloalkoxy; and
each $R^{16}$ is independently selected from the group consisting of halogen, cyano, nitro, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_3$-$C_6$-cycloalkyl-$C_1$-$C_4$-alkyl, $C_3$-$C_6$-halocycloalkyl-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)aminocarbonyl; or
two $R^{16}$ present on the same carbon atom of a saturated ring may form together =O or =S; or
two $R^{16}$ present on the same S or SO ring member of a heterocyclic ring may together form a group =N($C_1$-$C_6$-alkyl), =NO($C_1$-$C_6$-alkyl), =NN(H)($C_1$-$C_6$-alkyl) or =NN($C_1$-$C_6$-alkyl)$_2$;
and the N-oxides, stereoisomers and agriculturally or veterinarily acceptable salts thereof.

The present invention also provides an agricultural composition comprising at least one compound of the formula I as defined herein, a stereoisomer thereof and/or at least one agriculturally acceptable salt thereof and at least one inert liquid and/or solid agriculturally acceptable carrier.

The present invention also provides a veterinary composition comprising at least one compound of the formula I as defined herein, a stereoisomer thereof and/or at least one veterinarily acceptable salt thereof and at least one inert liquid and/or solid veterinarily acceptable carrier.

The present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of formula I, a stereoisomer thereof and/or at least one agriculturally acceptable salt thereof as defined herein. In a specific embodiment, the method is not for treating the human or animal body; i.e. the food supply, habitat, breeding ground, area, material, environment, soils, surfaces or spaces is not a human or animal body.

The method serves in particular for protecting plants from attack or infestation by invertebrate pests, and thus comprises treating the plants with a pesticidally effective amount of at least one compound of the formula I as defined above, a stereoisomer thereof and/or at least one agriculturally acceptable salt thereof. The method further serves in particular for protecting plant propagation material and/or the plants which grow therefrom from attack or infestation by invertebrate pests, and thus comprises treating the plant propagation material with a pesticidally effective amount of at least one compound of the formula I as defined above, a stereoisomer thereof and/or at least one agriculturally acceptable salt thereof.

The present invention also relates to plant propagation material, in particular seed, comprising at least one compound of formula I, a stereoisomer thereof and/or at least one agriculturally acceptable salt thereof as defined herein.

The present invention further relates to a method for treating or protecting an animal from infestation or infection by parasites (invertebrate pests) which comprises bringing the animal in contact with a parasiticidally/pesticidally effective amount of a compound of the formula I, a stereoisomer thereof and/or at least one veterinarily acceptable salt thereof as defined herein. Bringing the animal in contact with the compound I, its salt or the veterinary composition of the invention means applying or administering it to the animal.

The present invention further relates to compounds of the formula I, stereoisomers thereof and/or veterinarily acceptable salts thereof as defined herein for use as a medicament, especially for use as a medicament for treating or protecting an animal from infestation or infection by parasites (invertebrate pests).

The term "steroisomers" encompasses both optical isomers, such as enantiomers or diastereomers, the latter existing due to more than one center of chirality in the molecule, as well as geometrical isomers (cis/trans isomers).

Depending on the substitution pattern, the compounds of the formula I may have one or more centers of chirality, in which case they are present as mixtures of enantiomers or diastereomers. One center of chirality is the carbon ring atom of the isoxazoline or pyrroline ring carrying radical $R^1$. The invention provides both the pure enantiomers or diastereomers and their mixtures and the use according to the invention of the pure enantiomers or diastereomers of the compound I or its mixtures. Suitable compounds of the formula I also include all possible geometrical stereoisomers (cis/trans isomers) and mixtures thereof.

In a specific embodiment, the compounds I are present in form of a mixture of compounds I.1 and I.2

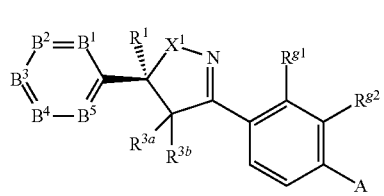

(I.1)

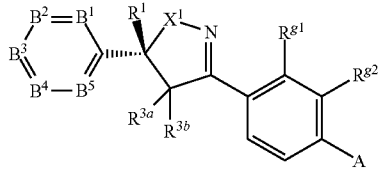

(I.2)

where compound I.1 is present in an amount of more than 50% by weight, in particular of at least 70% by weight, specifically of at least 90% by weight, based on the total weight of compounds I.1 and I.2.

The term N-oxides relates to a form of compounds I in which at least one nitrogen atom is present in oxidized form (as NO). To be more precise, it relates to any compound of the present invention which has at least one tertiary nitrogen atom that is oxidized to an N-oxide moiety. N-oxides of compounds I can in particular be prepared by oxidizing e.g. the ring nitrogen atom of the isoxazoline/pyrroline moiety and/or of any nitrogen-containing heterocyclic group present in group A with a suitable oxidizing agent, such as peroxo carboxylic acids or other peroxides. The person skilled in the art knows if and in which positions compounds of the present invention may form N-oxides.

The compounds of the present invention may be amorphous or may exist in one ore more different crystalline states (polymorphs) which may have a different macroscopic properties such as stability or show different biological properties such as activities. The present invention includes both amorphous and crystalline compounds of the formula I, mixtures of different crystalline states of the respective compound I, as well as amorphous or crystalline salts thereof.

Salts of the compounds of the formula I are preferably agriculturally and veterinarily acceptable salts. They can be formed in a customary method, e.g. by reacting the compound with an acid of the anion in question if the compound of formula I has a basic functionality or by reacting an acidic compound of formula I with a suitable base.

Suitable agriculturally acceptable salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH^{4+}$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy) ethylammonium, bis(2-hydroxyethyl)ammonium, benzyltrimethylammonium and benzyl-triethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formulae I with an acid of the corresponding anion, preferably of hydrochloric acid, hydrobromic acid, sulfuric acid, phosphoric acid or nitric acid.

By the term "veterinarily acceptable salts" is meant salts of those cations or anions which are known and accepted in the art for the formation of salts for veterinary use. Suitable acid addition salts, e.g. formed by compounds of formula I containing a basic nitrogen atom, e.g. an amino group, include salts with inorganic acids, for example hydrochlorids, sulphates, phosphates, and nitrates and salts of organic acids for example acetic acid, maleic acid, dimaleic acid, fumaric acid, difumaric acid, methane sulfenic acid, methane sulfonic acid, and succinic acid.

The term "invertebrate pest" as used herein encompasses animal populations, such as insects, arachnids and nematodes, which may attack plants, thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. The plant propagation materials may be treated prophylactically with a plant protection compound either at or before planting or transplanting. Said young plants may also be protected before transplantation by a total or partial treatment by immersion or pouring.

The term "plants" comprises any types of plants including "non-cultivated plants" and in particular "cultivated plants".

The term "non-cultivated plants" refers to any wild type species or related species or related genera of a cultivated plant.

The term "cultivated plants" is to be understood as including plants which have been modified by breeding, mutagenesis or genetic engineering including but not limiting to agricultural biotech products on the market or in development (cf. http://www.bio.org/speeches/pubs/er/agri_products.asp). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e. g. by glycosylation or polymer additions such as prenylated, acetylated or farnesylated moieties or PEG moieties.

Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxyl-phenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

The term "alkyl" as used herein and in the alkyl moieties of alkoxy, alkylthio, alkylsulfinyl, alkylsulfonyl, alkylcarbonyl and the like refers to saturated straight-chain or branched hydrocarbon radicals having 1 to 2 ("$C_1$-$C_2$-alkyl"), 1 to 3 ("$C_1$-$C_3$-alkyl"), 1 to 4 ("$C_1$-$C_4$-alkyl"), 2 to 4 ("$C_2$-$C_4$-alkyl"), 1 to 6 ("$C_1$-$C_6$-alkyl"), 1 to 8 ("$C_1$-$C_8$-alkyl") or 1 to 10 ("$C_1$-$C_{10}$-alkyl") carbon atoms. $C_1$-$C_2$-Alkyl is methyl or ethyl. $C_1$-$C_3$-Alkyl is additionally propyl and isopropyl. $C_1$-$C_4$-Alkyl is additionally butyl, 1-methylpropyl (sec-butyl), 2-methylpropyl (isobutyl) or 1,1-dimethylethyl (tert-butyl). $C_1$-$C_6$-Alkyl is additionally also, for example, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl. $C_1$-$C_8$-Alkyl is additionally also, for example, heptyl, octyl, 2-ethylhexyl and positional isomers thereof. $C_1$-$C_{10}$-Alkyl is additionally also, for example, nonyl, decyl and positional isomers thereof. $C_2$-$C_4$-Alkyl is ethyl, propyl, isopropyl, n-butyl, 1-methylpropyl (sec-butyl), 2-methylpropyl (isobutyl) or 1,1-dimethylethyl (tert-butyl).

The term "haloalkyl" as used herein, which is also expressed as "alkyl which is partially or fully halogenated", refers to straight-chain or branched alkyl groups having 1 ("$C_1$-haloalkyl"; also termed "halogenated methyl" or "halomethyl"), 1 to 2 ("$C_1$-$C_2$-haloalkyl"), 1 to 3 ("$C_1$-$C_3$-haloalkyl"), 1 to 4 ("$C_1$-$C_4$-haloalkyl"), 1 to 6 ("$C_1$-$C_6$-haloalkyl"), 1 to 8 ("$C_1$-$C_8$-haloalkyl") or 1 to 10 ("$C_1$-$C_{10}$-haloalkyl") carbon atoms (as mentioned above), where some or all of the hydrogen atoms in these groups are replaced by halogen atoms as mentioned above: $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl. $C_1$-$C_3$-haloalkyl is additionally, for example, 1-fluoropropyl, 2-fluoropropyl, 3-fluoropropyl, 1,1-difluoropropyl, 2,2-difluoropropyl, 1,2-difluoropropyl, 3,3-difluoropropyl, 3,3,3-trifluoropropyl, heptafluoropropyl, 1,1,1-trifluoroprop-2-yl, 3-chloropropyl and the like. Examples for $C_1$-$C_4$-haloalkyl are, apart those mentioned for $C_1$-$C_3$-haloalkyl, 4-chlorobutyl and the like.

"Halomethyl" or "halogenated methyl" or "$C_1$-haloalkyl" is methyl in which 1, 2 or 3 of the hydrogen atoms are replaced by halogen atoms. Examples are bromomethyl, chloromethyl, fluoromethyl, dichloromethyl, trichloromethyl, difluoromethyl, trifluoromethyl, chlorofluoromethyl, dichlorofluoromethyl, chlorodifluoromethyl and the like.

$C_2$-$C_4$-Alkyl substituted with 1 or 2 fluorine atoms is $C_2$-$C_4$-alkyl, where 1 or 2 of the hydrogen atoms are replaced by fluorine atoms. Examples are 1-fluoroethyl, 2-fluoroethyl, 1,1-difluoroethyl, 1,2-difluoroethyl, 2,2-difluoroethyl, 1-fluoropropyl, 2-fluoropropyl, 3-fluoropropyl, 1,1-difluoropropyl, 2,2-difluoropropyl, 3,3-difluoropropyl, 1,2-difluoropropyl, 1,3-difluoropropyl, 2,3-difluoropropyl, 1-fluorobutyl, 2-fluorobutyl, 3-fluorobutyl, 4-fluorobutyl, and the like.

The term "alkenyl" as used herein refers to monounsaturated straight-chain or branched hydrocarbon radicals having 2 to 3 ("$C_2$-$C_3$-alkenyl"), 2 to 4 ("$C_2$-$C_4$-alkenyl"), 2 to 6 ("$C_2$-$C_6$-alkenyl"), 2 to 8 ("$C_2$-$C_8$-alkenyl") or 2 to 10 ("$C_2$-$C_{10}$-alkenyl") carbon atoms and a double bond in any position, for example $C_2$-$C_3$-alkenyl, such as ethenyl, 1-propenyl, 2-propenyl or 1-methylethenyl; $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl; $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like, or $C_2$-$C_{10}$-alkenyl, such as the radicals mentioned for $C_2$-$C_6$-alkenyl and additionally 1-heptenyl, 2-heptenyl, 3-heptenyl, 1-octenyl, 2-octenyl, 3-octenyl, 4-octenyl, 1-nonenyl, 2-nonenyl, 3-nonenyl, 4-nonenyl, 1-decenyl, 2-decenyl, 3-decenyl, 4-decenyl, 5-decenyl and the positional isomers thereof.

The term "haloalkenyl" as used herein, which is also expressed as "alkenyl which is partially or fully halogenated", refers to unsaturated straight-chain or branched hydrocarbon radicals having 2 to 3 ("$C_2$-$C_3$-haloalkenyl"), 2 to 4 ("$C_2$-$C_4$-haloalkenyl"), 2 to 6 ("$C_2$-$C_6$-haloalkenyl"), 2 to 8 ("$C_2$-$C_8$-haloalkenyl") or 2 to 10 ("$C_2$-$C_{10}$-haloalkenyl") carbon atoms and a double bond in any position (as mentioned above), where some or all of the hydrogen atoms in these groups are replaced by halogen atoms as mentioned above, in particular fluorine, chlorine and bromine, for example chlorovinyl, chloroallyl and the like.

The term "alkynyl" as used herein refers to straight-chain or branched hydrocarbon groups having 2 to 3 ("$C_2$-$C_3$-alkynyl"), 2 to 4 ("$C_2$-$C_4$-alkynyl"), 2 to 6 ("$C_2$-$C_6$-alkynyl"), 2 to 8 ("$C_2$-$C_8$-alkynyl"), or 2 to 10 ("$C_2$-$C_{10}$-alkynyl") carbon atoms and one or two triple bonds in any position, for example $C_2$-$C_3$-alkynyl, such as ethynyl, 1-propynyl or 2-propynyl; $C_2$-$C_4$-alkynyl, such as ethynyl, 1-propynyl, 2-propynyl, 1-butynyl, 2-butynyl, 3-butynyl, 1-methyl-2-propynyl and the like, $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like;

The term "haloalkynyl" as used herein, which is also expressed as "alkynyl which is partially or fully halogenated", refers to unsaturated straight-chain or branched hydrocarbon radicals having 2 to 3 ("$C_2$-$C_3$-haloalkynyl"), 2 to 4 ("$C_2$-$C_4$-haloalkynyl"), 3 to 4 ("$C_3$-$C_4$-haloalkynyl"), 2 to 6 ("$C_2$-$C_6$-haloalkynyl"), 2 to 8 ("$C_2$-$C_8$-haloalkynyl") or 2 to 10 ("$C_2$-$C_{10}$-haloalkynyl") carbon atoms and one or two triple bonds in any position (as mentioned above), where some or all of the hydrogen atoms in these groups are replaced by halogen atoms as mentioned above, in particular fluorine, chlorine and bromine;

The term "cycloalkyl" as used herein refers to mono- or bi- or polycyclic saturated hydrocarbon radicals having 3 to 8 ("$C_3$-$C_8$-cycloalkyl"), in particular 3 to 6 ("$C_3$-$C_6$-cycloalkyl") or 3 to 5 ("$C_3$-$C_5$-cycloalkyl") or 3 to 4 ("$C_3$-$C_4$-cycloalkyl") carbon atoms. Examples of monocyclic radicals having 3 to 4 carbon atoms comprise cyclopropyl and cyclobutyl. Examples of monocyclic radicals having 3 to 5 carbon atoms comprise cyclopropyl, cyclobutyl and cyclopentyl. Examples of monocyclic radicals having 3 to 6 carbon atoms comprise cyclopropyl, cyclobutyl, cyclopentyl and cyclohexyl. Examples of monocyclic radicals having 3 to 8 carbon atoms comprise cyclopropyl, cyclobutyl, cyclopentyl, cyclohexyl, cycloheptyl and cyclooctyl. Examples of bicyclic radicals having 7 or 8 carbon atoms comprise bicyclo[2.2.1]heptyl, bicyclo[3.1.1]heptyl, bicyclo[2.2.2]octyl and bicyclo[3.2.1]octyl. Preferably, the term cycloalkyl denotes a monocyclic saturated hydrocarbon radical.

The term "halocycloalkyl" as used herein, which is also expressed as "cycloalkyl which is partially or fully halogenated", refers to mono- or bi- or polycyclic saturated hydrocarbon groups having 3 to 8 ("$C_3$-$C_8$-halocycloalkyl") or preferably 3 to 6 ("$C_3$-$C_6$-halocycloalkyl") or 3 to 5 ("$C_3$-$C_5$-halocycloalkyl") or 3 to 4 ("$C_3$-$C_4$-halocycloalkyl") carbon ring members (as mentioned above) in which some or all of the hydrogen atoms are replaced by halogen atoms as mentioned above, in particular fluorine, chlorine and bromine.

The term "cycloalkyl-$C_1$-$C_4$-alkyl" refers to a $C_3$-$C_8$-cycloalkyl group ("$C_3$-$C_8$-cycloalkyl-$C_1$-$C_4$-alkyl"), preferably a $C_3$-$C_6$-cycloalkyl group ("$C_3$-$C_6$-cycloalkyl-$C_1$-$C_4$-alkyl"), more preferably a $C_3$-$C_4$-cycloalkyl group ("$C_3$-$C_4$-cycloalkyl-$C_1$-$C_4$-alkyl") as defined above (preferably a monocyclic cycloalkyl group) which is bound to the remainder of the molecule via a $C_1$-$C_4$-alkyl group, as defined above. Examples for $C_3$-$C_4$-cycloalkyl-$C_1$-$C_4$-alkyl are cyclopropylmethyl, cyclopropylethyl, cyclopropylpropyl, cyclobutylmethyl, cyclobutylethyl and cyclobutylpropyl, Examples for $C_3$-$C_6$-cycloalkyl-$C_1$-$C_4$-alkyl, apart those mentioned for $C_3$-$C_4$-cycloalkyl-$C_1$-$C_4$-alkyl, are cyclopentylmethyl, cyclopentylethyl, cyclopentylpropyl, cyclohexylmethyl, cyclohexylethyl and cyclohexylpropyl. Examples for $C_3$-$C_8$-cycloalkyl-$C_1$-$C_4$-alkyl, apart those mentioned for $C_3$-$C_6$-cycloalkyl-$C_1$-$C_4$-alkyl, are cycloheptylmethyl, cycloheptylethyl, cyclooctylmethyl and the like.

The term "$C_3$-$C_6$-cycloalkyl-methyl" refers to a $C_3$-$C_6$-cycloalkyl group as defined above which is bound to the remainder of the molecule via a methylene group ($CH_2$). Examples are cyclopropylmethyl, cyclobutylmethyl, cyclopentylmethyl and cyclohexylmethyl.

The term "$C_3$-$C_8$-halocycloalkyl-$C_1$-$C_4$-alkyl" refers to a $C_3$-$C_8$-halocycloalkyl group as defined above which is bound to the remainder of the molecule via a $C_1$-$C_4$-alkyl group, as defined above.

The term "$C_3$-$C_6$-halocycloalkyl-methyl" refers to a $C_3$-$C_6$-halocycloalkyl group as defined above which is bound to the remainder of the molecule via a methylene group ($CH_2$).

The term "$C_1$-$C_2$-alkoxy" is a $C_1$-$C_2$-alkyl group, as defined above, attached via an oxygen atom. The term "$C_1$-$C_3$-alkoxy" is a $C_1$-$C_3$-alkyl group, as defined above, attached via an oxygen atom. The term "$C_1$-$C_4$-alkoxy" is a $C_1$-$C_4$-alkyl group, as defined above, attached via an oxygen atom. The term "$C_1$-$C_6$-alkoxy" is a $C_1$-$C_6$-alkyl group, as defined above, attached via an oxygen atom. The term "$C_1$-$C_{10}$-alkoxy" is a $C_1$-$C_{10}$-alkyl group, as defined above, attached via an oxygen atom. $C_1$-$C_2$-Alkoxy is methoxy or ethoxy. $C_1$-$C_3$-Alkoxy is additionally, for example, n-propoxy and 1-methylethoxy (isopropoxy). $C_1$-$C_4$-Alkoxy is additionally, for example, butoxy, 1-methylpropoxy (sec-butoxy), 2-methylpropoxy (isobutoxy) or 1,1-dimethylethoxy (tert-butoxy). $C_1$-$C_6$-Alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. $C_1$-$C_8$-Alkoxy is additionally, for example, heptyloxy, octyloxy, 2-ethylhexyloxy and positional isomers thereof. $C_1$-$C_{10}$-Alkoxy is additionally, for example, nonyloxy, decyloxy and positional isomers thereof.

The term "$C_1$-$C_2$-haloalkoxy" is a $C_1$-$C_2$-haloalkyl group, as defined above, attached via an oxygen atom. The term "$C_1$-$C_3$-haloalkoxy" is a $C_1$-$C_3$-haloalkyl group, as defined above, attached via an oxygen atom. The term "$C_1$-$C_4$-haloalkoxy" is a $C_1$-$C_4$-haloalkyl group, as defined above, attached via an oxygen atom. The term "$C_1$-$C_6$-haloalkoxy" is a $C_1$-$C_6$-haloalkyl group, as defined above, attached via an oxygen atom. The term "$C_1$-$C_{10}$-haloalkoxy" is a $C_1$-$C_{10}$-haloalkyl group, as defined above, attached via an oxygen atom. $C_1$-$C_2$-Haloalkoxy is, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_3$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy or 1-($CH_2Br$)-2-bromoethoxy. $C_1$-$C_4$-Haloalkoxy is additionally, for example, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-brompentoxy, 5-iodopentoxy, undecafluoropentoxy, 6-fluorohexoxy, 6-chlorohexoxy, 6-bromohexoxy, 6-iodohexoxy or dodecafluorohexoxy.

The term "halogenated methoxy" relates to a $C_1$-haloalkyl group, as defined above, attached via an oxygen atom. Examples are $OCH_2F$, $OCHF_2$, $OCF_3$, $OCH_2Cl$, $OCHCl_2$, $OCCl_3$, chlorofluoromethoxy, dichlorofluoromethoxy or chlorodifluoromethoxy.

The term "$C_1$-$C_3$-alkoxy-$C_1$-$C_3$-alkyl" as used herein, refers to a straight-chain or branched alkyl group having 1 to 3 carbon atoms, as defined above, where one hydrogen atom is replaced by a $C_1$-$C_3$-alkoxy group, as defined above. The term "$C_1$-$C_4$-alkoxy-$C_1$-$C_4$-alkyl" as used herein, refers to a straight-chain or branched alkyl group having 1 to 4 carbon atoms, as defined above, where one hydrogen atom is replaced by a $C_1$-$C_4$-alkoxy group, as defined above. The term "$C_1$-$C_6$-alkoxy-$C_1$-$C_6$-alkyl" as used herein, refers to a straight-chain or branched alkyl group having 1 to 6 carbon atoms, as defined above, where one hydrogen atom is replaced by a $C_1$-$C_6$-alkoxy group, as defined above. Examples are methoxymethyl, ethoxymethyl, propoxymethyl, isopropoxymethyl, n-butoxymethyl, sec-butoxymethyl, isobutoxymethyl, tert-butoxymethyl, 1-methoxyethyl, 1-ethoxyethyl, 1-propoxyethyl, 1-isopropoxyethyl, 1-n-butoxyethyl, 1-sec-butoxyethyl, 1-isobutoxyethyl, 1-tert-butoxyethyl, 2-methoxyethyl, 2-ethoxyethyl, 2-propoxyethyl, 2-isopropoxyethyl, 2-n-butoxyethyl, 2-sec-butoxyethyl, 2-isobutoxyethyl, 2-tert-butoxyethyl, 1-methoxypropyl, 1-ethoxypropyl, 1-propoxypropyl, 1-isopropoxypropyl, 1-n-butoxypropyl, 1-sec-butoxypropyl, 1-isobutoxypropyl, 1-tert-butoxypropyl, 2-methoxypropyl, 2-ethoxypropyl, 2-propoxypropyl, 2-isopropoxypropyl, 2-n-butoxypropyl, 2-sec-butoxypropyl, 2-isobutoxypropyl, 2-tert-butoxypropyl, 3-methoxypropyl, 3-ethoxypropyl, 3-propoxypropyl, 3-isopropoxypropyl, 3-n-butoxypropyl, 3-sec-butoxypropyl, 3-isobutoxypropyl, 3-tert-butoxypropyl and the like.

The term "$C_1$-$C_4$-alkoxy-methyl" as used herein, refers to methyl in which one hydrogen atom is replaced by a $C_1$-$C_4$-alkoxy group, as defined above. The term "$C_1$-$C_6$-alkoxy-methyl" as used herein, refers to methyl in which one hydrogen atom is replaced by a $C_1$-$C_6$-alkoxy group, as defined above. Examples are methoxymethyl, ethoxymethyl, propoxymethyl, isopropoxymethyl, n-butoxymethyl, sec-butoxymethyl, isobutoxymethyl, tert-butoxymethyl, pentyloxymethyl, hexyloxymethyl and the like.

$C_1$-$C_6$-Haloalkoxy-$C_1$-$C_6$-alkyl is a straight-chain or branched alkyl group having from 1 to 6, especially 1 to 4 carbon atoms (=$C_1$-$C_6$-haloalkoxy-$C_1$-$C_4$-alkyl), wherein one of the hydrogen atoms is replaced by a $C_1$-$C_6$-alkoxy group and wherein at least one, e.g. 1, 2, 3, 4 or all of the remaining hydrogen atoms (either in the alkoxy moiety or in the alkyl moiety or in both) are replaced by halogen atoms. $C_1$-$C_4$-Haloalkoxy-$C_1$-$C_4$-alkyl is a straight-chain or branched alkyl group having from 1 to 4 carbon atoms, wherein one of the hydrogen atoms is replaced by a $C_1$-$C_4$-alkoxy group and wherein at least one, e.g. 1, 2, 3, 4 or all of the remaining hydrogen atoms (either in the alkoxy moiety or in the alkyl moiety or in both) are replaced by halogen atoms. Examples are difluoromethoxymethyl ($CHF_2OCH_2$), trifluoromethoxymethyl, 1-difluoromethoxyethyl, 1-trifluoromethoxyethyl, 2-difluoromethoxyethyl, 2-trifluoromethoxyethyl, difluoro-methoxy-methyl ($CH_3OCF_2$), 1,1-difluoro-2-methoxyethyl, 2,2-difluoro-2-methoxyethyl and the like.

The term "$C_1$-$C_2$-alkylthio" is a $C_1$-$C_2$-alkyl group, as defined above, attached via a sulfur atom. The term "$C_1$-$C_3$-alkylthio" is a $C_1$-$C_3$-alkyl group, as defined above, attached via a sulfur atom. The term "$C_1$-$C_4$-alkylthio" is a $C_1$-$C_4$-alkyl group, as defined above, attached via a sulfur atom. The term "$C_1$-$C_6$-alkylthio" is a $C_1$-$C_6$-alkyl group, as defined above, attached via a sulfur atom. The term "$C_1$-$C_{10}$-alkylthio" is a $C_1$-$C_{10}$-alkyl group, as defined above, attached via a sulfur atom. $C_1$-$C_2$-Alkylthio is methylthio or ethylthio. $C_1$-$C_3$-Alkylthio is additionally, for example, n-propylthio or 1-methylethylthio (isopropylthio). $C_1$-$C_4$-Alkylthio is additionally, for example, butylthio, 1-methylpropylthio (sec-butylthio), 2-methylpropylthio (isobutylthio) or 1,1-dimethylethylthio (tert-butylthio). $C_1$-$C_6$-Alkylthio is additionally, for example, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio. $C_1$-$C_8$-Alkylthio is additionally, for example, heptylthio, octylthio, 2-ethylhexylthio and positional isomers thereof. $C_1$-$C_{10}$-Alkylthio is additionally, for example, nonylthio, decylthio and positional isomers thereof.

The term "$C_1$-$C_2$-haloalkylthio" is a $C_1$-$C_2$-haloalkyl group, as defined above, attached via a sulfur atom. The term "$C_1$-$C_3$-haloalkylthio" is a $C_1$-$C_3$-haloalkyl group, as defined above, attached via a sulfur atom. The term "$C_1$-$C_4$-haloalkylthio" is a $C_1$-$C_4$-haloalkyl group, as defined above, attached via a sulfur atom. The term "$C_1$-$C_6$-haloalkylthio" is a $C_1$-$C_6$-haloalkyl group, as defined above, attached via a sulfur atom. The term "$C_1$-$C_{10}$-haloalkylthio" is a $C_1$-$C_{10}$-haloalkyl group, as defined above, attached via a sulfur atom. $C_1$-$C_2$-Haloalkylthio is, for example, $SCH_2F$, $SCHF_2$, $SCF_3$, $SCH_2Cl$, $SCHCl_2$, $SCCl_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or $SC_2F_5$. $C_1$-$C_3$-Haloalkylthio is additionally, for example, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio or 1-($CH_2Br$)-2-bromoethylthio. $C_1$-$C_4$-Haloalkylthio is additionally, for example, 4-fluorobutylthio, 4-chlorobutylthio, 4-bromobutylthio or nonafluorobutylthio. $C_1$-$C_6$-Haloalkylthio is additionally, for example, 5-fluoropentylthio, 5-chloropentylthio, 5-brompentylthio, 5-iodopentylthio, undecafluoropentylthio, 6-fluorohexylthio, 6-chlorohexylthio, 6-bromohexylthio, 6-iodohexylthio or dodecafluorohexylthio.

The term "$C_1$-$C_2$-alkylsulfinyl" is a $C_1$-$C_2$-alkyl group, as defined above, attached via a sulfinyl [S(O)] group. The term "$C_1$-$C_4$-alkylsulfinyl" is a $C_1$-$C_4$-alkyl group, as defined above, attached via a sulfinyl [S(O)] group. The term "$C_1$-$C_6$-alkylsulfinyl" is a $C_1$-$C_6$-alkyl group, as defined above, attached via a sulfinyl [S(O)] group. The term "$C_1$-$C_{10}$-alkylsulfinyl" is a $C_1$-$C_{10}$-alkyl group, as defined above, attached via a sulfinyl [S(O)] group. $C_1$-$C_2$-Alkylsulfinyl is methylsulfinyl or ethylsulfinyl. $C_1$-$C_4$-Alkylsulfinyl is additionally, for example, n-propylsulfinyl, 1-methylethylsulfinyl (isopropylsulfinyl), butylsulfinyl, 1-methylpropylsulfinyl (sec-butylsulfinyl), 2-methylpropylsulfinyl (isobutylsulfinyl) or 1,1-dimethylethylsulfinyl (tert-butylsulfinyl). $C_1$-$C_6$-Alkylsulfinyl is additionally, for example, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl. $C_1$-$C_8$-Alkylsulfinyl is additionally, for example, heptylsulfinyl, octylsulfinyl, 2-ethylhexylsulfinyl and positional isomers thereof. $C_1$-$C_{10}$-Alkylsulfinyl is additionally, for example, nonylsulfinyl, decylsulfinyl and positional isomers thereof.

The term "$C_1$-$C_2$-haloalkylsulfinyl" is a $C_1$-$C_2$-haloalkyl group, as defined above, attached via a sulfinyl [S(O)] group. The term "$C_1$-$C_4$-haloalkylsulfinyl" is a $C_1$-$C_4$-haloalkyl group, as defined above, attached via a sulfinyl [S(O)] group. The term "$C_1$-$C_6$-haloalkylsulfinyl" is a $C_1$-$C_6$-haloalkyl group, as defined above, attached via a sulfinyl [S(O)] group. The term "$C_1$-$C_{10}$-haloalkylsulfinyl" is a $C_1$-$C_{10}$-haloalkyl group, as defined above, attached via a sulfinyl [S(O)] group. $C_1$-$C_2$-Haloalkylsulfinyl is, for example, $S(O)CH_2F$, $S(O)CHF_2$, $S(O)CF_3$, $S(O)CH_2Cl$, $S(O)CHCl_2$, $S(O)CCl_3$, chlorofluoromethylsulfinyl, dichlorofluoromethylsulfinyl, chlorodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl or $S(O)C_2F_5$. $C_1$-$C_4$-Haloalkylsulfinyl is additionally, for example, 2-fluoropropylsulfinyl, 3-fluoropropylsulfinyl, 2,2-difluoropropylsulfinyl, 2,3-difluoropropylsulfinyl, 2-chloropropylsulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, $S(O)CH_2$—$C_2F_5$, $S(O)CF_2$—$C_2F_5$, 1-($CH_2F$)-2-fluoroethylsulfinyl, 1-($CH_2Cl$)-2-chloroethylsulfinyl, 1-($CH_2Br$)-2-bromoethylsulfinyl, 4-fluorobutylsulfinyl, 4-chlorobutylsulfinyl, 4-bromobutylsulfinyl or nonafluorobutylsulfinyl. $C_1$-$C_6$-Haloalkylsulfinyl is additionally, for example, 5-fluoropentylsulfinyl, 5-chloropentylsulfinyl, 5-brompentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl.

The term "$C_1$-$C_2$-alkylsulfonyl" is a $C_1$-$C_2$-alkyl group, as defined above, attached via a sulfonyl [S(O)$_2$] group. The term "$C_1$-$C_3$-alkylsulfonyl" is a $C_1$-$C_3$-alkyl group, as defined above, attached via a sulfonyl [S(O)$_2$] group. The term "$C_1$-$C_4$-alkylsulfonyl" is a $C_1$-$C_4$-alkyl group, as defined above, attached via a sulfonyl [S(O)$_2$] group. The term "$C_1$-$C_6$-alkylsulfonyl" is a $C_1$-$C_6$-alkyl group, as defined above, attached via a sulfonyl [S(O)$_2$] group. The term "$C_1$-$C_{10}$-alkylsulfonyl" is a $C_1$-$C_{10}$-alkyl group, as defined above, attached via a sulfonyl [S(O)$_2$] group. $C_1$-$C_2$-Alkylsulfonyl is methylsulfonyl or ethylsulfonyl. $C_1$-$C_3$-Alkylsulfonyl is additionally, for example, n-propylsulfonyl or 1-methylethylsulfonyl (isopropylsulfonyl). $C_1$-$C_4$-Alkylsulfonyl is additionally, for example, butylsulfonyl, 1-methylpropylsulfonyl (sec-butylsulfonyl), 2-methylpropylsulfonyl (isobutylsulfonyl) or 1,1-dimethylethylsulfonyl (tertbutylsulfonyl). $C_1$-$C_6$-Alkylsulfonyl is additionally, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl. $C_1$-$C_8$-Alkylsulfonyl is additionally, for example, heptylsulfonyl, octylsulfonyl, 2-ethylhexylsulfonyl and positional isomers thereof. $C_1$-$C_{10}$-Alkylsulfonyl is additionally, for example, nonylsulfonyl, decylsulfonyl and positional isomers thereof.

The term "$C_1$-$C_2$-haloalkylsulfonyl" is a $C_1$-$C_2$-haloalkyl group, as defined above, attached via a sulfonyl [S(O)$_2$] group. The term "$C_1$-$C_3$-haloalkylsulfonyl" is a $C_1$-$C_3$-haloalkyl group, as defined above, attached via a sulfonyl [S(O)$_2$] group. The term "$C_1$-$C_4$-haloalkylsulfonyl" is a $C_1$-$C_4$-haloalkyl group, as defined above, attached via a sulfonyl [S(O)$_2$] group. The term "$C_1$-$C_6$-haloalkylsulfonyl" is a $C_1$-$C_6$-haloalkyl group, as defined above, attached via a sulfonyl [S(O)$_2$] group. The term "$C_1$-$C_{10}$-haloalkylsulfonyl" is a $C_1$-$C_{10}$-haloalkyl group, as defined above, attached via a sulfonyl [S(O)$_2$] group. $C_1$-$C_2$-Haloalkylsulfonyl is, for example, S(O)$_2$CH$_2$F, S(O)$_2$CHF$_2$, S(O)$_2$CF$_3$, S(O)$_2$CH$_2$Cl, S(O)$_2$CHCl$_2$, S(O)$_2$CCl$_3$, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl or S(O)$_2$C$_2$F$_5$. $C_1$-$C_3$-Haloalkylsulfonyl is additionally, for example, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, S(O)$_2$CH$_2$—C$_2$F$_5$, S(O)$_2$CF$_2$—C$_2$F$_5$, 1-(CH$_2$F)-2-fluoroethylsulfonyl, 1-(CH$_2$Cl)-2-chloroethylsulfonyl or 1-(CH$_2$Br)-2-bromoethylsulfonyl. $C_1$-$C_4$-Haloalkylsulfonyl is additionally, for example, 4-fluorobutylsulfonyl, 4-chlorobutylsulfonyl, 4-bromobutylsulfonyl or nonafluorobutylsulfonyl. $C_1$-$C_6$-Haloalkylsulfonyl is additionally, for example, 5-fluoropentylsulfonyl, 5-chloropentylsulfonyl, 5-brompentylsulfonyl, 5-iodopentylsulfonyl, undecafluoropentylsulfonyl, 6-fluorohexylsulfonyl, 6-chlorohexylsulfonyl, 6-bromohexylsulfonyl, 6-iodohexylsulfonyl or dodecafluorohexylsulfonyl.

The substituent "oxo" replaces a CH$_2$ group by a C(=O) group.

The term "$C_1$-$C_4$-alkylcarbonyl" relates to a $C_1$-$C_4$-alkyl group, as defined above, attached via a carbonyl [C(=O)] group. Examples are acetyl (methylcarbonyl), propionyl (ethylcarbonyl), propylcarbonyl, isopropylcarbonyl, n-butylcarbonyl and the like.

The term "$C_1$-$C_4$-haloalkylcarbonyl" relates to a $C_1$-$C_4$-haloalkyl group, as defined above, attached via a carbonyl [C(=O)] group. Examples are trifluoromethylcarbonyl, 2,2,2-trifluoroethylcarbonyl and the like.

The term "aminocarbonyl" is a group —C(=O)—NH$_2$.

The term "$C_1$-$C_4$-alkylaminocarbonyl" is a group —C(=O)—N(H)C$_1$-C$_4$-alkyl. Examples are methylaminocarbonyl, ethylaminocarbonyl, propylaminocarbonyl, isopropylaminocarbonyl, butylaminocarbonyl and the like.

The term "di-($C_1$-$C_4$-alkyl)aminocarbonyl" is a group —C(=O)—N(C$_1$-C$_4$-alkyl)$_2$. Examples are dimethylaminocarbonyl, diethylaminocarbonyl, ethylmethylaminocarbonyl, dipropylaminocarbonyl, diisopropylaminocarbonyl, methylpropylaminocarbonyl, methylisopropylaminocarbonyl, ethylpropylaminocarbonyl, ethylisopropylaminocarbonyl, dibutylaminocarbonyl and the like.

The remarks made below concerning preferred embodiments of the variables of the compounds of formula I, especially with respect to their substituents A, $A^1$, $A^2$, $X^1$, $B^1$, $B^2$, $B^3$, $B^4$, $B^5$, $R^{g1}$, $R^{g2}$, $R^1$, $R^2$, $R^{3a}$, $R^{3b}$, $R^{51}$, $R^{52}$, $R^{61}$, $R^{62}$, $R^{7a}$, $R^{7b}$, $R^{81}$, $R^{82}$, $R^{91}$, $R^{92}$, $R^{101a}$, $R^{101b}$, $R^{101c}$, $R^{101d}$, $R^{102a}$, $R^{102b}$, $R^{102c}$, $R^{102d}$, $R^{112a}$, $R^{112b}$, $R^{14a}$, $R^{14b}$, $R^{16}$, k, and p, the features of the use and method according to the invention and of the composition of the invention are valid both on their own and, in particular, in every possible combination with each other.

In the heterocyclic rings, $R^{16}$ may be bound to a carbon ring atom or to a secondary nitrogen ring atom (in the latter case thus replacing the hydrogen atom shown in the above E-x rings). If $R^{16}$ is bound to a nitrogen ring atom, $R^{16}$ is preferably not halogen, cyano, nitro or a radical bound via O or S, such as alkoxy, haloalkoxy, alkylthio, haloalkylthio, alkylsulfinyl, haloalkylsulfinyl, alkylsulfonyl or haloalkylsulfonyl.

In one embodiment of the invention $X^1$ is O. In another embodiment of the invention $X^1$ is CH$_2$. Preferably, however, $X^1$ is O.

W is preferably O.

In one embodiment of the invention (embodiment 1) A is $A^1$, where W, $R^{51}$ and $R^{61}$ have one of the above general, or, in particular, one of the below (for W: above) preferred meanings.

In a preferred embodiment of embodiment 1 (embodiment 1a), $R^{51}$ is hydrogen.

In another preferred embodiment of embodiment 1 (embodiment 1b)

$R^{61}$ is selected from the group consisting of $C_1$-$C_2$-alkyl which carries one radical $R^{81}$, $C_1$-$C_2$-haloalkyl which carries one radical $R^{81}$, $C_3$-$C_6$-cycloalkyl which may be substituted by 1 or 2 CN substituents; $C_3$-$C_6$-halocycloalkyl; and a heterocyclic ring selected from rings E-44 and E-53; where $R^{81}$ is selected from the group consisting of $C_3$-$C_6$-cycloalkyl which optionally carries a CN or $C_1$-haloalkyl substituent, $C_3$-$C_6$-halocycloalkyl, —C(=O)N(R$^{101c}$)R$^{101d}$, and a heterocyclic ring selected from rings E-1 to E-63 as defined above and in particular from rings E-1 to E-9; where $R^{101c}$ is selected from the group consisting of hydrogen and $C_1$-$C_4$-alkyl; and $R^{101d}$ is selected from the group consisting of hydrogen, $C_1$-$C_6$-alkyl and $C_1$-$C_6$-haloalkyl.

More particularly (embodiment 1c)

$R^{61}$ is selected from the group consisting of $C_1$-$C_2$-alkyl which carries one radical $R^{81}$, $C_3$-$C_6$-cycloalkyl and a heterocyclic ring selected from rings E-44 and E-53; where $R^{81}$ is selected from the group consisting of $C_3$-$C_6$-cycloalkyl, —C(=O)N(R$^{101c}$)R$^{101d}$, and a heterocyclic ring selected from rings E-1 to E-9; where $R^{101c}$ is hydrogen; and $R^{101d}$ is selected from the group consisting of $C_1$-$C_6$-alkyl and $C_1$-$C_6$-haloalkyl.

In another particular embodiment of embodiment 1 (embodiment 1d)

$R^{61}$ is selected from $C_1$-$C_4$-alkyl carrying one substituent $R^{81}$, ring E-44-1 and ring E-53-1

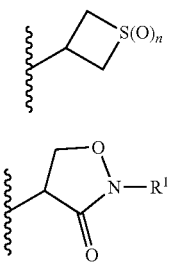

E-44-1

E-53-1 wherein n is 0, 1 or 2; and $R^{16a}$ is selected from the group consisting of hydrogen, $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl and $CH_2$—($C_3$-$C_6$-cycloalkyl); and in particular from hydrogen and $C_1$-$C_4$-alkyl; and $R^{81}$ is selected from rings E-44-1 and E-57-1

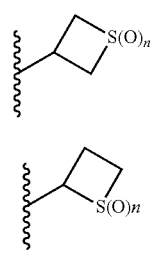

E-44-1

E-57-1 wherein n is 0, 1 or 2

In a more preferred embodiment of embodiment 1d (embodiment 1e) $R^{61}$ is selected from methyl carrying one substituent $R^{81}$ (—$CH_2$—$R^{81}$), ring E-44-1 and ring E-53-1, where $R^{81}$, ring E-44-1 and ring E-53-1 are as defined in embodiment 1d.

In a particular embodiment (embodiment 1f) $R^{51}$ is hydrogen and $R^{61}$ is as defined in embodiment 1b, 1c, 1d or 1e.

In one embodiment of the invention (embodiment 2) A is $A^2$, where $R^{7a}$, $R^{7b}$, $R^{52}$ and $R^{62}$ have one of the above general, or, in particular, one of the below preferred meanings.

In a preferred embodiment of embodiment 2 (embodiment 2a), $R^{7a}$ is hydrogen and $R^{7b}$ is selected from hydrogen, $CH_3$, $CF_3$ and CN. In a particular embodiment of embodiment 2a (embodiment 2aa), $R^{7a}$ and $R^{7b}$ are hydrogen.

In another preferred embodiment of embodiment 2 (embodiment 2b), $R^{52}$ is selected from hydrogen and $C_1$-$C_3$-alkyl, and is in particular hydrogen.

In another preferred embodiment of embodiment 2 (embodiment 2c), $R^{62}$ is selected from $C_1$-$C_6$-alkyl, $C_1$-$C_6$-haloalkyl, $C_1$-$C_4$-alkyl substituted by one radical $R^{82}$; $C_3$-$C_6$-cycloalkyl which optionally carries a CN substituent, $C_3$-$C_6$-halocycloalkyl, phenyl which is optionally substituted with 1, 2, 3, 4 or 5 substituents $R^{16}$; and a heterocyclic ring selected from rings of formulae E-1 to E-63 as defined above; where $R^{82}$ and $R^{16}$ have one of the above general, or, in particular, one of the below preferred meanings.

$R^{82}$ is preferably selected from CN, $C_3$-$C_6$-cycloalkyl which optionally carries a CN or $CF_3$ substituent; $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, phenyl, optionally substituted with 1, 2 or 3 substituents $R^{16}$, and a heterocyclic ring selected from rings E-1 to E-63 as defined above.

$R^{16}$ in phenyl and in rings E-1 to E-63 of embodiment 2 or 2c is preferably selected from halogen, cyano, $C_1$-$C_4$-alkyl, $C_1$-$C_4$-haloalkyl, $C_1$-$C_4$-alkoxy and $C_1$-$C_4$-haloalkoxy.

In a particular embodiment of embodiment 2 (embodiment 2d), $R^{7a}$ is hydrogen;

$R^{7b}$ is selected from hydrogen, $CH_3$, $CF_3$ and CN;

$R^{52}$ is selected from hydrogen and $C_1$-$C_3$-alkyl; and $R^{62}$ is selected from $C_1$-$C_6$-alkyl, $C_1$-$C_6$-haloalkyl, $C_1$-$C_4$-alkyl substituted by one radical $R^{82}$; $C_3$-$C_6$-cycloalkyl which optionally carries a CN substituent; $C_3$-$C_6$-halocycloalkyl, phenyl which is optionally substituted with 1, 2, 3, 4 or 5 substituents $R^{16}$; and a heterocyclic ring selected from rings of formulae E-1 to E-63 as defined above; where $R^{82}$ is selected from CN, $C_3$-$C_6$-cycloalkyl which optionally carries a CN or $CF_3$ substituent; $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, phenyl, optionally substituted with 1, 2 or 3 substituents $R^{16}$; and a heterocyclic ring selected from rings E-1 to E-63 as defined above; and $R^{16}$ in phenyl and in rings E-1 to E-63 is selected from halogen, cyano, $C_1$-$C_4$-alkyl, $C_1$-$C_4$-haloalkyl, $C_1$-$C_4$-alkoxy and $C_1$-$C_4$-haloalkoxy.

In a more particular embodiment of embodiment 2 (embodiment 2e), $R^{7a}$ and $R^{7b}$ are hydrogen, $R^{52}$ is hydrogen; and $R^{62}$ is selected from $C_1$-$C_6$-alkyl, $C_1$-$C_6$-haloalkyl, $C_1$-$C_4$-alkyl substituted by one radical $R^{82}$; $C_3$-$C_6$-cycloalkyl which optionally carries a CN substituent; and $C_3$-$C_6$-halocycloalkyl; where $R^{82}$ is selected from CN, $C_3$-$C_6$-cycloalkyl which optionally carries a CN or $CF_3$ substituent; $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl and $C_1$-$C_6$-haloalkylsulfonyl; and in particular from $C_1$-$C_6$-alkylsulfonyl and $C_1$-$C_6$-haloalkylsulfonyl.

In a specific embodiment of embodiment 2 (embodiment 2f), $R^{7a}$ and $R^{7b}$ are hydrogen, $R^{52}$ is hydrogen; and $R^{62}$ is selected from $C_1$-$C_6$-alkyl, $C_1$-$C_4$-alkyl substituted by one radical $R^{82}$; and $C_3$-$C_6$-cycloalkyl; where $R^{82}$ is selected from $C_6$-alkylsulfonyl and $C_1$-$C_6$-haloalkylsulfonyl.

Preferably, $B^2$ is $CR^2$, where $R^2$ is not hydrogen, and $B^1$, $B^3$, $B^4$ and $B^5$ are $CR^2$, where $R^2$ has one of the above general, or, in particular, one of the below preferred meanings. More preferably $B^1$ and $B^5$ are CH, $B^2$ is $CR^2$, where $R^2$ is not hydrogen, and $B^3$ and $B^4$ are $CR^2$, where $R^2$ has one of the above general, or, in particular, one of the below preferred meanings.

Preferably $R^2$ is selected from hydrogen, F, Cl, Br, $OCF_3$ and $CF_3$, and in particular from hydrogen, F and Cl.

In a particular embodiment (embodiment 3a), in compounds I, $B^2$ is $CR^2$, where $R^2$ is not hydrogen, and $B^1$, $B^3$, $B^4$ and $B^5$ are $CR^2$, where $R^2$ has one of the above general, or, in particular, one of the above preferred meanings; A is $A^1$, W is O; and $R^{51}$ and $R^{61}$ are as defined in any of the above embodiments 1a, 1b, 1c, 1d, 1e or 1f.

In a more particular embodiment (embodiment 3b), in compounds I, $B^1$ and $B^5$ are CH, $B^2$ is $CR^2$, where $R^2$ is not hydrogen, and $B^3$ and $B^4$ are $CR^2$, where $R^2$ has one of the above general, or, in particular, one of the above preferred meanings; A is $A^1$, W is O; and $R^{51}$ and $R^{61}$ are as defined in any of the above embodiments 1a, 1 b, 1c, 1d, 1e or 1f.

In another particular embodiment (embodiment 3c), in compounds I, $B^2$ is $CR^2$, where $R^2$ is not hydrogen, and $B^1$, $B^3$, $B^4$ and $B^5$ are $CR^2$, where $R^2$ has one of the above general, or, in particular, one of the above preferred meanings; A is $A^2$, and $R^{7a}$, $R^{7b}$, $R^{52}$ and $R^{62}$ are as defined in any of the above embodiments 2a, 2aa, 2b, 2c, 2d, 2e or 2f.

In another more particular embodiment (embodiment 3d), in compounds I, $B^1$ and $B^5$ are CH, $B^2$ is $CR^2$, where $R^2$ is not hydrogen, and $B^3$ and $B^4$ are $CR^2$, where $R^2$ has one of the above general, or, in particular, one of the above preferred meanings; A is $A^2$, and $R^{7a}$, $R^{7b}$, $R^{52}$ and $R^{62}$ are as defined in any of the above embodiments 2a, 2aa, 2b, 2c, 2d, 2e or 2f.

Preferably (embodiment 4) $R^{g1}$ and $R^{g2}$ form together a bridging group selected from —$CH_2CH_2O$—, —$OCH_2CH_2$—, —$CH_2OCH_2$—, —$OCH_2O$—, —$CH_2CH_2S$—, —$SCH_2CH_2$—, —$CH_2SCH_2$—, —$SCH_2S$—, —$OCH_2S$—, —$SCH_2O$—, —$CH_2CH_2S(O)$—, —$S(O)CH_2CH_2$—, —$CH_2S(O)CH_2$—, —$CH_2CH_2S(O)_2$—, —$S(O)_2CH_2CH_2$—, —$CH_2S(O)_2CH_2$—, —$CH_2CH_2CH_2O$— and —$OCH_2CH_2CH_2$—, and in particular from —$CH_2CH_2O$—, —$OCH_2CH_2$—, —$CH_2OCH_2$—, —$OCH_2O$—, —$CH_2CH_2S$—, —$SCH_2CH_2$—, —$CH_2SCH_2$—, —$SCH_2S$—, —$OCH_2S$— and —$SCH_2O$—. More preferably (embodiment 4a) $R^{g1}$ and $R^{g2}$ form together a bridging group selected from —$CH_2CH_2O$—, —$OCH_2CH_2$—, —$CH_2OCH_2$—, —$OCH_2O$—, —$CH_2CH_2S$— and —$SCH_2CH_2$—, and in particular form —$CH_2CH_2O$— (so that 0 is bound in the position of $R^{g2}$). Alternatively, in a more preferred embodiment (embodiment 4b), $R^{g1}$ and $R^{g2}$ form together a bridging group selected from —$CH_2CH_2O$—, —$CH_2OCH_2$—, —$OCH_2O$—, —$CH_2CH_2S$—, —$CH_2SCH_2$—, —$CH_2CH_2S(O)$—, —$CH_2S(O)CH_2$—, —$CH_2CH_2S(O)_2$—, —$CH_2S(O)_2CH_2$— and —$CH_2CH_2CH_2O$—. The C, S or O atom on the right part of the bridging group is bound in position of $R^{g2}$ and the C, S or O atom on the left part in position of $R^{g1}$. For instance, in —$CH_2CH_2O$—, O is bound in position of $R^{g2}$.

In a particular embodiment (embodiment 4c) $R^{g1}$ and $R^{g2}$ form together a bridging group selected from —$CH_2CH_2O$—, —$OCH_2CH_2$—, —$CH_2OCH_2$—, —$OCH_2O$—, —$CH_2CH_2S$—, —$SCH_2CH_2$—, —$CH_2SCH_2$—, —$SCH_2S$—, —$OCH_2S$—, —$SCH_2O$—, —$CH_2CH_2S(O)$—, —$S(O)CH_2CH_2$—, —$CH_2S(O)CH_2$—, —$CH_2CH_2S(O)_2$—, —$S(O)_2CH_2CH_2$—, —$CH_2S(O)_2CH_2$—, —$CH_2CH_2CH_2O$— and —$OCH_2CH_2CH_2$—, and $B^1$, $B^2$, $B^3$, $B^4$, $B^5$, $A^1$, $A^2$, W, $R^{51}$, $R^{61}$, $R^{7a}$, $R^{7b}$, $R^{52}$ and $R^{62}$ are as defined in any of embodiments 1a, 1b, 1c, 1d, 1e, 1f, 2a, 2aa, 2b, 2c, 2d, 2e, 2f, 3a, 3b, 3c or 3d.

In a more particular embodiment (embodiment 4d) $R^{g1}$ and $R^{g2}$ form together a bridging group selected from —$CH_2CH_2O$—, —$OCH_2CH_2$—, —$CH_2OCH_2$—, —$OCH_2O$—, —$CH_2CH_2S$—, —$SCH_2CH_2$—, —$CH_2SCH_2$—, —$SCH_2S$—, —$OCH_2S$— and —$SCH_2O$—, and $B^1$, $B^2$, $B^3$, $B^4$, $B^5$, $A^1$, $A^2$, W, $R^{51}$, $R^{61}$, $R^{7a}$, $R^{7b}$, $R^{52}$ and $R^{62}$ are as defined in any embodiments 1a, 1b, 1c, 1d, 1e, 1f, 2a, 2aa, 2b, 2c, 2d, 2e, 2f, 3a, 3b, 3c or 3d.

In a more particular embodiment (embodiment 4e) $R^{g1}$ and $R^{g2}$ form together a bridging group selected from —$CH_2CH_2O$—, —$OCH_2CH_2$—, —$CH_2OCH_2$—, —$OCH_2O$—, —$CH_2CH_2S$— and —$SCH_2CH_2$—, and $B^1$, $B^2$, $B^3$, $B^4$, $B^5$, $A^1$, $A^2$, W, $R^{51}$, $R^{61}$, $R^{7a}$, $R^{7b}$, $R^{52}$ and $R^{62}$ are as defined in any embodiments 1a, 1b, 1c, 1d, 1e, 1f, 2a, 2aa, 2b, 2c, 2d, 2e, 2f, 3a, 3b, 3c or 3d.

In another more particular embodiment (embodiment 4f) $R^{g1}$ and $R^{g2}$ form together a bridging group selected from —$CH_2CH_2O$—, —$CH_2OCH_2$—, —$OCH_2O$—, —$CH_2CH_2S$—, —$CH_2SCH_2$—, —$CH_2CH_2S(O)$—, —$CH_2S(O)CH_2$—, —$CH_2CH_2S(O)_2$—, —$CH_2S(O)_2CH_2$— and —$CH_2CH_2CH_2O$—, and $B^1$, $B^2$, $B^3$, $B^4$, $B^5$, $A^1$, $A^2$, W, $R^{51}$, $R^{61}$, $R^{7a}$, $R^{7b}$, $R^{52}$ and $R^{62}$ are as defined in any embodiments 1a, 1b, 1c, 1d, 1e, 1f, 2a, 2aa, 2b, 2c, 2d, 2e, 2f, 3a, 3b, 3c or 3d.

In a very particular embodiment (embodiment 4g) $R^{g1}$ and $R^{g2}$ form together —$CH_2CH_2O$— (so that O is bound in the position of $R^{g2}$), and $B^1$, $B^2$, $B^3$, $B^4$, $B^5$, $A^1$, $A^2$, W, $R^{51}$, $R^{61}$, $R^{7a}$, $R^{7b}$, $R^{52}$ and $R^{62}$ are as defined in any embodiments 1a, 1b, 1c, 1d, 1e, 1f, 2a, 2aa, 2b, 2c, 2d, 2e, 2f, 3a, 3b, 3c or 3d.

Preferably, $R^1$ is $CF_3$. In particular (embodiment 5) $R^1$ is $CF_3$ and $B^1$, $B^2$, $B^3$, $B^4$, $B^5$, $A^1$, $A^2$, W, $R^{51}$, $R^{61}$, $R^{7a}$, $R^{7b}$, $R^{52}$, $R^{62}$, $R^{g1}$ and $R^{g2}$ are as defined in any embodiments 1a, 1b, 1c, 1d, 1e, 1f, 2a, 2aa, 2b, 2c, 2d, 2e, 2f, 3a, 3b, 3c, 3d, 4, 4a, 4b, 4c, 4d, 4e, 4f or 4g.

Preferably, $R^{3a}$ and $R^{3b}$ are independently of each other selected from hydrogen and fluorine, and are in particular hydrogen. In particular (embodiment 6) $R^{3a}$ and $R^{3b}$ are independently of each other selected from hydrogen and fluorine, and are in particular hydrogen, and $B^1$, $B^2$, $B^3$, $B^4$, $B^5$, $A^1$, $A^2$, W, $R^1$, $R^{51}$, $R^{61}$, $R^{7a}$, $R^{7b}$, $R^{52}$, $R^{62}$, $R^{g1}$ and $R^{g2}$ are as defined in any embodiments 1a, 1b, 1c, Id, 1e, 1f, 2a, 2aa, 2b, 2c, 2d, 2e, 2f, 3a, 3b, 3c, 3d, 4, 4a, 4b, 4c, 4d, 4e, 4f, 4g or 5.

In a particular embodiment, the compound of formula I is a compound of formula IA or an N-oxide, a stereoisomer or an agriculturally or veterinarily acceptable salt thereof

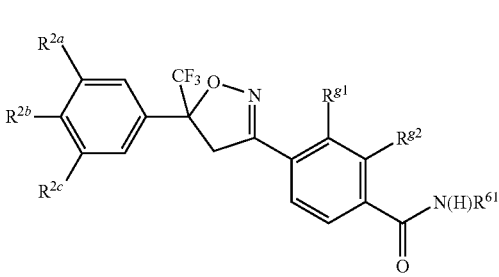

wherein
$R^{g1}$ and $R^{g2}$ have one of the above general or, in particular, one of the above preferred meanings;
$R^{2a}$ is Cl, $R^{2b}$ is F, $R^{2c}$ is Cl; and
$R^{61}$ is $CH_2$—C(O)—N(H)—$R^{101d}$, wherein $R^{101d}$ is selected from the group consisting of $C_1$-$C_4$-alkyl, $C_2$-$C_4$-alkyl substituted with 1 or 2 fluorine atoms, $C_2$-$C_4$-alkenyl, $C_2$-$C_4$-alkynyl, $CH_2$—CN, $C_3$-$C_6$-cycloalkyl, $C_3$-$C_6$-halocycloalkyl and $C_3$-$C_6$-cycloalkylmethyl.

In another particular embodiment, the compound of formula I is a compound of formula IA as defined above or an N-oxide, a stereoisomer or an agriculturally or veterinarily acceptable salt thereof, wherein $R^{g1}$ and $R^{g2}$ have one of the above general or, in particular, one of the above preferred meanings;

$R^{2a}$ is Cl, $R^{2b}$ is F, $R^{2c}$ is Cl; and $R^{61}$ is —$CH_2$—$R^{81}$, wherein
  $R^{81}$ is selected from rings E-5, E-6, E-7, E-19, E-25, E-27, E-44 and E-57 as defined above, where the rings E-5, E-6, E-7, E-19, E-27, E-44 and E-57 are unsubstituted (k is 0) or carry 1 or 2 substituents $R^{16}$ (k is 1 or 2) and where ring E-25 carries one $R^{16}$ substituent on the nitrogen atom in the 1-position and optionally carries 1 or 2 further substituents $R^{16}$;
  and is in particular selected from rings E-5, E-6, E-7, E-19, E-25, E-27, E-44-1 and E-57-1, where the rings E-5, E-6, E-7, E-19 and E-27 are unsubstituted (k is 0) or carry 1 or 2 substituents $R^{16}$ (k is 1 or 2) and where ring E-25 carries one $R^{16}$ substituent on the nitrogen atom in the 1-position and optionally carries 1 or 2 further substituents $R^{16}$;
  where in the above rings
  each $R^{16}$ is independently selected from halogen, cyano, nitro, $C_1$-$C_2$-alkyl, $C_1$-$C_2$-haloalkyl, $C_1$-$C_2$-alkoxy, $C_1$-$C_2$-haloalkoxy, $C_1$-$C_2$-alkylthio, $C_1$-$C_2$-haloalkylthio, $C_1$-$C_2$-alkylsulfinyl, $C_1$-$C_2$-haloalkylsulfinyl, $C_1$-$C_2$-alkylsulfonyl, $C_1$-$C_2$-haloalkylsulfonyl, $C_3$-$C_4$-cycloalkyl, $C_3$-$C_4$-halocycloalkyl, $C_2$-$C_3$-alkenyl and $C_2$-$C_3$-alkynyl;
  where however $R^{16}$ bound in the 1-position of E-25 is not halogen, cyano, nitro, $C_1$-$C_2$-alkoxy, $C_1$-$C_2$-haloalkoxy, $C_1$-$C_2$-alkylthio, $C_1$-$C_2$-haloalkylthio, $C_1$-$C_2$-alkylsulfinyl, $C_1$-$C_2$-haloalkylsulfinyl, $C_1$-$C_2$-alkylsulfonyl or $C_1$-$C_2$-haloalkylsulfonyl.

In yet another particular embodiment, the compound of formula I is a compound of formula IA as defined above or an N-oxide, a stereoisomer or an agriculturally or veterinarily acceptable salt thereof, wherein $R^{g1}$ and $R^{g2}$ have one of the above general or, in particular, one of the above preferred meanings;

$R^{2a}$ is Cl, $R^{2b}$ is F, $R^{2c}$ is Cl; and $R^{61}$ is selected from rings E-2, E-4, E-6, E-8, E-9, E-44, E-46, E-51 and E-53 as defined above, where the rings E-2, E-4, E-6, E-8, E-9, E-44, E-46 and E-53 are unsubstituted (k is 0) or carry 1 or 2 substituents $R^{16}$ (k is 1 or 2), wherein
  each $R^{16}$ is independently selected from halogen, cyano, nitro, $C_1$-$C_2$-alkyl, $C_1$-$C_2$-haloalkyl, $C_1$-$C_2$-alkoxy, $C_1$-$C_2$-haloalkoxy, $C_1$-$C_2$-alkylthio, $C_1$-$C_2$-haloalkylthio, $C_1$-$C_2$-alkylsulfinyl, $C_1$-$C_2$-haloalkylsulfinyl, $C_1$-$C_2$-alkylsulfonyl, $C_1$-$C_2$-haloalkylsulfonyl, $C_3$-$C_4$-cycloalkyl, $C_3$-$C_4$-halocycloalkyl, $C_2$-$C_3$-alkenyl and $C_2$-$C_3$-alkynyl; and
  where ring E-51 is a ring of formula E-51-1

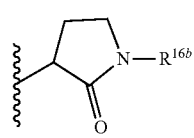

E-51-1 wherein
  $R^{16b}$ is selected from the group consisting of hydrogen, $C_1$-$C_2$-alkyl, $C_1$-$C_2$-haloalkyl, $C_3$-$C_4$-cycloalkyl, $C_3$-$C_4$-halocycloalkyl, $C_2$-$C_3$-alkenyl and $C_2$-$C_3$-alkynyl.

In this embodiment, rings E-44 and E-53 are preferably rings E-44-1 and E-53-1 as defined above.

In yet another particular embodiment, the compound of formula I is a compound of formula IA as defined above or an N-oxide, a stereoisomer or an agriculturally or veterinarily acceptable salt thereof, wherein $R^{g1}$ and $R^{g2}$ have one of the above general or, in particular, one of the above preferred meanings;

$R^{2a}$ is Cl, $R^{2b}$ is F, $R^{2C}$ is Cl; and $R^{61}$ is selected from $C_2$-$C_4$-alkyl which may be substituted with 1 or 2 fluorine atoms, cyclopropyl, $C_3$-$C_5$-halocycloalkyl, $CH_2$—($C_3$-$C_5$-halocycloalkyl), $CH_2$-(1-cyano-($C_3$-$C_5$-cycloalkyl)), $C_2$-$C_4$-alkenyl, $C_2$-$C_4$-alkynyl, $CH_2$—CN and —CH=$NOR^{91}$, wherein $R^{91}$ is selected from $C_1$-$C_3$-alkyl and $C_1$-$C_3$-haloalkyl.

In yet another particular embodiment, the compound of formula I is a compound of formula IA as defined above or an N-oxide, a stereoisomer or an agriculturally or veterinarily acceptable salt thereof, wherein $R^{g1}$ and $R^{g2}$ have one of the above general or, in particular, one of the above preferred meanings;

$R^{2a}$ is Cl, $R^{2b}$ is F, $R^{2c}$ is Cl; and $R^{61}$ is $N(H)R^{101b}$, wherein
  $R^{101b}$ is selected from —C(O)—N(H)$R^{14b}$ and rings E-1 and E-7 as defined above, where
    $R^{14b}$ is selected from $C_1$-$C_3$-alkyl, $C_1$-$C_3$-haloalkyl and cyclopropyl; and where in rings E-1 and E-7
    k is 0, 1 or 2; and
    each $R^{16}$ is independently selected from halogen, cyano, nitro, $C_1$-$C_2$-alkyl, $C_1$-$C_2$-haloalkyl, $C_1$-$C_2$-alkoxy, $C_1$-$C_2$-haloalkoxy, $C_1$-$C_2$-alkylthio, $C_1$-$C_2$-haloalkylthio, $C_1$-$C_2$-alkylsulfinyl, $C_1$-$C_2$-haloalkylsulfinyl, $C_1$-$C_2$-alkylsulfonyl, $C_1$-$C_2$-haloalkylsulfonyl, $C_3$-$C_4$-cycloalkyl, $C_3$-$C_4$-halocycloalkyl, $C_2$-$C_3$-alkenyl, $C_2$-$C_3$-alkynyl.

In another particular embodiment, the compound of formula I is a compound of formula IA as defined above or an N-oxide, a stereoisomer or an agriculturally or veterinarily acceptable salt thereof, wherein $R^{g1}$ and $R^{g2}$ have one of the above general or, in particular, one of the above preferred meanings;

$R^{2a}$ is Cl, $R^{2b}$ is H, $R^{2c}$ is Cl; and $R^{61}$ is $CH_2$—C(O)—N(H)—$R^{101d}$, wherein
  $R^{101d}$ is selected from the group consisting of 2,2-difluoroethyl, 2,2,2-trifluoroethyl, cyclopropyl, cyclopropylmethyl, allyl and propargyl.

In another particular embodiment, the compound of formula I is a compound of formula IA as defined above or an N-oxide, a stereoisomer or an agriculturally or veterinarily acceptable salt thereof, wherein $R^{g1}$ and $R^{g2}$ have one of the above general or, in particular, one of the above preferred meanings;

$R^{2a}$ is Cl, $R^{2b}$ is H, $R^{2c}$ is Cl; and $R^{61}$ is —$CH_2$—$R^{81}$, wherein
  $R^{81}$ is selected from following rings: E-1, E-7, E-19, E-44, E-47 and E-57, where in rings E-1, E-7, E-19, E-44, E-47 and E-57 k is 0.

In another particular embodiment, the compound of formula I is a compound of formula IA as defined above or an N-oxide, a stereoisomer or an agriculturally or veterinarily acceptable salt thereof, wherein $R^{g1}$ and $R^{g2}$ have one of the above general or, in particular, one of the above preferred meanings;
$R^{2a}$ is Cl, $R^{2b}$ is H, $R^{2c}$ is Cl; and
$R^{61}$ is selected from rings E-9, E-44, E-46 and E-53; where in rings E-9, E-44 and E-46 k is 0; and is in particular selected from rings E-9, E-44, E-46 and E-53-1 with $R^{16a}$=H, methyl, ethyl or 2,2,2-trifluoroethyl; where in rings E-9, E-44 and E-46 k is 0.

In another particular embodiment, the compound of formula I is a compound of formula IA as defined above or an N-oxide, a stereoisomer or an agriculturally or veterinarily acceptable salt thereof, wherein
$R^{g1}$ and $R^{g2}$ have one of the above general or, in particular, one of the above preferred meanings;
$R^{2a}$ is Cl, $R^{2b}$ is H, $R^{2c}$ is Cl; and
$R^{61}$ is selected from 2,2-difluoroethyl, 2,2,2-trifluoroethyl, cyclopropyl, 2,2-difluorocyclopropyl, 1-cyanocyclopropyl, cyclobutyl, 3,3-difluorocyclobutyl, cyclopropylmethyl, 2,2-difluorocyclopropylmethyl, 1-cyanocyclopropylmethyl, cyclobutylmethyl, 3,3-difluorocyclobutylmethyl, allyl, propargyl and —CH=NOCH$_3$.

In another particular embodiment, the compound of formula I is a compound of formula IA as defined above or an N-oxide, a stereoisomer or an agriculturally or veterinarily acceptable salt thereof, wherein
$R^{g1}$ and $R^{g2}$ have one of the above general or, in particular, one of the above preferred meanings;
$R^{2a}$ is Cl, $R^{2b}$ is H, $R^{2c}$ is Cl; and
$R^{61}$ is N(H)$R^{101b}$, wherein
$R^{101b}$ is selected from —C(O)—N(H)—CH$_2$CF$_3$ and rings E-1 and E-7, where in rings E-1 and E-7 k is 0.

In another particular embodiment, the compound of formula I is a compound of formula IB or an N-oxide, a stereoisomer or an agriculturally or veterinarily acceptable salt thereof

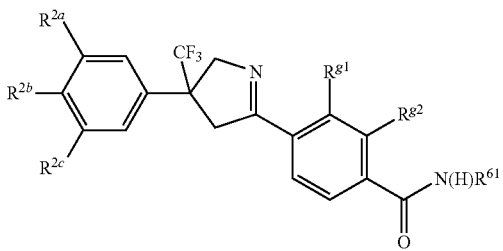

IB $R^{g1}$ and $R^{g2}$ have one of the above general or, in particular, one of the above preferred meanings;
$R^{2a}$ is Cl, $R^{2b}$ is F, $R^{2c}$ is Cl; and
$R^{61}$ is CH$_2$—C(O)—N(H)—$R^{101d}$, wherein
$R^{101d}$ is selected from the group consisting of 2,2-difluoroethyl, 2,2,2-trifluoroethyl, cyclopropyl, cyclopropylmethyl, allyl and propargyl.

In another particular embodiment, the compound of formula I is a compound of formula IB as defined above or an N-oxide, a stereoisomer or an agriculturally or veterinarily acceptable salt thereof, wherein
$R^{g1}$ and $R^{g2}$ have one of the above general or, in particular, one of the above preferred meanings;
$R^{2a}$ is Cl, $R^{2b}$ is F, $R^{2c}$ is Cl; and
$R^{61}$ is —CH$_2$—$R^{81}$, wherein
$R^{81}$ is selected from following rings: E-1, E-7, E-19, E-44, E-47 and E-57, where in rings E-1, E-7, E-19, E-44, E-47 and E-57 k is 0.

In another particular embodiment, the compound of formula I is a compound of formula IB as defined above or an N-oxide, a stereoisomer or an agriculturally or veterinarily acceptable salt thereof, wherein
$R^{g1}$ and $R^{g2}$ have one of the above general or, in particular, one of the above preferred meanings;
$R^{2a}$ is Cl, $R^{2b}$ is F, $R^{2c}$ is Cl; and
$R^{61}$ is selected from rings E-9, E-44, E-46 and E-53; where in rings E-9, E-44 and E-46 k is 0; and is in particular selected from rings E-9, E-44, E-46 and E-53-1 with $R^{16a}$=H, methyl, ethyl or 2,2,2-trifluoroethyl; where in rings E-9, E-44 and E-46 k is 0.

In another particular embodiment, the compound of formula I is a compound of formula IB as defined above or an N-oxide, a stereoisomer or an agriculturally or veterinarily acceptable salt thereof, wherein
$R^{g1}$ and $R^{g2}$ have one of the above general or, in particular, one of the above preferred meanings;
$R^{2a}$ is Cl, $R^{2b}$ is F, $R^{2c}$ is Cl; and
$R^{61}$ is selected from 2,2-difluoroethyl, 2,2,2-trifluoroethyl, cyclopropyl, 2,2-difluorocyclopropyl, 1-cyanocyclopropyl, cyclobutyl, 3,3-difluorocyclobutyl, cyclopropylmethyl, 2,2-difluorocyclopropylmethyl, 1-cyanocyclopropylmethyl, cyclobutylmethyl, 3,3-difluorocyclobutylmethyl, allyl, propargyl and —CH=NOCH$_3$.

In another particular embodiment, the compound of formula I is a compound of formula IB as defined above or an N-oxide, a stereoisomer or an agriculturally or veterinarily acceptable salt thereof, wherein
$R^{g1}$ and $R^{g2}$ have one of the above general or, in particular, one of the above preferred meanings;
$R^{2a}$ is Cl, $R^{2b}$ is F, $R^{2c}$ is Cl; and
$R^{61}$ is N(H)$R^{101b}$, wherein
$R^{101b}$ is selected from —C(O)—N(H)—CH$_2$CF$_3$ and rings E-1 and E-7, where in rings E-1 and E-7 k is 0.

In another particular embodiment, the compound of formula I is a compound of formula IB as defined above or an N-oxide, a stereoisomer or an agriculturally or veterinarily acceptable salt thereof, wherein
$R^{g1}$ and $R^{g2}$ have one of the above general or, in particular, one of the above preferred meanings;
$R^{2a}$ is Cl, $R^{2b}$ is H, $R^{2c}$ is Cl; and
$R^{61}$ is CH$_2$—C(O)—N(H)—$R^{101d}$, wherein
$R^{101d}$ is selected from the group consisting of 2,2-difluoroethyl, 2,2,2-trifluoroethyl, cyclopropyl, cyclopropylmethyl, allyl and propargyl.

In another particular embodiment, the compound of formula I is a compound of formula IB as defined above or an N-oxide, a stereoisomer or an agriculturally or veterinarily acceptable salt thereof, wherein
$R^{g1}$ and $R^{g2}$ have one of the above general or, in particular, one of the above preferred meanings;
$R^{2a}$ is Cl, $R^{2b}$ is H, $R^{2C}$ is Cl; and
$R^{61}$ is —CH$_2$—$R^{81}$, wherein
$R^{81}$ is selected from following rings: E-1, E-7, E-19, E-44, E-47 and E-57, where in rings E-1, E-7, E-19, E-44, E-47 and E-57 k is 0.

In another particular embodiment, the compound of formula I is a compound of formula IB as defined above or an N-oxide, a stereoisomer or an agriculturally or veterinarily acceptable salt thereof, wherein
$R^{g1}$ and $R^{g2}$ have one of the above general or, in particular, one of the above preferred meanings;

$R^{2a}$ is Cl, $R^{2b}$ is H, $R^{2c}$ is Cl; and $R^{61}$ is selected from rings E-9, E-44, E-46 and E-53; where in rings E-9, E-44 and E-46 k is 0; and is in particular selected from rings E-9, E-44, E-46 and E-53-1 with $R^{16a}$=H, methyl, ethyl or 2,2,2-trifluoroethyl; where in rings E-9, E-44 and E-46 k is 0.

In another particular embodiment, the compound of formula I is a compound of formula IB as defined above or an N-oxide, a stereoisomer or an agriculturally or veterinarily acceptable salt thereof, wherein $R^{g1}$ and $R^{g2}$ have one of the above general or, in particular, one of the above preferred meanings;

$R^{2a}$ is Cl, $R^{2b}$ is H, $R^{2c}$ is Cl; and $R^{61}$ is selected from 2,2-difluoroethyl, 2,2,2-trifluoroethyl, cyclopropyl, 2,2-difluorocyclopropyl, 1-cyanocyclopropyl, cyclobutyl, 3,3-difluorocyclobutyl, cyclopropylmethyl, 2,2-difluorocyclopropylmethyl, 1-cyanocyclopropylmethyl, cyclobutylmethyl, 3,3-difluorocyclobutylmethyl, allyl, propargyl and —CH=NOCH$_3$.

In another particular embodiment, the compound of formula I is a compound of formula IB as defined above or an N-oxide, a stereoisomer or an agriculturally or veterinarily acceptable salt thereof, wherein $R^{g1}$ and $R^{g2}$ have one of the above general or, in particular, one of the above preferred meanings;

$R^{2a}$ is Cl, $R^{2b}$ is H, $R^{2c}$ is Cl; and $R^{61}$ is N(H)$R^{101b}$, wherein $R^{101b}$ is selected from —C(O)—N(H)—CH$_2$CF$_3$ and rings E-1 and E-7, where in rings E-1 and E-7 k is 0.

The invention further relates to compounds of formula II

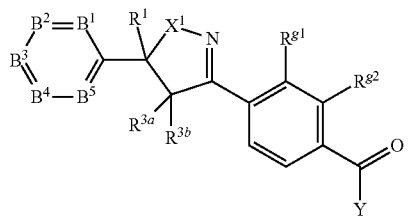

(II)

wherein $B^1$, $B^2$, $B^3$, $B^4$, $B^5$, $X^1$, $R^1$, $R^{3a}$, $R^{3b}$, $R^{g1}$ and $R^{g2}$ have one of the above general or preferred meanings; and Y is selected from hydrogen and OR$^{17}$, where $R^{17}$ is selected from hydrogen, $C_1$-$C_4$-alkyl and $C_1$-$C_4$-haloalkyl.

Compounds II have biological activity, too, but are especially useful as intermediate compounds in the preparation of compounds I wherein A is $A^1$. Thus, the invention also relates to intermediate compounds II and to the use of such compounds in the preparation of compounds I.

Examples of preferred compounds are compounds of the following formulae Ia.1 to Ia.40, where $R^{2a}$, $R^{2b}$ and $R^{2c}$ have one of the general or preferred meanings given above for $R^2$ and the other variables have one of the general or preferred meanings given above. Examples of preferred compounds are the individual compounds compiled in the tables 1 to 3400 below. Moreover, the meanings mentioned below for the individual variables in the tables are per se, independently of the combination in which they are mentioned, a particularly preferred embodiment of the substituents in question.

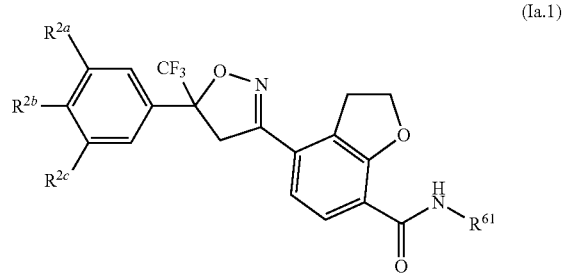

(Ia.1)

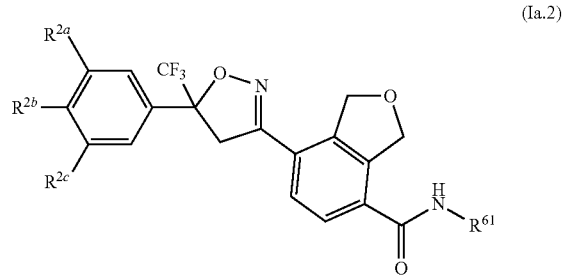

(Ia.2)

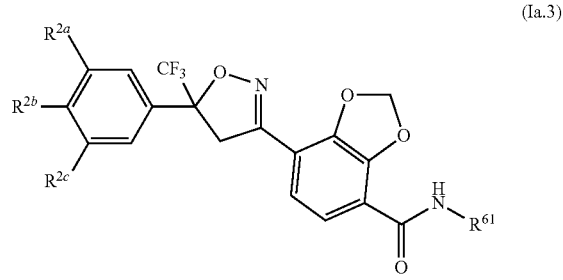

(Ia.3)

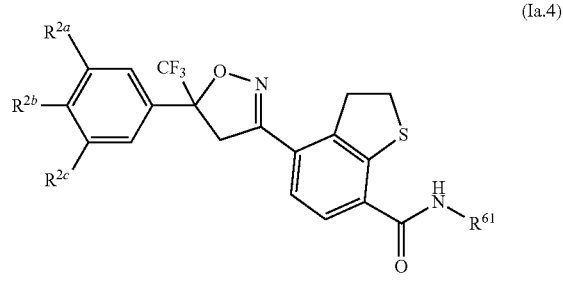

(Ia.4)

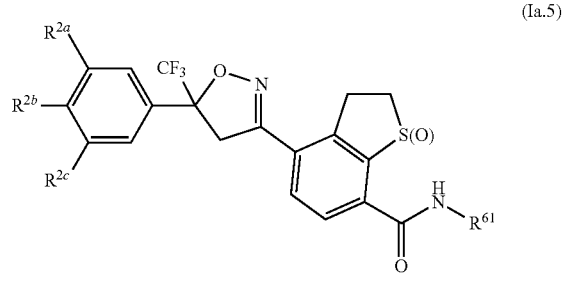

(Ia.5)

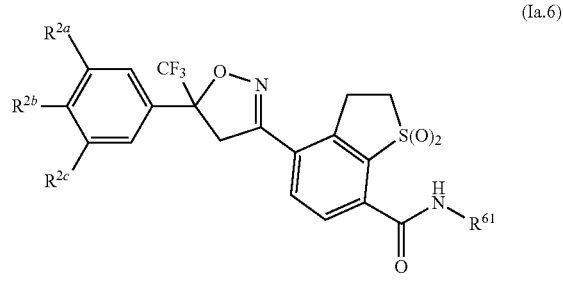

(Ia.6)

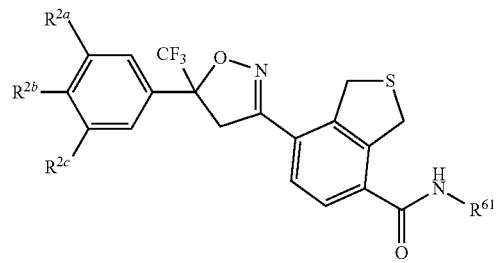
(1a.7)
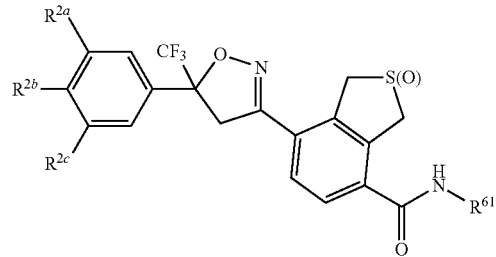
(1a.8)
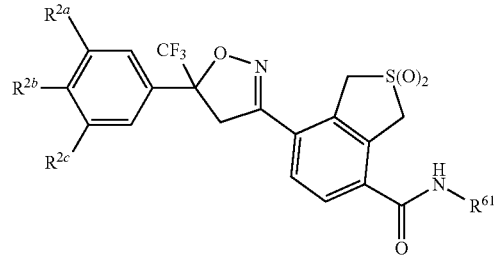
(1a.9)
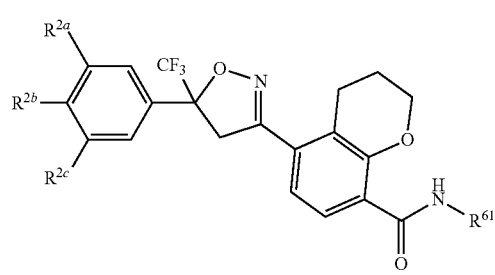
(1a.10)
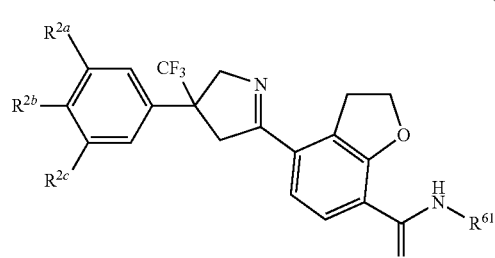
(1a.11)
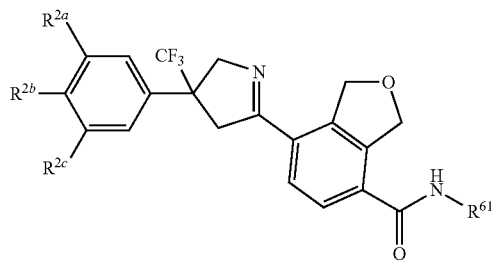
(1a.12)
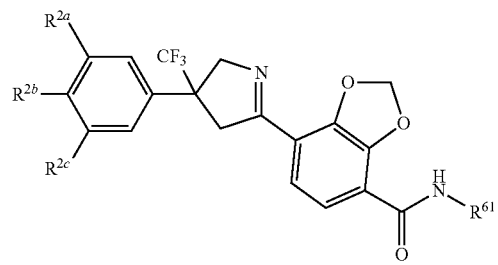
(Ia.13)
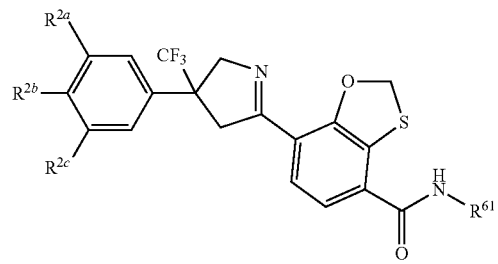
(Ia.14)
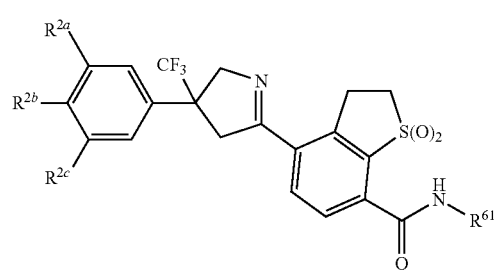
(Ia.15)
(Ia.16)

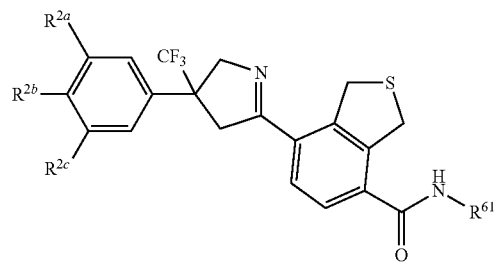
(Ia.17)
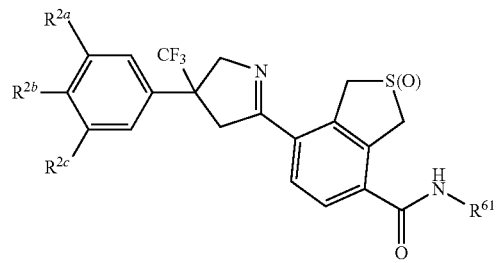
(Ia.18)
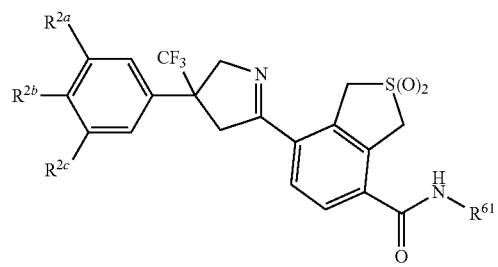
(Ia.19)
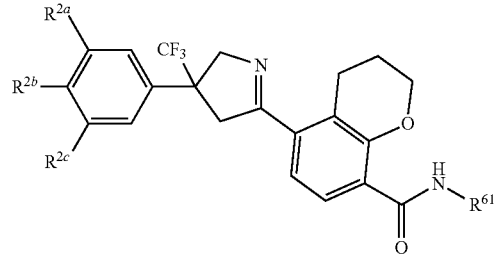
(Ia.20)
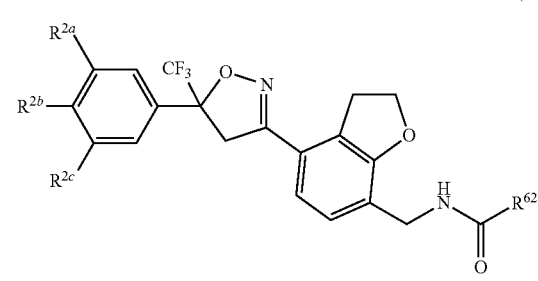
(Ia.21)
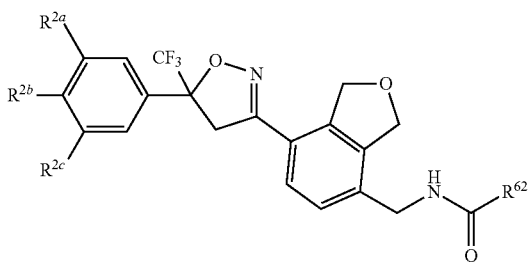
(Ia.22)
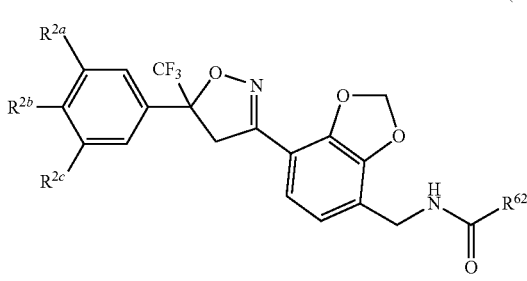
(Ia.23)
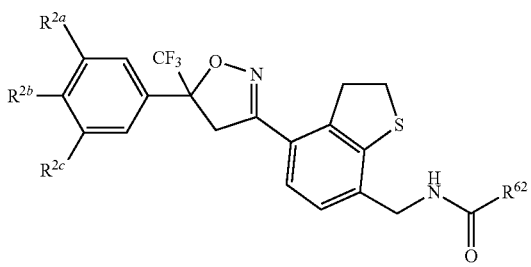
(Ia.24)
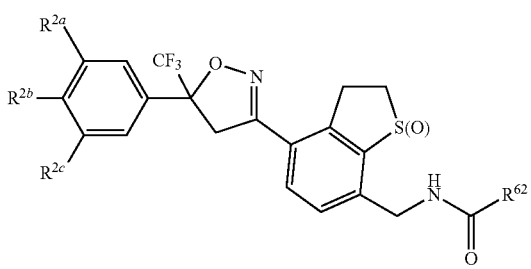
(Ia.25)
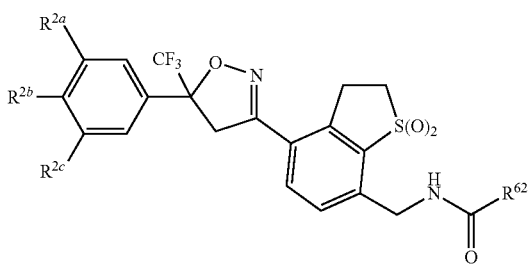
(Ia.26)

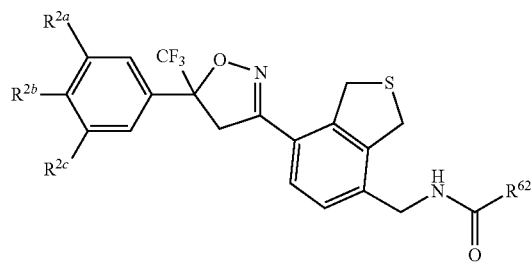
(Ia.27)
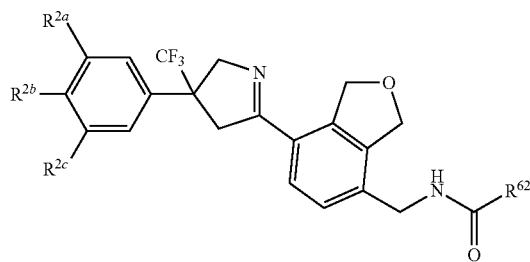
(Ia.32)
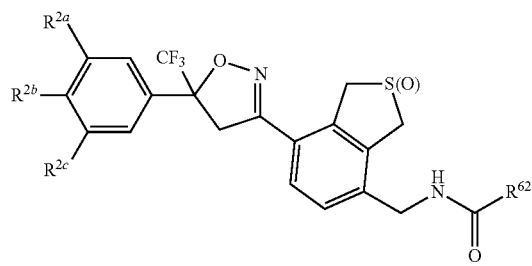
(Ia.28)
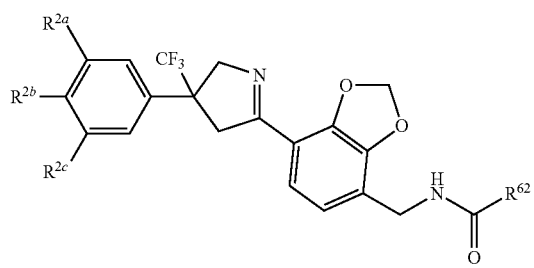
(Ia.33)
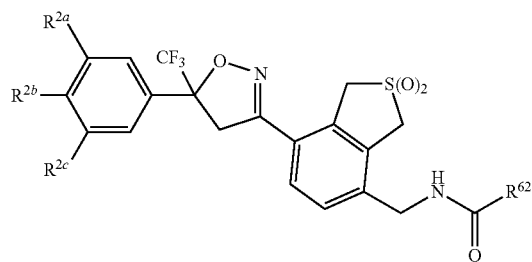
(Ia.29)
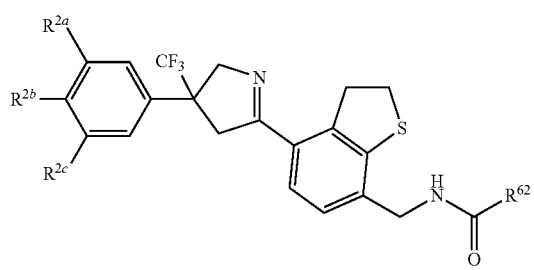
(Ia.34)
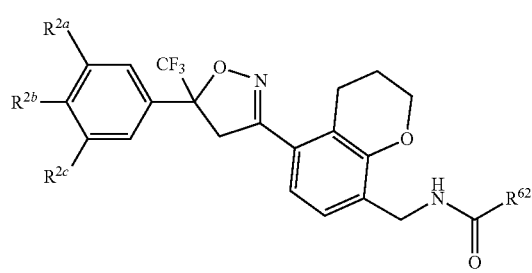
(Ia.30)
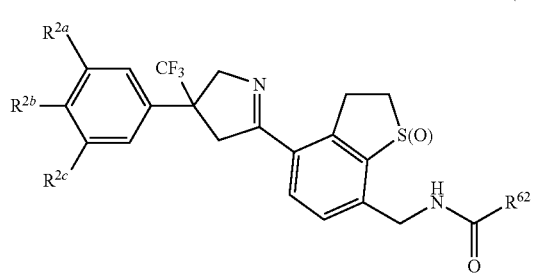
(Ia.35)
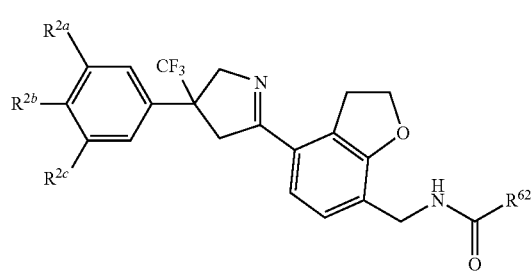
(Ia.31)
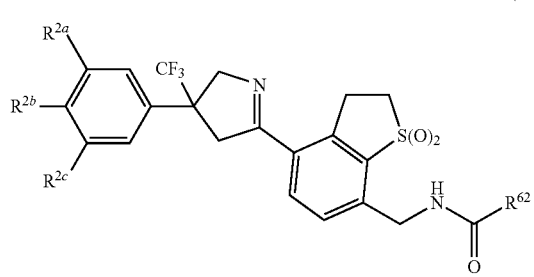
(Ia.36)

(Ia.37)

(Ia.38)

(Ia.39)

(Ia.40)

Table 1
Compounds of the formula Ia.1 in which $R^{61}$ is hydrogen, and the combination of $R^{2a}$, $R^{2b}$ and $R^{2c}$ for a compound corresponds in each case to one row of Table A Table 2
Compounds of the formula Ia.1 in which $R^{61}$ is methyl, and the combination of $R^{2a}$, $R^{2b}$ and $R^{2c}$ for a compound corresponds in each case to one row of Table A Table 3
Compounds of the formula Ia.1 in which $R^{61}$ is ethyl, and the combination of $R^{2a}$, $R^{2b}$ and $R^{2c}$ for a compound corresponds in each case to one row of Table A Table 4
Compounds of the formula Ia.1 in which $R^{61}$ is n-propyl, and the combination of $R^{2a}$, $R^{2b}$ and $R^{2c}$ for a compound corresponds in each case to one row of Table A Table 5
Compounds of the formula Ia.1 in which $R^{61}$ is n-butyl, and the combination of $R^{2a}$, $R^{2b}$ and $R^{2c}$ for a compound corresponds in each case to one row of Table A Table 6
Compounds of the formula Ia.1 in which $R^{61}$ is sec-butyl, and the combination of $R^{2a}$, $R^{2b}$ and $R^{2c}$ for a compound corresponds in each case to one row of Table A Table 7
Compounds of the formula Ia.1 in which $R^{61}$ is —CH$_2$CN, and the combination of $R^{2a}$, $R^{2b}$ and $R^{2c}$ for a compound corresponds in each case to one row of Table A Table 8
Compounds of the formula Ia.1 in which $R^{61}$ is —CH$_2$—CH=CH$_2$, and the combination of $R^{2a}$, $R^{2b}$ and $R^{2c}$ for a compound corresponds in each case to one row of Table A Table 9
Compounds of the formula Ia.1 in which $R^{61}$ is —CH$_2$—CH=CH—CH$_3$, and the combination of $R^{2a}$, $R^{2b}$ and $R^{2c}$ for a compound corresponds in each case to one row of Table A Table 10
Compounds of the formula Ia.1 in which $R^{61}$ is —CH$_2$C≡CH, and the combination of $R^{2a}$, $R^{2b}$ and $R^{2c}$ for a compound corresponds in each case to one row of Table A Table 11
Compounds of the formula Ia.1 in which $R^{61}$ is —CH$_2$CH$_2$OCH$_3$, and the combination of $R^{2a}$, $R^{2b}$ and $R^{2c}$ for a compound corresponds in each case to one row of Table A Table 12
Compounds of the formula Ia.1 in which $R^{61}$ is —CH$_2$CH$_2$OCH$_2$CH$_3$, and the combination of $R^{2a}$, $R^{2b}$ and $R^{2c}$ for a compound corresponds in each case to one row of Table A Table 13
Compounds of the formula Ia.1 in which $R^{61}$ is —CH$_2$CH$_2$OCF$_3$, and the combination of $R^{2a}$, $R^{2b}$ and $R^{2c}$ for a compound corresponds in each case to one row of Table A Table 14
Compounds of the formula Ia.1 in which $R^{61}$ is —CH$_2$CH$_2$OCH$_2$CF$_3$, and the combination of $R^{2a}$, $R^{2b}$ and $R^{2c}$ for a compound corresponds in each case to one row of Table A Table 15
Compounds of the formula Ia.1 in which $R^{61}$ is —CH$_2$CH$_2$SCH$_3$, and the combination of $R^{2a}$, $R^{2b}$ and $R^{2c}$ for a compound corresponds in each case to one row of Table A Table 16
Compounds of the formula Ia.1 in which $R^{61}$ is —CH$_2$CH$_2$S(O)CH$_3$, and the combination of $R^{2a}$, $R^{2b}$ and $R^{2c}$ for a compound corresponds in each case to one row of Table A Table 17
Compounds of the formula Ia.1 in which $R^{61}$ is —CH$_2$CH$_2$S(O)$_2$CH$_3$, and the combination of $R^{2a}$, $R^{2b}$ and $R^{2c}$ for a compound corresponds in each case to one row of Table A Table 18
Compounds of the formula Ia.1 in which $R^{61}$ is —CH$_2$CH$_2$SCH$_2$CH$_3$, and the combination of $R^{2a}$, $R^{2b}$ and $R^{2c}$ for a compound corresponds in each case to one row of Table A Table 19
Compounds of the formula Ia.1 in which $R^{61}$ is —CH$_2$CH$_2$S(O)CH$_2$CH$_3$, and the combination of $R^{2a}$, $R^{2b}$ and $R^{2c}$ for a compound corresponds in each case to one row of Table A Table 20

Compounds of the formula Ia.1 in which $R^{61}$ is —CH$_2$CH$_2$S(O)$_2$CH$_2$CH$_3$, and the combination of $R^{2a}$, $R^{2b}$ and $R^{2c}$ for a compound corresponds in each case to one row of Table A Table 21

Compounds of the formula Ia.1 in which $R^{61}$ is —CH$_2$CH$_2$SCF$_3$, and the combination of $R^{2a}$, $R^{2b}$ and $R^{2c}$ for a compound corresponds in each case to one row of Table A Table 22

Compounds of the formula Ia.1 in which $R^{61}$ is —CH$_2$CH$_2$S(O)CF$_3$, and the combination of $R^{2a}$, $R^{2b}$ and $R^{2c}$ for a compound corresponds in each case to one row of Table A Table 23

Compounds of the formula Ia.1 in which $R^{61}$ is CH$_2$CHF$_2$, and the combination of $R^{2a}$, $R^{2b}$ and $R^{2c}$ for a compound corresponds in each case to one row of Table A Table 24

Compounds of the formula Ia.1 in which $R^{61}$ is CH$_2$CF$_3$, and the combination of $R^{2a}$, $R^{2b}$ and $R^{2c}$ for a compound corresponds in each case to one row of Table A Table 25

Compounds of the formula Ia.1 in which $R^{61}$ is CH$_2$CH$_2$CF$_3$, and the combination of $R^{2a}$, $R^{2b}$ and $R^{2c}$ for a compound corresponds in each case to one row of Table A Table 26

Compounds of the formula Ia.1 in which $R^{61}$ is CH$_2$CH$_2$CHF$_2$, and the combination of $R^{2a}$, $R^{2b}$ and $R^{2c}$ for a compound corresponds in each case to one row of Table A Table 27

Compounds of the formula Ia.1 in which $R^{61}$ is cyclopropyl, and the combination of $R^{2a}$, $R^{2b}$ and $R^{2c}$ for a compound corresponds in each case to one row of Table A Table 28

Compounds of the formula Ia.1 in which $R^{61}$ is 1-cyano-cyclopropyl, and the combination of $R^{2a}$, $R^{2b}$ and $R^{2c}$ for a compound corresponds in each case to one row of Table A Table 29

Compounds of the formula Ia.1 in which $R^{61}$ is 2-fluorocyclopropyl, and the combination of $R^{2a}$, $R^{2b}$ and $R^{2c}$ for a compound corresponds in each case to one row of Table A Table 30

Compounds of the formula Ia.1 in which $R^{61}$ is 2,2-difluorocyclopropyl, and the combination of $R^{2a}$, $R^{2b}$ and $R^{2c}$ for a compound corresponds in each case to one row of Table A Table 31

Compounds of the formula Ia.1 in which $R^{61}$ is cyclobutyl, and the combination of $R^{2a}$, $R^{2b}$ and $R^{2c}$ for a compound corresponds in each case to one row of Table A Table 32

Compounds of the formula Ia.1 in which $R^{61}$ is 1-cyano-cyclobutyl, and the combination of $R^{2a}$, $R^{2b}$ and $R^{2c}$ for a compound corresponds in each case to one row of Table A Table 33

Compounds of the formula Ia.1 in which $R^{61}$ is 3,3-difluorocyclobutyl, and the combination of $R^{2a}$, $R^{2b}$ and $R^{2c}$ for a compound corresponds in each case to one row of Table A Table 34

Compounds of the formula Ia.1 in which $R^{61}$ is cyclopentyl, and the combination of $R^{2a}$, $R^{2b}$ and $R^{2c}$ for a compound corresponds in each case to one row of Table A Table 35

Compounds of the formula Ia.1 in which $R^{61}$ is 1-cyano-cyclopentyl, and the combination of $R^{2a}$, $R^{2b}$ and $R^{2c}$ for a compound corresponds in each case to one row of Table A Table 36

Compounds of the formula Ia.1 in which $R^{61}$ is cyclohexyl, and the combination of $R^{2a}$, $R^{2b}$ and $R^{2c}$ for a compound corresponds in each case to one row of Table A Table 37

Compounds of the formula Ia.1 in which $R^{61}$ is 1-cyano-cyclohexyl, and the combination of $R^{2a}$, $R^{2b}$ and $R^{2c}$ for a compound corresponds in each case to one row of Table A Table 38

Compounds of the formula Ia.1 in which $R^{61}$ is —CH$_2$-cyclopropyl, and the combination of $R^{2a}$, $R^{2b}$ and $R^{2c}$ for a compound corresponds in each case to one row of Table A Table 39

Compounds of the formula Ia.1 in which $R^{61}$ is —CH$_2$-(1-cyano-cyclopropyl), and the combination of $R^{2a}$, $R^{2b}$ and $R^{2c}$ for a compound corresponds in each case to one row of Table A Table 40

Compounds of the formula Ia.1 in which $R^{61}$ is —CH$_2$-(1-fluoro-cyclopropyl), and the combination of $R^{2a}$, $R^{2b}$ and $R^{2c}$ for a compound corresponds in each case to one row of Table A Table 41

Compounds of the formula Ia.1 in which $R^{61}$ is —CH$_2$-(1-trifluoromethyl-cyclopropyl), and the combination of $R^{2a}$, $R^{2b}$ and $R^{2c}$ for a compound corresponds in each case to one row of Table A Table 42

Compounds of the formula Ia.1 in which $R^{61}$ is —CH$_2$-(1-difluoromethyl-cyclopropyl), and the combination of $R^{2a}$, $R^{2b}$ and $R^{2c}$ for a compound corresponds in each case to one row of Table A Table 43

Compounds of the formula Ia.1 in which $R^{61}$ is —CH$_2$-(2,2-difluorocyclopropyl), and the combination of $R^{2a}$, $R^{2b}$ and $R^{2c}$ for a compound corresponds in each case to one row of Table A Table 44

Compounds of the formula Ia.1 in which $R^{61}$ is —CH$_2$-(2,2-dichlorocyclopropyl), and the combination of $R^{2a}$, $R^{2b}$ and $R^{2c}$ for a compound corresponds in each case to one row of Table A Table 45

Compounds of the formula Ia.1 in which $R^{61}$ is —CH$_2$-(2,2-dibromocyclopropyl), and the combination of $R^{2a}$, $R^{2b}$ and $R^{2c}$ for a compound corresponds in each case to one row of Table A Table 46

Compounds of the formula Ia.1 in which $R^{61}$ is —CH$_2$-cyclobutyl, and the combination of $R^{2a}$, $R^{2b}$ and $R^{2c}$ for a compound corresponds in each case to one row of Table A Table 47

Compounds of the formula Ia.1 in which $R^{61}$ is —CH$_2$-(1-cyano-cyclobutyl), and the combination of $R^{2a}$, $R^{2b}$ and $R^{2c}$ for a compound corresponds in each case to one row of Table A Table 48

Compounds of the formula Ia.1 in which $R^{61}$ is —CH$_2$-(1-fluoro-cyclobutyl), and the combination of $R^{2a}$, $R^{2b}$ and $R^{2c}$ for a compound corresponds in each case to one row of Table A Table 49
Compounds of the formula Ia.1 in which $R^{61}$ is —$CH_2$-(2,2-difluorocyclobutyl), and the combination of $R^{2a}$, $R^{2b}$ and $R^{2c}$ for a compound corresponds in each case to one row of Table A Table 50
Compounds of the formula Ia.1 in which $R^{61}$ is —$CH_2$-(3,3-difluorocyclobutyl), and the combination of $R^{2a}$, $R^{2b}$ and $R^{2c}$ for a compound corresponds in each case to one row of Table A Table 51
Compounds of the formula Ia.1 in which $R^{61}$ is —$CH_2$-(2,2,3,3-tetrafluorocyclobutyl), and the combination of $R^{2a}$, $R^{2b}$ and $R^{2c}$ for a compound corresponds in each case to one row of Table A Table 52
Compounds of the formula Ia.1 in which $R^{61}$ is —$CH_2$-cyclopentyl, and the combination of $R^{2a}$, $R^{2b}$ and $R^{2c}$ for a compound corresponds in each case to one row of Table A Table 53
Compounds of the formula Ia.1 in which $R^{61}$ is —$CH_2$-(-1-fluoro-cyclopentyl), and the combination of $R^{2a}$, $R^{2b}$ and $R^{2c}$ for a compound corresponds in each case to one row of Table A Table 54
Compounds of the formula Ia.1 in which $R^{61}$ is —$CH_2$-(1-cyano-cyclopentyl), and the combination of $R^{2a}$, $R^{2b}$ and $R^{2c}$ for a compound corresponds in each case to one row of Table A Table 55
Compounds of the formula Ia.1 in which $R^{61}$ is —$CH_2$-(2,2-difluorocyclopentyl), and the combination of $R^{2a}$, $R^{2b}$ and $R^{2c}$ for a compound corresponds in each case to one row of Table A Table 56
Compounds of the formula Ia.1 in which $R^{61}$ is —$CH_2$-(3,3-difluorocyclopentyl), and the combination of $R^{2a}$, $R^{2b}$ and $R^{2c}$ for a compound corresponds in each case to one row of Table A Table 57
Compounds of the formula Ia.1 in which $R^{61}$ is —$CH_2$-cyclohexyl, and the combination of $R^{2a}$, $R^{2b}$ and $R^{2c}$ for a compound corresponds in each case to one row of Table A Table 58
Compounds of the formula Ia.1 in which $R^{61}$ is —$CH_2$-(1-fluorocyclohexyl), and the combination of $R^{2a}$, $R^{2b}$ and $R^{2c}$ for a compound corresponds in each case to one row of Table A Table 59
Compounds of the formula Ia.1 in which $R^{61}$ is —$CH_2$-(1-cyanocyclohexyl), and the combination of $R^{2a}$, $R^{2b}$ and $R^{2c}$ for a compound corresponds in each case to one row of Table A Table 60
Compounds of the formula Ia.1 in which $R^{61}$ is thietan-3-yl, and the combination of $R^{2a}$, $R^{2b}$ and $R^{2c}$ for a compound corresponds in each case to one row of Table A Table 61
Compounds of the formula Ia.1 in which $R^{61}$ is 1-oxo-thietan-3-yl, and the combination of $R^{2a}$, $R^{2b}$ and $R^{2c}$ for a compound corresponds in each case to one row of Table A Table 62
Compounds of the formula Ia.1 in which $R^{61}$ is 1,1-dioxo-thietan-3-yl, and the combination of $R^{2a}$, $R^{2b}$ and $R^{2c}$ for a compound corresponds in each case to one row of Table A Table 63
Compounds of the formula Ia.1 in which $R^{61}$ is —$CH_2$-thietan-3-yl, and the combination of $R^{2a}$, $R^{2b}$ and $R^{2c}$ for a compound corresponds in each case to one row of Table A Table 64
Compounds of the formula Ia.1 in which $R^{61}$ is —$CH_2$-(1-oxo-thietan-3-yl), and the combination of $R^{2a}$, $R^{2b}$ and $R^{2c}$ for a compound corresponds in each case to one row of Table A Table 65
Compounds of the formula Ia.1 in which $R^{61}$ is —$CH_2$-(1,1-dioxo-thietan-3-yl), and the combination of $R^{2a}$, $R^{2b}$ and $R^{2c}$ for a compound corresponds in each case to one row of Table A Table 66
Compounds of the formula Ia.1 in which $R^{61}$ is —$CH_2$-thietan-2-yl, and the combination of $R^{2a}$, $R^{2b}$ and $R^{2c}$ for a compound corresponds in each case to one row of Table A Table 67
Compounds of the formula Ia.1 in which $R^{61}$ is —$CH_2$-(1-oxo-thietan-2-yl), and the combination of $R^{2a}$, $R^{2b}$ and $R^{2c}$ for a compound corresponds in each case to one row of Table A Table 68
Compounds of the formula Ia.1 in which $R^{61}$ is —$CH_2$-(1,1-dioxo-thietan-2-yl), and the combination of $R^{2a}$, $R^{2b}$ and $R^{2c}$ for a compound corresponds in each case to one row of Table A Table 69
Compounds of the formula Ia.1 in which $R^{61}$ is tetrahydrothiophen-3-yl, and the combination of $R^{2a}$, $R^{2b}$ and $R^{2c}$ for a compound corresponds in each case to one row of Table A Table 70
Compounds of the formula Ia.1 in which $R^{61}$ is 1-oxo-tetrahydrothiophen-3-yl, and the combination of $R^{2a}$, $R^{2b}$ and $R^{2c}$ for a compound corresponds in each case to one row of Table A Table 71
Compounds of the formula Ia.1 in which $R^{61}$ is 1,1-dioxo-tetrahydrothiophen-3-yl, and the combination of $R^{2a}$, $R^{2b}$ and $R^{2c}$ for a compound corresponds in each case to one row of Table A Table 72
Compounds of the formula Ia.1 in which $R^{61}$ is phenyl, and the combination of $R^{2a}$, $R^{2b}$ and $R^{2c}$ for a compound corresponds in each case to one row of Table A Table 73
Compounds of the formula Ia.1 in which $R^{61}$ is 2-fluorophenyl, and the combination of $R^{2a}$, $R^{2b}$ and $R^{2c}$ for a compound corresponds in each case to one row of Table A Table 74
Compounds of the formula Ia.1 in which $R^{61}$ is pyridin-2-yl, and the combination of $R^{2a}$, $R^{2b}$ and $R^{2c}$ for a compound corresponds in each case to one row of Table A Table 75
Compounds of the formula Ia.1 in which $R^{61}$ is pyridin-3-yl, and the combination of $R^{2a}$, $R^{2b}$ and $R^{2c}$ for a compound corresponds in each case to one row of Table A Table 76
Compounds of the formula Ia.1 in which $R^{61}$ is pyridin-4-yl, and the combination of $R^{2a}$, $R^{2b}$ and $R^{2c}$ for a compound corresponds in each case to one row of Table A Table 77
Compounds of the formula Ia.1 in which $R^{61}$ is pyrimidin-2-yl, and the combination of $R^{2a}$, $R^{2b}$ and $R^{2c}$ for a compound corresponds in each case to one row of Table A Table 78
Compounds of the formula Ia.1 in which $R^{61}$ is pyrimidin-4-yl, and the combination of $R^{2a}$, $R^{2b}$ and $R^{2c}$ for a compound corresponds in each case to one row of Table A Table 79
Compounds of the formula Ia.1 in which $R^{61}$ is pyrimidin-5-yl, and the combination of $R^{2a}$, $R^{2b}$ and $R^{2c}$ for a compound corresponds in each case to one row of Table A Table 80
Compounds of the formula Ia.1 in which $R^{61}$ is oxetan-3-yl, and the combination of $R^{2a}$, $R^{2b}$ and $R^{2c}$ for a compound corresponds in each case to one row of Table A Table 81
Compounds of the formula Ia.1 in which $R^{61}$ is tetrahydrofuran-2-yl, and the combination of $R^{2a}$, $R^{2b}$ and $R^{2c}$ for a compound corresponds in each case to one row of Table A Table 82
Compounds of the formula Ia.1 in which $R^{61}$ is tetrahydrofuran-3-yl, and the combination of $R^{2a}$, $R^{2b}$ and $R^{2c}$ for a compound corresponds in each case to one row of Table A Table 83
Compounds of the formula Ia.1 in which $R^{61}$ is 2-oxo-tetrahydrofuran-3-yl, and the combination of $R^{2a}$, $R^{2b}$ and $R^{2c}$ for a compound corresponds in each case to one row of Table A Table 84
Compounds of the formula Ia.1 in which $R^{61}$ is 1-ethyl-2-oxo-pyrrolidin-3-yl, and the combination of $R^{2a}$, $R^{2b}$ and $R^{2c}$ for a compound corresponds in each case to one row of Table A Table 85
Compounds of the formula Ia.1 in which $R^{61}$ is 2-oxopyrrolidin-3-yl, and the combination of $R^{2a}$, $R^{2b}$ and $R^{2c}$ for a compound corresponds in each case to one row of Table A Table 86
Compounds of the formula Ia.1 in which $R^{61}$ is 1-methyl-2-oxopyrrolidin-3-yl, and the combination of $R^{2a}$, $R^{2b}$ and $R^{2c}$ for a compound corresponds in each case to one row of Table A Table 87
Compounds of the formula Ia.1 in which $R^{61}$ is 2-oxo-1-(2,2,2-trifluoroethyl)-pyrrolidin-3-yl, and the combination of $R^{2a}$, $R^{2b}$ and $R^{2c}$ for a compound corresponds in each case to one row of Table A Table 88
Compounds of the formula Ia.1 in which $R^{61}$ is 3-oxo-isoxazolidin-4-yl, and the combination of $R^{2a}$, $R^{2b}$ and $R^{2c}$ for a compound corresponds in each case to one row of Table A Table 89
Compounds of the formula Ia.1 in which $R^{61}$ is 2-methyl-3-oxo-isoxazolidin-4-yl, and the combination of $R^{2a}$, $R^{2b}$ and $R^{2c}$ for a compound corresponds in each case to one row of Table A Table 90
Compounds of the formula Ia.1 in which $R^{61}$ is 2-ethyl-3-oxo-isoxazolidin-4-yl, and the combination of $R^{2a}$, $R^{2b}$ and $R^{2c}$ for a compound corresponds in each case to one row of Table A Table 91
Compounds of the formula Ia.1 in which $R^{61}$ is 2-propyl-3-oxo-isoxazolidin-4-yl, and the combination of $R^{2a}$, $R^{2b}$ and $R^{2c}$ for a compound corresponds in each case to one row of Table A Table 92
Compounds of the formula Ia.1 in which $R^{61}$ is 2-(2-fluoroethyl)-3-oxo-isoxazolidin-4-yl, and the combination of $R^{2a}$, $R^{2b}$ and $R^{2c}$ for a compound corresponds in each case to one row of Table A Table 93
Compounds of the formula Ia.1 in which $R^{61}$ is 2-(2,2-difluoroethyl)-3-oxo-isoxazolidin-4-yl, and the combination of $R^{2a}$, $R^{2b}$ and $R^{2c}$ for a compound corresponds in each case to one row of Table A Table 94
Compounds of the formula Ia.1 in which $R^{61}$ is 2-(2,2,2-trifluoroethyl)-3-oxo-isoxazolidin-4-yl, and the combination of $R^{2a}$, $R^{2b}$ and $R^{2c}$ for a compound corresponds in each case to one row of Table A Table 95
Compounds of the formula Ia.1 in which $R^{61}$ is —NH-pyridin-2-yl, and the combination of $R^{2a}$, $R^{2b}$ and $R^{2c}$ for a compound corresponds in each case to one row of Table A Table 96
Compounds of the formula Ia.1 in which $R^{61}$ is —N(CH$_3$)-pyridin-2-yl, and the combination of $R^{2a}$, $R^{2b}$ and $R^{2c}$ for a compound corresponds in each case to one row of Table A Table 97
Compounds of the formula Ia.1 in which $R^{61}$ is —NH-pyrimidin-2-yl, and the combination of $R^{2a}$, $R^{2b}$ and $R^{2c}$ for a compound corresponds in each case to one row of Table A Table 98
Compounds of the formula Ia.1 in which $R^{61}$ is —NH-pyrimidin-4-yl, and the combination of $R^{2a}$, $R^{2b}$ and $R^{2c}$ for a compound corresponds in each case to one row of Table A Table 99
Compounds of the formula Ia.1 in which $R^{61}$ is —N(CH$_3$)-pyrimidin-2-yl, and the combination of $R^{2a}$, $R^{2b}$ and $R^{2c}$ for a compound corresponds in each case to one row of Table A Table 100
Compounds of the formula Ia.1 in which $R^{61}$ is —CH$_2$—CONH$_2$, and the combination of $R^{2a}$, $R^{2b}$ and $R^{2c}$ for a compound corresponds in each case to one row of Table A Table 101
Compounds of the formula Ia.1 in which $R^{61}$ is —CH$_2$—CONH—CH$_3$, and the combination of $R^{2a}$, $R^{2b}$ and $R^{2c}$ for a compound corresponds in each case to one row of Table A Table 102
Compounds of the formula Ia.1 in which $R^{61}$ is —CH$_2$—CONH—CH$_2$CH$_3$, and the combination of $R^{2a}$, $R^{2b}$ and $R^{2c}$ for a compound corresponds in each case to one row of Table A Table 103
Compounds of the formula Ia.1 in which $R^{61}$ is —CH$_2$—CONH—CH$_2$CH$_2$CH$_3$, and the combination of $R^{2a}$, $R^{2b}$ and $R^{2c}$ for a compound corresponds in each case to one row of Table A Table 104
Compounds of the formula Ia.1 in which $R^{61}$ is —CH$_2$—CONH—CH$_2$CH$_2$F, and the combination of $R^{2a}$, $R^{2b}$ and $R^{2c}$ for a compound corresponds in each case to one row of Table A Table 105
Compounds of the formula Ia.1 in which $R^{61}$ is —CH$_2$—CONH—CH$_2$CHF$_2$, and the combination of $R^{2a}$, $R^{2b}$ and $R^{2c}$ for a compound corresponds in each case to one row of Table A Table 106
Compounds of the formula Ia.1 in which $R^{61}$ is —CH$_2$—CONH—CH$_2$CF$_3$, and the combination of $R^{2a}$, $R^{2b}$ and $R^{2c}$ for a compound corresponds in each case to one row of Table A Table 107
Compounds of the formula Ia.1 in which $R^{61}$ is —CH$_2$—CONH-cyclopropyl, and the combination of $R^{2a}$, $R^{2b}$ and $R^{2c}$ for a compound corresponds in each case to one row of Table A Table 108
Compounds of the formula Ia.1 in which $R^{61}$ is —CH$_2$—CONH—CH$_2$CN, and the combination of $R^{2a}$, $R^{2b}$ and $R^{2c}$ for a compound corresponds in each case to one row of Table A Table 109
Compounds of the formula Ia.1 in which $R^{61}$ is —CH$_2$—CONH—CH$_2$CH=CH$_2$, and the combination of $R^{2a}$, $R^{2b}$ and $R^{2c}$ for a compound corresponds in each case to one row of Table A Table 110
Compounds of the formula Ia.1 in which $R^{61}$ is —CH$_2$—CONH—CH$_2$C≡CH, and the combination of $R^{2a}$, $R^{2b}$ and $R^{2c}$ for a compound corresponds in each case to one row of Table A Table 111
Compounds of the formula Ia.1 in which $R^{61}$ is —CH$_2$—CONH—CH$_2$-cyclopropyl, and the combination of $R^{2a}$, $R^{2b}$ and $R^{2c}$ for a compound corresponds in each case to one row of Table A Table 112
Compounds of the formula Ia.1 in which $R^{61}$ is —CH$_2$—CONH—CH$_2$-(1-cyano-cyclopropyl), and the combination of $R^{2a}$, $R^{2b}$ and $R^{2c}$ for a compound corresponds in each case to one row of Table A Table 113
Compounds of the formula Ia.1 in which $R^{61}$ is benzyl, and the combination of $R^{2a}$, $R^{2b}$ and $R^{2c}$ for a compound corresponds in each case to one row of Table A Table 114
Compounds of the formula Ia.1 in which $R^{61}$ is —CH$_2$-(pyridin-2-yl), and the combination of $R^{2a}$, $R^{2b}$ and $R^{2c}$ for a compound corresponds in each case to one row of Table A Table 115
Compounds of the formula Ia.1 in which $R^{61}$ is —CH$_2$-(pyridin-3-yl), and the combination of $R^{2a}$, $R^{2b}$ and $R^{2c}$ for a compound corresponds in each case to one row of Table A Table 116
Compounds of the formula Ia.1 in which $R^{61}$ is —CH$_2$-(pyridin-4-yl), and the combination of $R^{2a}$, $R^{2b}$ and $R^{2c}$ for a compound corresponds in each case to one row of Table A Table 117
Compounds of the formula Ia.1 in which $R^{61}$ is —CH$_2$-(pyrimidin-2-yl), and the combination of $R^{2a}$, $R^{2b}$ and $R^{2c}$ for a compound corresponds in each case to one row of Table A Table 118
Compounds of the formula Ia.1 in which $R^{61}$ is —CH$_2$-(pyrimidin-4-yl), and the combination of $R^{2a}$, $R^{2b}$ and $R^{2c}$ for a compound corresponds in each case to one row of Table A Table 119
Compounds of the formula Ia.1 in which $R^{61}$ is —CH$_2$-(pyrimidin-5-yl), and the combination of $R^{2a}$, $R^{2b}$ and $R^{2c}$ for a compound corresponds in each case to one row of Table A Table 120
Compounds of the formula Ia.1 in which $R^{61}$ is —CH$_2$-(pyridazin-3-yl), and the combination of $R^{2a}$, $R^{2b}$ and $R^{2c}$ for a compound corresponds in each case to one row of Table A Table 121
Compounds of the formula Ia.1 in which $R^{61}$ is —CH$_2$-(pyridazin-4-yl), and the combination of $R^{2a}$, $R^{2b}$ and $R^{2c}$ for a compound corresponds in each case to one row of Table A Table 122
Compounds of the formula Ia.1 in which $R^{61}$ is —CH$_2$-(pyrazin-2-yl), and the combination of $R^{2a}$, $R^{2b}$ and $R^{2c}$ for a compound corresponds in each case to one row of Table A Table 123
Compounds of the formula Ia.1 in which $R^{61}$ is —CH$_2$-(1-methylpyrazol-3-yl), and the combination of $R^{2a}$, $R^{2b}$ and $R^{2c}$ for a compound corresponds in each case to one row of Table A Table 124
Compounds of the formula Ia.1 in which $R^{61}$ is —CH$_2$-(thiazol-2-yl), and the combination of $R^{2a}$, $R^{2b}$ and $R^{2c}$ for a compound corresponds in each case to one row of Table A Table 125
Compounds of the formula Ia.1 in which $R^{61}$ is —CH$_2$-(thiazol-4-yl), and the combination of $R^{2a}$, $R^{2b}$ and $R^{2c}$ for a compound corresponds in each case to one row of Table A Table 126
Compounds of the formula Ia.1 in which $R^{61}$ is —CH$_2$-(1,3,4-thiadiazol-2-yl), and the combination of $R^{2a}$, $R^{2b}$ and $R^{2c}$ for a compound corresponds in each case to one row of Table A Table 127
Compounds of the formula Ia.1 in which $R^{61}$ is —CH$_2$-(1,2,4-thiadiazol-2-yl), and the combination of $R^{2a}$, $R^{2b}$ and $R^{2c}$ for a compound corresponds in each case to one row of Table A Table 128
Compounds of the formula Ia.1 in which $R^{61}$ is —CH$_2$-(isothiazol-3-yl), and the combination of $R^{2a}$, $R^{2b}$ and $R^{2c}$ for a compound corresponds in each case to one row of Table A Table 129
Compounds of the formula Ia.1 in which $R^{61}$ is —CH$_2$-(oxazol-2-yl), and the combination of $R^{2a}$, $R^{2b}$ and $R^{2c}$ for a compound corresponds in each case to one row of Table A Table 130
Compounds of the formula Ia.1 in which $R^{61}$ is —CH$_2$-(oxazol-4-yl), and the combination of $R^{2a}$, $R^{2b}$ and $R^{2c}$ for a compound corresponds in each case to one row of Table A Table 131
Compounds of the formula Ia.1 in which $R^{61}$ is —CH$_2$-(1,3,4-oxadiazol-2-yl), and the combination of $R^{2a}$, $R^{2b}$ and $R^{2c}$ for a compound corresponds in each case to one row of Table A Table 132
Compounds of the formula Ia.1 in which $R^{61}$ is —CH$_2$-(1,2,4-oxadiazol-3-yl), and the combination of $R^{2a}$, $R^{2b}$ and $R^{2c}$ for a compound corresponds in each case to one row of Table A Table 133
Compounds of the formula Ia.1 in which $R^{61}$ is —CH$_2$-(isoxazol-3-yl), and the combination of $R^{2a}$, $R^{2b}$ and $R^{2c}$ for a compound corresponds in each case to one row of Table A Table 134
Compounds of the formula Ia.1 in which $R^{61}$ is —CH$_2$-(1-methyl-1,2,4-triazol-3-yl), and the combination of $R^{2a}$, $R^{2b}$ and $R^{2c}$ for a compound corresponds in each case to one row of Table A Table 135
Compounds of the formula Ia.1 in which $R^{61}$ is —$CH_2$-(4-methyl-1,2,4-triazol-3-yl), and the combination of $R^{2a}$, $R^{2b}$ and $R^{2c}$ for a compound corresponds in each case to one row of Table A Table 136
Compounds of the formula Ia.1 in which $R^{61}$ is —$CH_2$-(tetrahydrofuran-2-yl), and the combination of $R^{2a}$, $R^{2b}$ and $R^{2c}$ for a compound corresponds in each case to one row of Table A Table 137
Compounds of the formula Ia.1 in which $R^{61}$ is —$CH_2$-(tetrahydrofuran-3-yl), and the combination of $R^{2a}$, $R^{2b}$ and $R^{2c}$ for a compound corresponds in each case to one row of Table A Table 138
Compounds of the formula Ia.1 in which $R^{61}$ is —$CH_2$-(1,3-dioxolan-2-yl), and the combination of $R^{2a}$, $R^{2b}$ and $R^{2c}$ for a compound corresponds in each case to one row of Table A Table 139
Compounds of the formula Ia.1 in which $R^{61}$ is —$CH_2CH_2$-(1,3-dioxolan-2-yl), and the combination of $R^{2a}$, $R^{2b}$ and $R^{2c}$ for a compound corresponds in each case to one row of Table A Table 140
Compounds of the formula Ia.1 in which $R^{61}$ is —$CH_2$-(1,3-dioxan-2-yl), and the combination of $R^{2a}$, $R^{2b}$ and $R^{2c}$ for a compound corresponds in each case to one row of Table A Table 141
Compounds of the formula Ia.1 in which $R^{61}$ is —NHCO—NH—$CH_3$, and the combination of $R^{2a}$, $R^{2b}$ and $R^{2c}$ for a compound corresponds in each case to one row of Table A Table 142
Compounds of the formula Ia.1 in which $R^{61}$ is —NHCO—NH—$CH_2CH_3$, and the combination of $R^{2a}$, $R^{2b}$ and $R^{2c}$ for a compound corresponds in each case to one row of Table A Table 143
Compounds of the formula Ia.1 in which $R^{61}$ is —NHCO—NH—$CH_2CF_3$, and the combination of $R^{2a}$, $R^{2b}$ and $R^{2c}$ for a compound corresponds in each case to one row of Table A Table 144
Compounds of the formula Ia.1 in which $R^{61}$ is —NHCO—NH—$CH_2CHF_2$, and the combination of $R^{2a}$, $R^{2b}$ and $R^{2c}$ for a compound corresponds in each case to one row of Table A Table 145
Compounds of the formula Ia.1 in which $R^{61}$ is —NHCO—NH—$CH_2CN$, and the combination of $R^{2a}$, $R^{2b}$ and $R^{2c}$ for a compound corresponds in each case to one row of Table A Table 146
Compounds of the formula Ia.1 in which $R^{61}$ is —NHCO—NH—$CH_2$—CH=$CH_2$, and the combination of $R^{2a}$, $R^{2b}$ and $R^{2c}$ for a compound corresponds in each case to one row of Table A Table 147
Compounds of the formula Ia.1 in which $R^{61}$ is —NHCO—NH—$CH_2$—C≡CH, and the combination of $R^{2a}$, $R^{2b}$ and $R^{2c}$ for a compound corresponds in each case to one row of Table A Table 148
Compounds of the formula Ia.1 in which $R^{61}$ is —NHCO—NH-cyclopropyl, and the combination of $R^{2a}$, $R^{2b}$ and $R^{2c}$ for a compound corresponds in each case to one row of Table A Table 149
Compounds of the formula Ia.1 in which $R^{61}$ is —NHCO—NH—$CH_2$-cyclopropyl, and the combination of $R^{2a}$, $R^{2b}$ and $R^{2c}$ for a compound corresponds in each case to one row of Table A Table 150
Compounds of the formula Ia.1 in which $R^{61}$ is —NHCO—NH—$CH_2$-(1-cyanocyclopropyl), and the combination of $R^{2a}$, $R^{2b}$ and $R^{2c}$ for a compound corresponds in each case to one row of Table A Table 151
Compounds of the formula Ia.1 in which $R^{61}$ is —CH=$NOCH_3$, and the combination of $R^{2a}$, $R^{2b}$ and $R^{2c}$ for a compound corresponds in each case to one row of Table A Table 152
Compounds of the formula Ia.1 in which $R^{61}$ is —CH=$NOCH_2CH_3$, and the combination of $R^{2a}$, $R^{2b}$ and $R^{2c}$ for a compound corresponds in each case to one row of Table A Table 153
Compounds of the formula Ia.1 in which $R^{61}$ is —CH=$NOCH_2CF_3$, and the combination of $R^{2a}$, $R^{2b}$ and $R^{2c}$ for a compound corresponds in each case to one row of Table A Table 154
Compounds of the formula Ia.1 in which $R^{61}$ is —CH=$NOCH_2$CH=$CH_2$, and the combination of $R^{2a}$, $R^{2b}$ and $R^{2c}$ for a compound corresponds in each case to one row of Table A Table 155
Compounds of the formula Ia.1 in which $R^{61}$ is —CH=$NOCH_2$C≡CH, and the combination of $R^{2a}$, $R^{2b}$ and $R^{2c}$ for a compound corresponds in each case to one row of Table A Tables 156 to 310
Compounds of the formula Ia.2 in which $R^{61}$ is as defined in tables 1 to 155, and the combination of $R^{2a}$, $R^{2b}$ and $R^{2c}$ for a compound corresponds in each case to one row of Table A Tables 311 to 465
Compounds of the formula Ia.3 in which $R^{61}$ is as defined in tables 1 to 155, and the combination of $R^{2a}$, $R^{2b}$ and $R^{2c}$ for a compound corresponds in each case to one row of Table A Tables 466 to 620
Compounds of the formula Ia.4 in which $R^{61}$ is as defined in tables 1 to 155, and the combination of $R^{2a}$, $R^{2b}$ and $R^{2c}$ for a compound corresponds in each case to one row of Table A Tables 621 to 775
Compounds of the formula Ia.5 in which $R^{61}$ is as defined in tables 1 to 155, and the combination of $R^{2a}$, $R^{2b}$ and $R^{2c}$ for a compound corresponds in each case to one row of Table A Tables 776 to 930
Compounds of the formula Ia.6 in which $R^{61}$ is as defined in tables 1 to 155, and the combination of $R^{2a}$, $R^{2b}$ and $R^{2c}$ for a compound corresponds in each case to one row of Table A Tables 931 to 1085
Compounds of the formula Ia.7 in which $R^{61}$ is as defined in tables 1 to 155, and the combination of $R^{2a}$, $R^{2b}$ and $R^{2c}$ for a compound corresponds in each case to one row of Table A Tables 1086 to 1240
Compounds of the formula Ia.8 in which $R^{61}$ is as defined in tables 1 to 155, and the combination of $R^{2a}$, $R^{2b}$ and $R^{2c}$ for a compound corresponds in each case to one row of Table A Tables 1241 to 1395
Compounds of the formula Ia.9 in which $R^{61}$ is as defined in tables 1 to 155, and the combination of $R^{2a}$, $R^{2b}$ and $R^{2c}$ for a compound corresponds in each case to one row of Table A Tables 1396 to 1550
Compounds of the formula Ia.10 in which $R^{61}$ is as defined in tables 1 to 155, and the combination of $R^{2a}$, $R^{2b}$ and $R^{2c}$ for a compound corresponds in each case to one row of Table A Tables 1551 to 1705
Compounds of the formula Ia.11 in which $R^{61}$ is as defined in tables 1 to 155, and the combination of $R^{2a}$, $R^{2b}$ and $R^{2c}$ for a compound corresponds in each case to one row of Table A Tables 1706 to 1860
Compounds of the formula Ia.12 in which $R^{61}$ is as defined in tables 1 to 155, and the combination of $R^{2a}$, $R^{2b}$ and $R^{2c}$ for a compound corresponds in each case to one row of Table A Tables 1861 to 2015
Compounds of the formula Ia.13 in which $R^{61}$ is as defined in tables 1 to 155, and the combination of $R^{2a}$, $R^{2b}$ and $R^{2c}$ for a compound corresponds in each case to one row of Table A Tables 2016 to 2170
Compounds of the formula Ia.14 in which $R^{61}$ is as defined in tables 1 to 155, and the combination of $R^{2a}$, $R^{2b}$ and $R^{2c}$ for a compound corresponds in each case to one row of Table A Tables 2171 to 2325
Compounds of the formula Ia.15 in which $R^{61}$ is as defined in tables 1 to 155, and the combination of $R^{2a}$, $R^{2b}$ and $R^{2c}$ for a compound corresponds in each case to one row of Table A Tables 2326 to 2480
Compounds of the formula Ia.16 in which $R^{61}$ is as defined in tables 1 to 155, and the combination of $R^{2a}$, $R^{2b}$ and $R^{2c}$ for a compound corresponds in each case to one row of Table A Tables 2481 to 2635
Compounds of the formula Ia.17 in which $R^{61}$ is as defined in tables 1 to 155, and the combination of $R^{2a}$, $R^{2b}$ and $R^{2c}$ for a compound corresponds in each case to one row of Table A Tables 2636 to 2790
Compounds of the formula Ia.18 in which $R^{61}$ is as defined in tables 1 to 155, and the combination of $R^{2a}$, $R^{2b}$ and $R^{2c}$ for a compound corresponds in each case to one row of Table A Tables 2791 to 2945
Compounds of the formula Ia.19 in which $R^{61}$ is as defined in tables 1 to 155, and the combination of $R^{2a}$, $R^{2b}$ and $R^{2c}$ for a compound corresponds in each case to one row of Table A Tables 2946 to 3100
Compounds of the formula Ia.20 in which $R^{61}$ is as defined in tables 1 to 155, and the combination of $R^{2a}$, $R^{2b}$ and $R^{2c}$ for a compound corresponds in each case to one row of Table A Table 3101
Compounds of the formula Ia.21 in which $R^{62}$ is methyl, and the combination of $R^{2a}$, $R^{2b}$ and $R^{2c}$ for a compound corresponds in each case to one row of Table A Table 3102
Compounds of the formula Ia.21 in which $R^{62}$ is ethyl, and the combination of $R^{2a}$, $R^{2b}$ and $R^{2c}$ for a compound corresponds in each case to one row of Table A Table 3103
Compounds of the formula Ia.21 in which $R^{62}$ is n-propyl, and the combination of $R^{2a}$, $R^{2b}$ and $R^{2c}$ for a compound corresponds in each case to one row of Table A Table 3104
Compounds of the formula Ia.21 in which $R^{62}$ is cyclpropyl, and the combination of $R^{2a}$, $R^{2b}$ and $R^{2c}$ for a compound corresponds in each case to one row of Table A Table 3105
Compounds of the formula Ia.21 in which $R^{62}$ is —$CH_2CF_3$, and the combination of $R^{2a}$, $R^{2b}$ and $R^{2c}$ for a compound corresponds in each case to one row of Table A Table 3106
Compounds of the formula Ia.21 in which $R^{62}$ is —$CH_2SCH_3$, and the combination of $R^{2a}$, $R^{2b}$ and $R^{2c}$ for a compound corresponds in each case to one row of Table A Table 3107
Compounds of the formula Ia.21 in which $R^{62}$ is —$CH_2SCH_2CH_3$, and the combination of $R^{2a}$, $R^{2b}$ and $R^{2c}$ for a compound corresponds in each case to one row of Table A Table 3108
Compounds of the formula Ia.21 in which $R^{62}$ is —$CH_2S(O)CH_3$, and the combination of $R^{2a}$, $R^{2b}$ and $R^{2c}$ for a compound corresponds in each case to one row of Table A Table 3109
Compounds of the formula Ia.21 in which $R^{62}$ is —$CH_2S(O)CH_2CH_3$, and the combination of $R^{2a}$, $R^{2b}$ and $R^{2c}$ for a compound corresponds in each case to one row of Table A Table 3110
Compounds of the formula Ia.21 in which $R^{62}$ is —$CH_2S(O)_2CH_3$, and the combination of $R^{2a}$, $R^{2b}$ and $R^{2c}$ for a compound corresponds in each case to one row of Table A Table 3111
Compounds of the formula Ia.21 in which $R^{62}$ is —$CH_2S(O)_2CH_2CH_3$, and the combination of $R^{2a}$, $R^{2b}$ and $R^{2c}$ for a compound corresponds in each case to one row of Table A Table 3112
Compounds of the formula Ia.21 in which $R^{62}$ is —$CH_2OCH_3$, and the combination of $R^{2a}$, $R^{2b}$ and $R^{2c}$ for a compound corresponds in each case to one row of Table A Table 3113
Compounds of the formula Ia.21 in which $R^{62}$ is —$CH_2CH_2OCH_3$, and the combination of $R^{2a}$, $R^{2b}$ and $R^{2c}$ for a compound corresponds in each case to one row of Table A Table 3114
Compounds of the formula Ia.21 in which $R^{62}$ is —$CH_2$-(2-tetrahydrofuranyl), and the combination of $R^{2a}$, $R^{2b}$ and $R^{2c}$ for a compound corresponds in each case to one row of Table A Table 3115

Compounds of the formula Ia.21 in which $R^{62}$ is —CH$_2$-(1,3-dioxolan-2-yl), and the combination of $R^{2a}$, $R^{2b}$ and $R^{2c}$ for a compound corresponds in each case to one row of Table A Tables 3116 to 3130

Compounds of the formula Ia.22 in which $R^{62}$ is as defined in tables 3101 to 3115, and the combination of $R^{2a}$, $R^{2b}$ and $R^{2c}$ for a compound corresponds in each case to one row of Table A Tables 3131 to 3145

Compounds of the formula Ia.23 in which $R^{62}$ is as defined in tables 3101 to 3115, and the combination of $R^{2a}$, $R^{2b}$ and $R^{2c}$ for a compound corresponds in each case to one row of Table A Tables 3146 to 3160

Compounds of the formula Ia.24 in which $R^{62}$ is as defined in tables 3101 to 3115, and the combination of $R^{2a}$, $R^{2b}$ and $R^{2c}$ for a compound corresponds in each case to one row of Table A Tables 3161 to 3175

Compounds of the formula Ia.25 in which $R^{62}$ is as defined in tables 3101 to 3115, and the combination of $R^{2a}$, $R^{2b}$ and $R^{2c}$ for a compound corresponds in each case to one row of Table A Tables 3176 to 3190

Compounds of the formula Ia.26 in which $R^{62}$ is as defined in tables 3101 to 3115, and the combination of $R^{2a}$, $R^{2b}$ and $R^{2c}$ for a compound corresponds in each case to one row of Table A Tables 3191 to 3205

Compounds of the formula Ia.27 in which $R^{62}$ is as defined in tables 3101 to 3115, and the combination of $R^{2a}$, $R^{2b}$ and $R^{2c}$ for a compound corresponds in each case to one row of Table A Tables 3206 to 3220

Compounds of the formula Ia.28 in which $R^{62}$ is as defined in tables 3101 to 3115, and the combination of $R^{2a}$, $R^{2b}$ and $R^{2c}$ for a compound corresponds in each case to one row of Table A Tables 3221 to 3235

Compounds of the formula Ia.29 in which $R^{62}$ is as defined in tables 3101 to 3115, and the combination of $R^{2a}$, $R^{2b}$ and $R^{2c}$ for a compound corresponds in each case to one row of Table A Tables 3236 to 3250

Compounds of the formula Ia.30 in which $R^{62}$ is as defined in tables 3101 to 3115, and the combination of $R^{2a}$, $R^{2b}$ and $R^{2c}$ for a compound corresponds in each case to one row of Table A Tables 3251 to 3265

Compounds of the formula Ia.31 in which $R^{62}$ is as defined in tables 3101 to 3115, and the combination of $R^{2a}$, $R^{2b}$ and $R^{2c}$ for a compound corresponds in each case to one row of Table A Tables 3266 to 3280

Compounds of the formula Ia.32 in which $R^{62}$ is as defined in tables 3101 to 3115, and the combination of $R^{2a}$, $R^{2b}$ and $R^{2c}$ for a compound corresponds in each case to one row of Table A Tables 3281 to 3295

Compounds of the formula Ia.33 in which $R^{62}$ is as defined in tables 3101 to 3115, and the combination of $R^{2a}$, $R^{2b}$ and $R^{2c}$ for a compound corresponds in each case to one row of Table A Tables 3296 to 3310

Compounds of the formula Ia.34 in which $R^{62}$ is as defined in tables 3101 to 3115, and the combination of $R^{2a}$, $R^{2b}$ and $R^{2c}$ for a compound corresponds in each case to one row of Table A Tables 3311 to 3325

Compounds of the formula Ia.35 in which $R^{62}$ is as defined in tables 3101 to 3115, and the combination of $R^{2a}$, $R^{2b}$ and $R^{2c}$ for a compound corresponds in each case to one row of Table A Tables 3326 to 3340

Compounds of the formula Ia.36 in which $R^{62}$ is as defined in tables 3101 to 3115, and the combination of $R^{2a}$, $R^{2b}$ and $R^{2c}$ for a compound corresponds in each case to one row of Table A Tables 3341 to 3355

Compounds of the formula Ia.37 in which $R^{62}$ is as defined in tables 3101 to 3115, and the combination of $R^{2a}$, $R^{2b}$ and $R^{2c}$ for a compound corresponds in each case to one row of Table A Tables 3356 to 3370

Compounds of the formula Ia.38 in which $R^{62}$ is as defined in tables 3101 to 3115, and the combination of $R^{2a}$, $R^{2b}$ and $R^{2c}$ for a compound corresponds in each case to one row of Table A Tables 3371 to 3385

Compounds of the formula Ia.39 in which $R^{62}$ is as defined in tables 3101 to 3115, and the combination of $R^{2a}$, $R^{2b}$ and $R^{2c}$ for a compound corresponds in each case to one row of Table A Tables 3386 to 3400

Compounds of the formula Ia.40 in which $R^{62}$ is as defined in tables 3101 to 3115, and the combination of $R^{2a}$, $R^{2b}$ and $R^{2c}$ for a compound corresponds in each case to one row of Table A

TABLE A

| No. | $R^{2a}$ | $R^{2b}$ | $R^{2c}$ |
|---|---|---|---|
| A-1 | F | F | H |
| A-2 | F | H | F |
| A-3 | F | F | F |
| A-4 | F | Cl | F |
| A-5 | F | Br | F |
| A-6 | F | H | Cl |
| A-7 | F | H | Br |
| A-8 | Cl | F | H |
| A-9 | Cl | H | Cl |
| A-10 | Cl | F | H |
| A-11 | Cl | Cl | Cl |
| A-12 | Cl | F | Cl |
| A-13 | Cl | Br | Cl |
| A-14 | Cl | H | Br |
| A-15 | Br | F | H |
| A-16 | Br | H | Br |
| A-17 | Br | F | Br |
| A-18 | Br | Cl | Br |
| A-19 | CF$_3$ | H | H |
| A-20 | CF$_3$ | H | F |
| A-21 | CF$_3$ | H | Cl |
| A-22 | CF$_3$ | H | Br |
| A-23 | CF$_3$ | H | CF$_3$ |
| A-24 | CF$_3$ | F | F |
| A-25 | CF$_3$ | Cl | Cl |
| A-26 | CF$_3$ | F | H |
| A-27 | OCF$_3$ | H | F |
| A-28 | OCF$_3$ | H | Cl |
| A-29 | OCF$_3$ | F | H |
| A-30 | OCF$_3$ | H | CF$_3$ |
| A-31 | OCF$_3$ | H | H |

Among the above compounds, preference is given to compounds Ia.1, Ia.5 and Ia.6, and in particular to Ia.1.

In a specific embodiment, the compounds I are selected from the compounds specified in the examples, either as a free base or in form of an agriculturally or veterinarily acceptable salt, an N-oxide or a stereoisomer thereof.

The compounds of the formula (I) can be prepared by the methods as described in the below schemes or in the synthesis descriptions of the working examples, or by standard methods of organic chemistry. The substituents, variables and indices are as defined above for formula (I), if not otherwise specified.

Compounds of formula I wherein $X^1$ is O and wherein $R^{3b}$ is hydrogen (termed below as compounds I.a) can be prepared by reacting a compound of formula 1 as shown in scheme 1 below in an imination/Michael addition reaction with hydroxylamine. A' is A or a precursor of A. Typical precursors of A are a halogen atom, CN, carboxy, $C(O)OR^{z1}$ or $—OSO_2—R^{z1}$, where $R^{z1}$ is $C_1$-$C_4$-alkyl, $C_1$-$C_4$-haloalkyl or phenyl which may be substituted by 1, 2 or 3 radicals selected from $C_1$-$C_4$-alkyl, $C_1$-$C_4$-haloalkyl $C_1$-$C_4$-alkoxy or $C_1$-$C_4$-haloalkoxy. Compounds I' correspond to compounds I when A' is A. Compounds I.a' correspond to compounds I.a when A' is A. Suitable reaction conditions are described, for example, in WO 2012/158396. Suitably, hydroxylamine is used as the hydrochloride salt. The reaction is generally carried out in the presence of a base, such as NaOH, KOH, $Na_2CO_3$ and the like. Suitable solvents are aqueous, such as water or mixtures of water with polar solvents, such as tetrahydrofuran, dioxane and lower alkanols. If necessary (i.e. if A' is a precursor of A), A' is then converted into a group A.

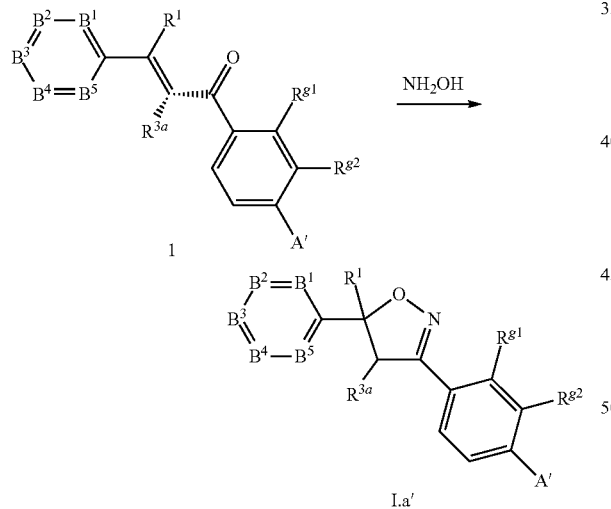

Scheme 1

Compounds of formula I wherein $X^1$ is $CH_2$ and wherein $R^{3b}$ is hydrogen (termed below as compounds I.b) can be prepared by first subjecting a compound of formula 1 to a Michael addition with nitromethane to 2, then reducing the nitro group of 2 to an amino group. The resulting aminoketone reacts spontaneously to the pyrroline I.b', as shown in scheme 2 below. Compounds I.b' correspond to compounds I.b when A' is A. Suitable reaction conditions are described, for example, in US 2010/0298558. The Michael addition of nitromethane to 1 is carried out in the presence of a base. Suitable bases are for example alkali hydroxides and alcoholates, but preferably non-nucleophilic bases, such as DBN or DBU, are used. Suitable solvents depend i.a. on the base used. If an alkali hydroxide is used, suitably an aqueous medium, such as water of mixtures thereof with lower alkanols are used, while alkoxides are used in the respective alcohol. If non-nucleophilic bases are used, polar, non-protic solvents, such as acetonitrile, tetrahydrofuran, dioxane and the like are preferred. If necessary (i.e. if A' is a precursor of A), A' is then converted into a group A. Reduction of 2 is carried out with a suitable reduction agent, such as Zn, Sn, Sn(II) salts, Fe or hydrogen-producing agents, such as ammonium formate in the presence of Zn or Pd.

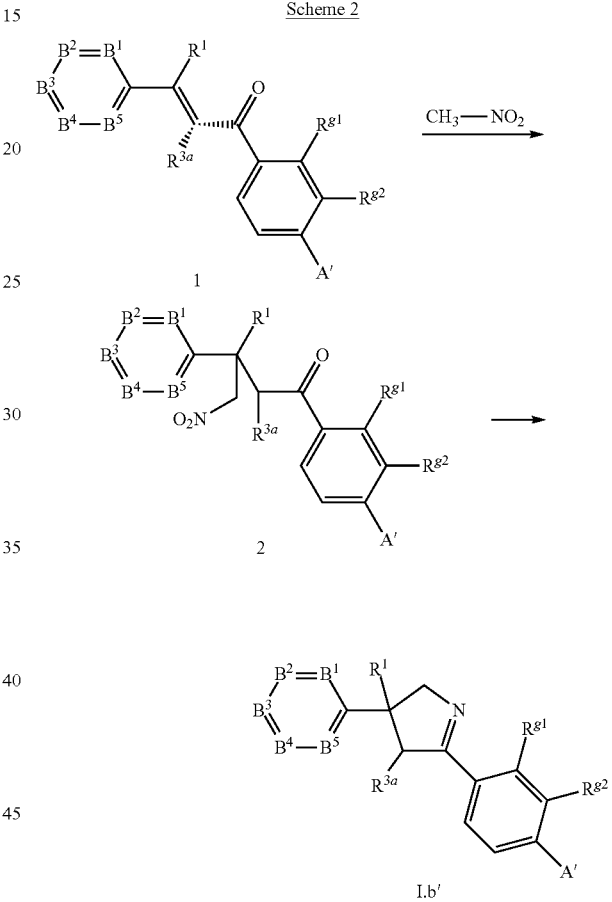

Scheme 2

Compound 1 can be prepared in analogy to the method described in EP-A-2172462 and as shown in scheme 3 below by subjecting the ketones 3 and 4 to an aldol condensation.

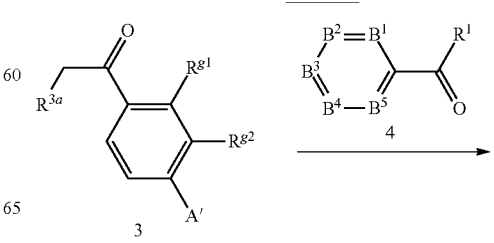

Scheme 3

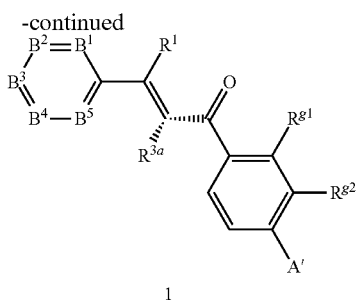

Compounds I wherein A is A¹ wherein W is O can be prepared by reacting a compound I' wherein A' is Cl, Br, I or triflate with carbon monoxide in the presence of a palladium catalyst and an alcohol ROH, wherein R is $C_1$-$C_4$-alkyl, to a compound of formula 5. Suitable palladium catalysts are for example those described in WO 2011/161130.

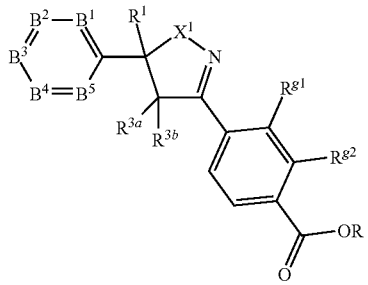

This ester is then hydrolyzed to the respective carboxylic acid, which is then reacted under standard amidation conditions with an amine $NHR^{51}R^{61}$. Hydrolyzation can be carried out under standard conditions, e.g. under acidic conditions using for example hydrochloric acid, sulfuric acid or trifluoroacetic acid, or under basic conditions using for example an alkali metal hydroxide, such as LiOH, NaOH or KOH. Amidation is preferably carried out by activation of the carboxylic acids with oxalylchloride [$(COCl)_2$] or thionylchloride ($SOCl_2$) to the respective acid chlorides, followed by reaction with an amine $NHR^{51}R^{61}$. Alternatively, amidation is carried out in the presence of a coupling reagent. Suitable coupling reagents (activators) are well known and are for instance selected from carbodiimides, such as DCC (dicyclohexylcarbodiimide) and DIC (diisopropylcarbodiimide), benzotriazol derivatives, such as HATU (O-(7-azabenzotriazol-1-yl)-N,N,N',N'-tetramethyluronium hexafluorophosphate), HBTU ((O-benzotriazol-1-yl)-N,N,N',N'-tetramethyluronium hexafluorophosphate) and HCTU (1H-benzotriazolium-1-[bis(dimethylamino) methylene]-5-chloro tetrafluoroborate) and phosphonium-derived activators, such as BOP ((benzotriazol-1-yloxy)-tris(dimethyl-amino)phosphonium hexafluorophosphate), Py-BOP ((benzotriazol-1-yloxy)-tripyrrolidinphosphonium hexafluorophosphate) and Py-BrOP (bromotripyrrolidinphosphonium hexafluorophosphate). Generally, the activator is used in excess. The benzotriazol and phosphonium coupling reagents are generally used in a basic medium.

Compounds I wherein A is A¹ wherein W is S, can be prepared by reacting the corresponding oxo-compound (W is O) with Lawesson's reagent (CAS 19172-47-5), see for example Jesberger et al., Synthesis, 2003, 1929-1958 and references therein. Solvents such as HMPA or THF at an elevated temperature such as 60° C. to 100° C. can be used. Preferred reaction conditions are THF at 65° C.

Compounds I wherein A is A¹ can also be prepared from compounds I' in which A' is an aldehyde group. This aldehyde group can be oxidized to compounds I' wherein A' is a carboxyl group. Suitable conditions are for example those of the Pinnick or Lindgren oxidation using a chlorite, such as sodium chlorite $NaClO_2$ as oxidation agent. As scavenger for the hypochlorite (HOCl) formed in the reaction, 2-methyl-2-butene or hydrogen peroxide can be used. The Pinnick or Lindgren oxidation is generally carried out in a water-containing solvent under slightly acidic, buffered conditions (pH ca. 3-5; use of a hydrogen phosphate, e.g. $NaH_2PO_4$). Other suitable oxidation conditions are described, for example, in WO 2011/022337. The resulting carboxylic acid can then be further subjected to an amidation as described above to afford compounds I wherein A is A¹ and A¹ is $C(O)NR^{51}R^{61}$.

Compounds I' in which A' is an aldehyde group can in turn be prepared from compounds I', in which A' is Cl, Br, I or $-OSO_2-R^{z1}$, where $R^{z1}$ is as defined above, by reaction with carbon monoxide and a hydride source, such as triethylsilane, in the presence of a transition metal complex catalyst, preferably a palladium catalyst. Suitable reaction conditions are described, for example, in WO 2011/161130. Alternatively, compounds I' in which A' is an aldehyde group (CHO) can also be obtained by reducing a compound I' in which A' is $C(O)OR^{z1}$ with $R^{z1}=C_1$-$C_4$-alkyl with diisobutylaluminium hydride (DIBAL-H) either directly to the aldehyde or via the corresponding alcohol, which is then oxidized to the aldehyde.

Compounds I wherein $R^{3b}$ is not hydrogen can be prepared from compounds I.a' or I.b' in analogy to the methods described in WO 2010/020521 by reacting these with a base, such as lithium diisopropylamine, followed by the addition of an electrophile, e.g. a halogenating agent, such as 4-iodotoluene difluoride, N-fluorobenzenesulfonimide ("NFSI"), N-chlorosuccinimide ("NCS"), N-bromosuccinimide ("NBS") or N-iodosuccinimide ("NIS").

Compounds I wherein A is a group A², wherein $R^{7a}$ and $R^{7b}$ are hydrogen, can be prepared by reducing a compound I' wherein A' is —CHO or —C(O)OH for example with LAH (lithium aluminium hydride) or DIBAL-H (diisobutyl aluminium hydride) to a compound 6.

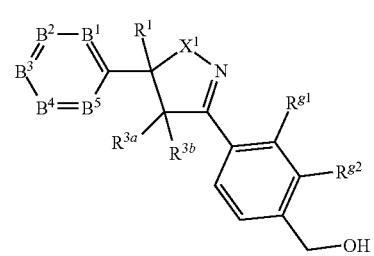

This is then reacted in an $S_N$ reaction with an amide $NHR^{52}C(O)R^{62}$, or, better, with an amine $NH_2R^{52}$. In both cases, the OH group can first be converted into a better leaving group, e.g. into a sulfonate (for example mesylate, tosylate or a triflate group). In the second variant (reaction with an amine $NH_2R^{52}$) the resulting benzylic amine is then reacted with an acid $R^{62}$—COOH or a derivative thereof, such as its acid chloride $R^{62}$—COCl, in an amidation reaction.

Compounds I wherein A is a group $A^2$, wherein $R^{7a}$ is methyl or $C_1$-haloalkyl and $R^{7b}$ is hydrogen, can be prepared by subjecting a ketone 7

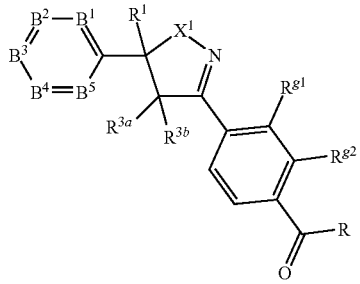

7 in which R corresponds to $R^{7a}$, which is methyl or $C_1$-haloalkyl, to a reductive amination to furnish compounds 8. Typical conditions for the reductive amination are: Reacting ketone 7 with an amine $H_2NR^{52}$ to yield the corresponding imine which is reduced to amine 8 with a reducing agent reagent such as $Na(CN)BH_3$. The reaction from ketone 7 to amine 8 may also be carried out as a one pot procedure.

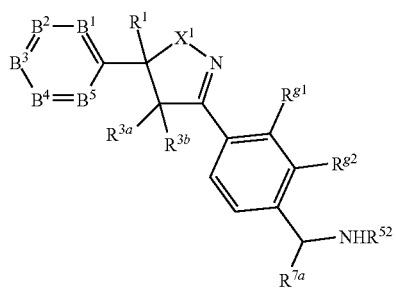

8

The amine 8 is then reacted with an acid $R^{62}$—COOH or a derivative thereof, such as its acid chloride $R^{62}$—COCl, in an amidation reaction, as described above.

The ketone 7 is in turn obtained by reacting a compound I' wherein A' is an aldehyde group —CHO with a Grignard reagent R-MgHal, where Hal is Cl, Br or I, or an organolithium compound R—Li to obtain an alcohol of formula 9, which is then oxidized to a carbonyl compound of the formula 7.

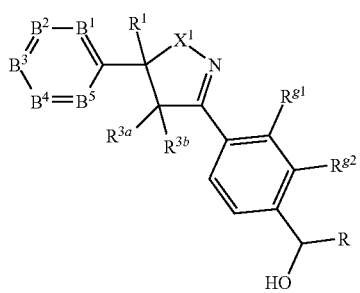

9

For obtaining compounds in which $R^{7a}$ and $R^{7b}$ are methyl or $C_1$-haloalkyl, carbonyl compounds such as 7, in which R corresponds to $R^{7a}$ which is methyl or $C_1$-haloalkyl, is reacted with a Grignard reagent $R^{7b}$—MgHal, where Hal is Cl, Br or I, or an organolithium compound $R^{7b}$—Li, where $R^{7b}$ is methyl or $C_1$-haloalkyl, to obtain an alcohol of formula 10.

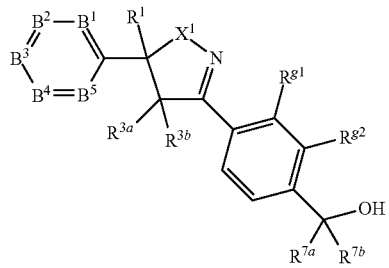

10

Alcohol 10 can then be converted into amine 11 via the corresponding azide, as described, for example, in Organic Letters, 2001, 3(20), 3145-3148.

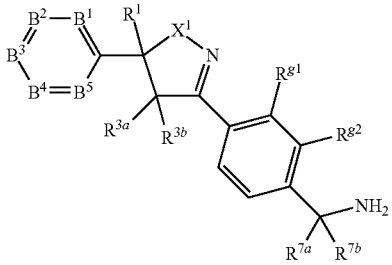

11

This can be converted into compounds I wherein $R^{52}$ is different from hydrogen, for example by standard alkylation reactions. The group $C(O)R^{62}$ can be introduced as described above by acylation with an acid $R^{62}$—COOH or a derivative thereof, such as its acid chloride $R^{62}$—COCl.

Compounds I wherein A is a group $A^2$, wherein $R^{7a}$ is CN, methyl or $C_1$-haloalkyl and $R^{7b}$ is hydrogen, can be prepared by converting a compound I' wherein A' is an aldehyde group CHO into an imine 12 by reaction with an amine derivative $NH_2R$, wherein R is tert-butyl sulfinyl.

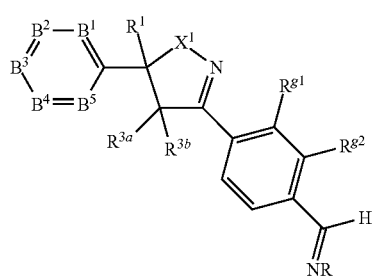

12

This imine is then reacted with a compound X—$R^{7a}$ in an addition reaction. Suitable reagents are for example $Si(CH_3)_3$—CN or HCN for introducing CN as $R^{7a}$, or $Si(CH_3)_3$—$CF_3$ for introducing $CF_3$ as $R^{7a}$, or methyl magnesium bromide ($CH_3$—MgBr) for introducing a methyl group as $R^{7a}$. Suitable conditions are described, for example, in J. Am. Chem. Soc. 2009, 3850-3851 and the references cited therein or in Chemistry—A European Journal 2009, 15, 11642-11659. R (tert-butylsulfinyl) can then be removed under acidic conditions, such as hydrochloric acid in methanol, to yield an amino group. The group $C(O)R^{62}$ can then be introduced as described above by acylating this amino group with an acid $R^{62}$—COOH or a derivative thereof, such as its acid chloride $R^{62}$—COCl.

As a rule, the compounds of formula I including their stereoisomers, salts, and N-oxides, and their precursors in the synthesis process, can be prepared by the methods described above. If individual compounds can not be prepared via the above-described routes, they can be prepared by derivatization of other compounds I or the respective precursor or by customary modifications of the synthesis routes described. For example, in individual cases, certain compounds of formula (I) can advantageously be prepared from other compounds of formula (I) by derivatization, e.g. by ester hydrolysis, amidation, esterification, ether cleavage, olefination, reduction, oxidation and the like, or by customary modifications of the synthesis routes described.

The reaction mixtures are worked up in the customary manner, for example by mixing with water, separating the phases, and, if appropriate, purifying the crude products by chromatography, for example on alumina or on silica gel. Some of the intermediates and end products may be obtained in the form of colorless or pale brown viscous oils which are freed or purified from volatile components under reduced pressure and at moderately elevated temperature. If the intermediates and end products are obtained as solids, they may be purified by recrystallization or trituration.

Due to their excellent activity, the compounds of the present invention may be used for controlling invertebrate pests.

Accordingly, the present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of the present invention or a composition as defined above. The invention also relates to the use of a compound of the invention, of a stereoisomer and/or of an agriculturally or veterinarily acceptable salt thereof for combating invertebrate pests Preferably, the method of the invention serves for protecting plant propagation material (such as seed) and the plant which grows therefrom from invertebrate pest attack or infestation and comprises treating the plant propagation material (such as seed) with a pesticidally effective amount of a compound of the present invention as defined above or with a pesticidally effective amount of an agricultural composition as defined above and below. The method of the invention is not limited to the protection of the "substrate" (plant, plant propagation materials, soil material etc.) which has been treated according to the invention, but also has a preventive effect, thus, for example, according protection to a plant which grows from a treated plant propagation materials (such as seed), the plant itself not having been treated.

Alternatively preferably, the method of the invention serves for protecting plants from attack or infestation by invertebrate pests, which method comprises treating the plants with a pesticidally effective amount of at least one compound of the invention, a stereoisomer thereof and/or at least one agriculturally acceptable salt thereof.

In the sense of the present invention, "invertebrate pests" are preferably selected from arthropods and nematodes, more preferably from harmful insects, arachnids and nematodes, and even more preferably from insects, acarids and nematodes. In the sense of the present invention, "invertebrate pests" are most preferably insects.

The invention further provides an agricultural composition for combating invertebrate pests, which comprises such an amount of at least one compound according to the invention and at least one inert liquid and/or solid agronomically acceptable carrier that has a pesticidal action and, if desired, at least one surfactant.

Such a composition may comprise a single active compound of the present invention or a mixture of several active compounds of the present invention. The composition according to the present invention may comprise an individual isomer or mixtures of isomers or a salt as well as individual tautomers or mixtures of tautomers.

The compounds of the present invention, including their salts, stereoisomers and tautomers, are in particular suitable for efficiently controlling animal pests such as arthropods, gastropods and nematodes including but not limited to: insects from the order of Lepidoptera, for example *Achroia grisella, Acleris* spp. such as *A. fimbriana, A. gloverana, A. variana; Acrolepiopsis assectella, Acronicta major, Adoxophyes* spp. such as *A. cyrtosema, A. orana; Aedia leucomelas, Agrotis* spp. such as *A. exclamationis, A. fucosa, A. ipsilon, A. orthogoma, A. segetum, A. subterranea; Alabama argillacea, Aleurodicus dispersus, Alsophila pometaria, Ampelophaga rubiginosa, Amyelois transitella, Anacampsis sarcitella, Anagasta kuehniella, Anarsia lineatella, Anisota senatoria, Antheraea pernyi, Anticarsia (=Thermesia)* spp. such as *A. gemmatalis; Apamea* spp., *Aproaerema modicella, Archips* spp. such as *A. argyrospila, A. fuscocupreanus, A. rosana, A. xyloseanus; Argyresthia conjugella, Argyroploce* spp., *Argyrotaenia* spp. such as *A. velutinana; Athetis mindara, Austroasca viridigrisea, Autographa gamma, Autographa nigrisigna, Barathra brassicae, Bedellia* spp., *Bonagota salubricola, Borbo cinnara, Bucculatrix thurberiella, Bupalus piniarius, Busseola* spp., *Cacoecia* spp. such as *C. murinana, C. podana, Cactoblastis cactorum, Cadra cautella, Calingo braziliensis, Caloptilis theivora, Capua reticulana, Carposina* spp. such as *C. niponensis, C. sasakii; Cephus* spp., *Chaetocnema aridula, Cheimatobia brumata, Chilo* spp. such as *C. Indicus, C. suppressalis, C. partellus, Choreutis pariana, Choristoneura* spp. such as *C. conflictana, C. fumiferana, C. longicellana, C. murinana, C. occidentalis, C. rosaceana; Chrysodeixis (=Pseudoplusia)* spp. such as *C. eriosoma, C. includens; Cirphis unipuncta, Clysia ambiguella, Cnaphalocerus* spp., *Cnaphalocrocis medinals, Cnephasia* spp., *Cochylis hospes, Coleophora* spp., *Colias eurytheme, Conopomorpha* spp., *Conotrachelus* spp., *Copitarsia* spp., *Corcyra cephalonica, Crambus caliginosellus, Crambus teterrellus, Crocidosema (=Epinotia) aporema, Cydalima (=Diaphania) perspectalis, Cydia (=Carpocapsa)* spp. such as *C. pomonella, C. latiferreana; Dalaca noctuides, Datana integerrima, Dasychira pinicola, Dendrolimus* spp. such as *D. pini, D. spectabilis, D. sibiricus; Desmia funeralis, Diaphania* spp. such as *D. nitidalis, D. hyalinata, Diatraea grandiosella, Diatraea saccharalis, Diphthera festiva, Earias* spp. such as *E. insulana, E. vittella; Ecdytolopha aurantianu, Egira (=Xylomyges) curialis, Elasmopalpus lignosellus, Eldana saccharina, Endopiza viteana, Ennomos subsignaria, Eoreuma loftini, Ephestia* spp. such as *E.* cautella, *E. elutella, E. kuehniella; Epinotia aporema, Epiphyas postvittana, Erannis tiliaria, Erionota thrax, Etiella* spp., *Eulia* spp., *Eupoecilia ambiguella, Euproctis chrysorrhoea, Euxoa* spp., *Evetria bouliana, Faronta albilinea, Feltia* spp. such as *F. subterranean; Galleria mellonella, Gracillaria* spp., *Grapholita* spp. such as *G. funebrana, G. molesta, G. inopinata; Halysidota* spp., *Harrisina americana, Hedylepta* spp., *Helicoverpa* spp. such as *H. armigera* (=*Heliothis armigera*), *H. zea* (=*Heliothis zea*), *Heliothis* spp. such as *H. assulta, H. subflexa, H. virescens, Hellula* spp. such as *H. undalis, H. rogatalis; Helocoverpa gelotopoeon, Hemileuca oliviae, Herpetogramma licarsisalis, Hibernia defoliaria, Hofmannophila pseudospretella, Homoeosoma electellum, Homona magnanima, Hypena scabra, Hyphantria cunea, Hyponomeuta padella, Hyponomeuta malinellus, Kakivoria flavofasciata, Keiferia lycopersicella, Lambdina fiscellaria fiscellaria, Lambdina fiscellaria lugubrosa, Lamprosema indicata, Laspeyresia molesta, Leguminivora glycinivorella, Lerodea eufala, Leucinodes orbonalis, Leucoma salicis, Leucoptera* spp. such as *L. coffeella, L. scitella; Leuminivora lycinivorella, Lithocolletis blancardella, Lithophane antennata, Llattia octo* (=*Amyna axis*), *Lobesia botrana, Lophocampa* spp., *Loxagrotis albicosta, Loxostege* spp. such as *L. sticticalis, L. cereralis; Lymantria* spp. such as *L. dispar, L. monacha, Lyonetia clerkella, Lyonetia prunifoliella, Malacosoma* spp. such as *M. americanum, M. californicum, M. constrictum, M. neustria, Mamestra* spp. such as *M. brassicae, M. configurata; Mamstra brassicae, Manduca* spp. such as *M. quinquemaculata, M. sexta; Marasmia* spp., *Marmara* spp., *Maruca testulalis, Megalopyge lanata, Melanchra picta, Melanitis leda, Mocis* spp. such as *M. lapites, M. repanda; Mocis latipes, Monochroa fragariae, Mythimna separata, Nemapogon cloacella, Neoleucinodes elegantalis, Nepytia* spp., *Nymphula* spp., *Oiketicus* spp., *Omiodes indicata, Omphisa anastomosalis, Operophtera brumata, Orgyia pseudotsugata, Oria* spp., *Orthaga thyrisalis, Ostrinia* spp. such as *O. nubilalis; Oulema oryzae, Paleacrita vernata, Panolis flammea, Parnara* spp., *Papaipema nebris, Papilio cresphontes, Paramyelois transitella, Paranthrene regalis, Paysandisia archon, Pectinophora* spp. such as *P. gossypiella; Peridroma saucia, Perileucoptera* spp., such as *P. coffeella; Phalera bucephala, Phryganidia californica, Phthorimaea* spp. such as *P. operculella; Phyllocnistis citrella, Phyllonorycter* spp. such as *P. blancardella, P. crataegella, P. issik, P. ringoniella; Pieris* spp. such as *P. brassicae, P. rapae, P. napi; Pilocrocis tripunctata, Plathypena scabra, Platynota* spp. such as *P. flavedana, P. idaeusalis, P. stultana; Platyptilia carduidactyla, Plebejus argus, Plodia interpunctella, Plusia* spp., *Plutella maculipennis, Plutella xylostella, Pontia protodica, Prays* spp., *Prodenia* spp., *Proxenus lepigone, Pseudaletia* spp. such as *P. sequax, P. unipuncta; Pyrausta nubilalis, Rachiplusia nu, Richia albicosta, Rhizobius ventralis, Rhyacionia frustrana, Sabulodes aegrotata, Schizura concinna, Schoenobius* spp., *Schreckensteinia festaliella, Scirpophaga* spp. such as *S. incertulas, S. innotata; Scotia segetum, Sesamia* spp. such as *S. inferens, Seudyra subflava, Sitotroga cerealella, Sparganothis pilleriana, Spilonota lechriaspis, S. ocellana, Spodoptera* (=*Lamphygma*) spp. such as *S. cosmoides, S. eridania, S. exigua, S. frugiperda, S. latifascia, S. littoralis, S. litura, S. omithogalli; Stigmella* spp., *Stomopteryx subsecivella, Strymon bazochi Sylepta derogata, Synanthedon* spp. such as *S. exitiosa, Tecia solanivora, Telehin licus, Thaumatopoea pityocampa, Thaumatotibia* (=*Cryptophlebia*) *leucotreta, Thaumetopoea pityocampa, Thecla* spp., *Thereslmima ampelophaga, Thyrinteina* spp., *Tildenia inconspicuella, Tinea* spp. such as *T. cloacella, T pellionella; Tineola bisselliella, Tortrix* spp. such as *T. viridana; Trichophaga tapetzella, Trichoplusia* spp. such as *T. ni; Tuta* (=*Scrobipalpula*) *absoluta, Udea* spp. such as *U. rubigalis, U. rubigalis; Virachola* spp., *Yponomeuta padella*, and *Zeiraphera canadensis;* insects from the order of Coleoptera, for example *Acalymma vittatum, Acanthoschedes obtectus, Adoretus* spp., *Agelastica alni, Agrilus* spp. such as *A. anxlus, A. planipennis, A. sinuatus; Agriotes* spp. such as *A. fuscicollis, A. lineatus, A. obscurus; Alphitobius diaperinus, Amphimallus solstitialis, Anisandrus dispar, Anisoplia austriaca, Anobium punctatum, Anomala corpulenta, Anomala rufocuprea, Anoplophora* spp. such as *A. glabripennis; Anthonomus* spp. such as *A. eugenii, A. grandis, A. pomorum; Anthrenus* spp., *Aphthona euphoridae, Apion* spp., *Apogonia* spp., *Athous haemorrhoidalis, Atomaria* spp. such as *A. linearis; Attagenus* spp., *Aulacophora femoralis, Blastophagus piniperda, Blitophaga undata, Bruchidius obtectus, Bruchus* spp. such as *B. lentis, B. pisorum, B. rufimanus; Byctiscus betulae, Callidiellum rufipenne, Callopistria floridensis, Callosobruchus chinensis, Cameraria ohridella, Cassida nebulosa, Cerotoma trifurcata, Cetonia aurata, Ceuthorhynchus* spp. such as *C. assimilils, C. napi; Chaetocnema tibialis, Cleonus mendicus, Conoderus* spp. such as *C. vespertinus; Conotrachelus nenuphar, Cosmopolites* spp., *Costelytra zealandica, Crioceris asparagi, Cryptolestes ferrugineus, Cryptorhynchus lapathi, Ctenicera* spp. such as *C. destructor; Curculio* spp., *Cylindrocopturus* spp., *Cyclocephala* spp., *Dactylispa balyi, Dectes texanus, Dermestes* spp., *Diabrotica* spp. such as *D. undecimpunctata, D. speciosa, D. longicornis, D. semipunctata, D. virgifera; Diaprepes abbreviates, Dichocrocis* spp., *Dicladispa armigera, Diloboderus abderus, Diocalandra frumenti* (*Diocalandra stigmaticollis*), *Enaphalodes rufulus, Epilachna* spp. such as *E. varivestis, E. vigintioctomaculata; Epitrix* spp. such as *E. hirtipennis, E. similaris; Eutheola humilis, Eutinobothrus brasiliensis, Faustinus cubae, Gibbium psylloides, Gnathocerus cornutus, Hellula undalis, Heteronychus arator, Hylamorpha elegans, Hylobius abietis, Hylotrupes bajulus, Hypera* spp. such as *H. brunneipennis, H. postica; Hypomeces squamosus, Hypothenemus* spp., *Ips typographus, Lachnosterna consanguinea, Lasioderma serricorne, Latheticus oryzae, Lathridius* spp., *Lema* spp. such as *L. bilineata, L. melanopus; Leptinotarsa* spp. such as *L. decemlineata; Leptispa pygmaea, Limonius californicus, Lissorhoptrus oryzophilus, Lixus* spp., *Luperodes* spp., *Lyctus* spp. such as *L. bruneus; Liogenys fuscus, Macrodactylus* spp. such as *M. subspinosus; Maladera matrida, Megaplatypus mutates, Megascelis* spp., *Melanotus communis, Meligethes* spp. such as *M. aeneus; Melolontha* spp. such as *M. hippocastani, M. melolontha; Metamasius hemipterus, Microtheca* spp., *Migdolus* spp. such as *M. fryanus, Monochamus* spp. such as *M. alternatus; Naupactus xanthographus, Niptus hololeucus, Oberia brevis, Oemona hirta, Oryctes rhinoceros, Oryzaephilus surinamensis, Oryzaphagus oryzae, Otiorrhynchus sulcatus, Otiorrhynchus ovatus, Otiorrhynchus sulcatus, Oulema melanopus, Oulema oryzae, Oxycetonia jucunda, Phaedon* spp. such as *P. brassicae, P. cochleariae; Phoracantha recurva, Phyllobius pyri, Phyllopertha horticola, Phyllophaga* spp. such as *P. helleri; Phyllotreta* spp. such as *P. chrysocephala, P. nemorum, P. striolata, P. vittula; Phyllopertha horticola, Popillia japonica, Premnotrypes* spp., *Psacothea hilaris, Psylliodes chrysocephala, Prostephanus truncates, Psylliodes* spp., *Ptinus* spp., *Pulga saltona, Rhizopertha dominica, Rhynchophorus* spp. such as *R. billineatus, R. ferrugineus, R.*

*palmarum, R. phoenicis, R. vulneratus; Saperda candida, Scolytus schevyrewi, Scyphophorus acupunctatus, Sitona lineatus, Sitophilus* spp. such as *S. granaria, S. oryzae, S. zeamais; Sphenophorus* spp. such as *S. levis; Stegobium paniceum, Sternechus* spp. such as *S. subsignatus; Strophomorphus ctenotus, Symphyletes* spp., *Tanymecus* spp., *Tenebrio molitor, Tenebrioides mauretanicus, Tribolium* spp. such as *T. castaneum; Trogoderma* spp., *Tychius* spp., *Xylotrechus* spp. such as *X. pyrrhoderus;* and, *Zabrus* spp. such as *Z. tenebriodes;* insects from the order of Diptera for example *Aedes* spp. such as *A. aegypti, A. albopictus, A. vexans; Anastrepha ludens, Anopheles* spp. such as *A. albimanus, A. crucians, A. freeborni, A. gambiae, A. leucosphyrus, A. maculipennis, A. minimus, A. quadrimaculatus, A. sinensis; Bactrocera invadens, Bibio hortulanus, Calliphora erythrocephala, Calliphora vicina, Ceratitis capitata, Chrysomyia* spp. such as *C. bezziana, C. hominivorax, C. macellaria; Chrysops atlanticus, Chrysops discalis, Chrysops silacea, Cochliomyia* spp. such as *C. hominivorax; Contarinia* spp. such as *C. sorghicola; Cordylobia anthropophaga, Culex* spp. such as *C. nigripalpus, C. pipiens, C. quinquefasciatus, C. tarsals, C. tritaeniorhynchus; Culicoides furens, Culilseta inornata, Culiseta melanura, Cuterebra* spp., *Dacus cucurbitae, Dacus oleae, Dasineura brassicae, Dasineura oxycoccana, Delia* spp. such as *D. antique, D. coarctata, D. platura, D. radicum; Dermatobia hominis, Drosophila* spp. such as *D. suzukii, Fannia* spp. such as *F. canicularis; Gastraphilus* spp. such as *G. intestinalis; Geomyza tipunctata, Glossina* spp. such as *G. fuscipes, G. morsitans, G. palpalis, G. tachinoides; Haematobia irritans, Haplodiplosis equestris, Hippelates* spp., *Hylemyia* spp. such as *H. platura; Hypoderma* spp. such as *H. lineata; Hyppobosca* spp., *Hydrellia philippina, Leptoconops torrens, Liriomyza* spp. such as *L. sativae, L. trifoli; Lucilia* spp. such as *L. caprina, L. cuprina, L. sericata; Lycoria pectoralis, Mansonia titillanus, Mayetiola* spp. such as *M. destructor; Musca* spp. such as *M. autumnalis, M. domestica; Muscina stabulans, Oestrus* spp. such as *O. ovis; Opomyza florum, Oscinella* spp. such as *O. frit; Orseolia oryzae, Pegomya hysocyami, Phlebotomus argentipes, Phorbia* spp. such as *P. antiqua, P. brassicae, P. coarctata; Phytomyza gymnostoma, Prosimulilum mixtum, Psila rosae, Psorophora columbiae, Psorophora discolor, Rhagoletis* spp. such as *R. ceras, R. cingulate, R. indifferens, R. mendax, R. pomonella, Rivellia quadrifasciata, Sarcophaga* spp. such as *S. haemorrhoidalis; Simulium vittatum, Sitodiplosis mosellana, Stomoxys* spp. such as *S. calcitrans; Tabanus* spp. such as *T. atratus, T. bovinus, T. lineola, T. similis; Tannia* spp., *Thecodiplosis japonensis, Tipula oleracea, Tipula paludosa,* and *Wohlfahrtia* spp.;

insects from the order of Thysanoptera for example, *Baliothrips biformis, Dichromothrips corbetti, Dichromothrips* ssp., *Echinothrips americanus, Enneothrips flavens, Frankliniella* spp. such as *F. fusca, F. occidentalis, F. tritici, Heliothrips* spp., *Hercinothrips femoralis, Kakothrips* spp., *Microcephalothrips abdominalis, Neohydatothrips samayunkur, Pezothrips kellyanus, Rhipiphorothrips cruentatus, Scirtothrips* spp. such as *S. citri, S. dorsalis, S. perseae; Stenchaeto thrips* spp., *Taeniothrips cardamoni, Taeniothrips inconsequens, Thrips* spp. such as *T. imagines, T. hawaiiensis, T. oryzae, T. palmi, T. parvispinus, T. tabaci,* insects from the order of Hemiptera for example, *Acizzia jamatonica, Acrosternum* spp. such as *A. hillare; Acyrthosipon* spp. such as *A. onobrychis, A. pisum, Adelges laricis, Adelges tsugae, Adelphocoris* spp. such as *A. rapidus, A. superbus; Aeneolamia* spp., *Agonoscena* spp., *Aulacorthum solani Aleurocanthus woglumi, Aleurodes* spp., *Aleurodicus disperses, Aleurolobus barodensis, Aleurothrixus* spp., *Amrasca* spp., *Anasa tristis, Antestiopsis* spp., *Anuraphis cardui, Aonidiella* spp., *Aphanostigma piri, Aphidula nasturtii, Aphis* spp. such as *A. craccivora, A. fabae, A. forbesi A. gossypii, A. grossulariae, A. maidiradicis, A. pomi, A. sambuci, A. schneideri, A. spiraecola, Arboridia apicalis, Arilus critatus, Aspidiella* spp., *Aspidiotus* spp., *Atanus* spp., *Aulacaspis yasumatsui Aulacorthum solani Bactericera cockerelli (Paratrioza cockerelli), Bemisia* spp. such as *B. argentifolii, B. tabaci (Aleurodes tabaci), Blissus* spp. such as *B. leucopterus; Brachycaudus* spp. such as *B. cardui, B. helichrysi, B. persicae, B. prunicola; Brachycolus* spp., *Brachycorynella asparagi, Brevicoryne brassicae, Cacopsylla* spp. such as *C. fulguralls, C. pyricola (Psylla piri), Calligypona marginata, Calocoris* spp., *Campylomma livida, Capitophorus horni Carneocephala fulgida, Cavelerius* spp., *Ceraplastes* spp., *Ceratovacuna lanigera, Ceroplastes ceriferus, Cerosipha gossypi Chaetosiphon fragaefolii, Chionaspis tegalensis, Chlorita onukii, Chromaphis juglandicola, Chrysomphalus ficus, Cicadulina mbila, Cimex* spp. such as *C. hemipterus, C. lectularius; Coccomytilus halli, Coccus* spp. such as *C. hesperidum, C. pseudomagnoliarum; Corythucha arcuata, Creontiades dilutus, Cryptomyzus ribis, Chrysomphalus aonidum, Cryptomyzus ribis, Ctenarytaina spatulata, Cyrtopeltis notatus, Dalbulus* spp., *Dasynus piperis, Dialeurodes* spp. such as *D. citrifoll; Dalbulus maidis, Diaphorina* spp. such as *D. cilri; Diaspis* spp. such as *D. bromellae; Dichelops furcatus, Diconocoris hewetti, Doralis* spp., *Dreyfusia nordmannianae, Dreyfusia piceae, Drosicha* spp., *Dysaphis* spp. such as *D. plantaginea, D. pyri, D. radicola, Dysaulacorthum pseudosolani, Dysdercus* spp. such as *D. cingulatus, D. intermedius; Dysmicoccus* spp., *Edessa* spp., *Geocoris* spp., *Empoasca* spp. such as *E. fabae, E. solana; Epidlaspis leperli, Eriosoma* spp. such as *E. lanigerum, E. pyricola; Erythroneura* spp., *Eurygaster* spp. such as *E. integriceps; Euscelis bilobatus, Euschistus* spp. such as *E. heros, E. impictiventris, E. servus, Fiorinia theae, Geococcus coffeae, Glycaspis brimblecombei, Halyomorpha* spp. such as *H. halys; Heliopeltis* spp., *Homalodisca vitripennis (=H. coagulata), Horcias nobilellus, Hyalopterus pruni, Hyperomyzus lactucae, Icerya* spp. such as *I. purchase; Idiocerus* spp., *Idioscopus* spp., *Laodelphax striatellus, Lecanium* spp., *Lecanoideus floccissimus, Lepidosaphes* spp. such as *L. ulmi; Leptocorisa* spp., *Leptoglossus phyllopus, Lipaphis erysimi, Lygus* spp. such as *L. hesperus, L. lineolaris, L. pratensis; Maconellicoccus hirsutus, Marchalina hellenica, Macropes excavatus, Macrosiphum* spp. such as *M. rosae, M. avenae, M. euphorbiae; Macrosteles quadrilineatus, Mahanarva fimbriolata, Megacopta cribraria, Megoura viciae, Melanaphis pyrarius, Melanaphis sacchar, Melanocallis (=Tinocallis) caryaefollae, Metcafiella* spp., *Metopolophium dirhodum, Monellia costalis, Monelliopsis pecanis, Myzocallis coryli, Murgantia* spp., *Myzus* spp. such as *M. ascalonicus, M. cerasi, M. nicotianae, M. persicae, M. varians, Nasonovia ribis-nigri, Neotoxoptera formosana, Neomegalotomus* spp., *Nephotettix* spp. such as *N. malayanus, N. nigropictus, N. parvus, N. virescens; Nezara* spp. such as *N. viridula; Nilaparvata lugens, Nysius huttoni, Oebalus* spp. such as *O. pugnax; Oncometopia* spp., *Orthezia praelonga, Oxycaraenus hyalinipennis, Parabemisia myricae, Parlatoria* spp., *Parthenolecanium* spp. such as *P. corni, P. persicae; Pemphigus* spp. such as *P. bursarius, P. populivenae; Peregrinus maidis, Perkinsiella saccharicida, Phenacoccus* spp. such as *P. aceris, P. gossypii; Phloeomyzus passerini, Phorodon humuli, Phylloxera* spp. such as *P. devastatrix, Piesma quadrata, Piezodorus* spp. such as *P. guildinii; Pinnaspis*

*aspidistrae, Planococcus* spp. such as *P. citri, P. ficus; Prosapia bicincta, Protopulvinaria pyriformis, Psallus seriatus, Pseudacysta persea, Pseudaulacaspis pentagona, Pseudococcus* spp. such as *P. comstocki; Psylla* spp. such as *P. mali; Pteromalus* spp., *Pulvinaria amygdali, Pyrilla* spp., *Quadraspidiotus* spp., such as *Q. perniciosus; Quesada gigas, Rastrococcus* spp., *Reduvius senilis, Rhizoecus americanus, Rhodnius* spp., *Rhopalomyzus ascalonicus, Rhopalosiphum* spp. such as *R. pseudobrassicas, R. insertum, R. maidis, R. padi; Sagatodes* spp., *Sahlbergella singularis, Saissetia* spp., *Sappaphis mala, Sappaphis mali, Scaptocoris* spp., *Scaphoides titanus, Schizaphis graminum, Schizoneura lanuginosa, Scotinophora* spp., *Selenaspidus articulatus, Sitobion avenae, Sogata* spp., *Sogatella furcifera, Solubea insularis, Spissistilus festinus* (=*Stictocephala festina*), *Stephanitis nashi, Stephanitis pyrioides, Stephanitis takeyai, Tenalaphara malayensis, Tetraleurodes perseae, Therioaphis maculate, Thyanta* spp. such as *T. accerra, T. perditor; Tibraca* spp., *Tomaspis* spp., *Toxoptera* spp. such as *T. aurantii; Trialeurodes* spp. such as *T. abutilonea, T. ricini, T. vaporariorum; Triatoma* spp., *Trioza* spp., *Typhlocyba* spp., *Unaspis* spp. such as *U. citri, U. yanonensis;* and *Viteus vitifolii,*

Insects from the order Hymenoptera for example *Acanthomyops interjectus, Athalia rosae, Atta* spp. such as *A. capiguara, A. cephalotes, A. cephalotes, A. laevigata, A. robusta, A. sexdens, A. texana, Bombus* spp., *Brachymyrmex* spp., *Camponotus* spp. such as *C. floridanus, C. pennsylvanicus, C. modoc; Cardiocondyla nuda, Chalibion* sp, *Crematogaster* spp., *Dasymutilla occidentalis, Diprion* spp., *Dolichovespula maculata, Dorymyrmex* spp., *Dryocosmus kuriphilus, Formica* spp., *Hoplocampa* spp. such as *H. minuta, H. testudinea; Iridomyrmex humilis, Lasius* spp. such as *L. niger, Linepithema humile, Liometopum* spp., *Leptocybe invasa, Monomorium* spp. such as *M. pharaonis, Monomorium, Nylandria fulva, Pachycondyla chinensis, Paratrechina longicornis, Paravespula* spp. such as *P. germanica, P. pennsylvanica, P. vulgaris; Pheidole* spp. such as *P. megacephala, Pogonomyrmex* spp. such as *P. barbatus, P. californicus, Polistes rubiginosa, Prenolepis impairs, Pseudomyrmex gracilis, Schelipron* spp., *Sirex cyaneus, Solenopsis* spp. such as *S. geminata, S. invicta, S. molesta, S. richteri, S. xyloni, Sphecius speciosus, Sphex* spp., *Tapinoma* spp. such as *T. melanocephalum, T. sessile; Tetramorium* spp. such as *T. caespitum, T. bicarinatum, Vespa* spp. such as *V. crabro; Vespula* spp. such as *V. squamosal; Wasmannia auropunctata, Xylocopa* sp;

Insects from the order Orthoptera for example *Acheta domesticus, Calliptamus italicus, Chortoicetes terminifera, Ceuthophilus* spp., *Diastrammena asynamora, Dociostaurus maroccanus, Gryllotalpa* spp. such as *G. africana, G. gryllotalpa; Gryllus* spp., *Hieroglyphus daganensis, Kraussaria angulifera, Locusta* spp. such as *L. migratoria, L. pardalina; Melanoplus* spp. such as *M. bivittatus, M. femurrubrum, M. mexicanus, M. sanguinipes, M. spretus; Nomadacris septemfasciata, Oedaleus senegalensis, Scapteriscus* spp., *Schistocerca* spp. such as *S. americana, S. gregaria, Stemopelmatus* spp., *Tachycines asynamorus,* and *Zonozerus variegatus*

Pests from the Class Arachnida for example Acari, e.g. of the families Argasidae, Ixodidae and Sarcoptidae, such as *Amblyomma* spp. (e.g. *A. americanum, A. variegatum, A. maculatum*), *Argas* spp. such as *A. persicu*), *Boophilus* spp. such as *B. annulatus, B. decoloratus, B. microplus, Dermacentor* spp. such as *D. silvarum, D. andersoni, D. variabilis, Hyalomma* spp. such as *H. truncatum, Ixodes* spp. such as *I. ricinus, I. rubicundus, I. scapularis, I. holocyclus, I. pacificus, Rhipicephalus sanguineus, Ornithodorus* spp. such as *O. moubata, O. hermsi, O. turicata*), *Ornithonyssus bacoti, Otobius megnini, Dermanyssus gallinae, Psoroptes* spp. such as *P. ovis, Rhipicephalus* spp. such as *R. sanguineus, R. appendiculatus, Rhipicephalus evertsi*), *Rhizoglyphus* spp; *Sarcoptes* spp. such as *S. Scabiei;* and Family Eriophyidae including *Aceria* spp. such as *A. sheldon, A. anthocoptes, Acallitus* spp; *Aculops* spp. such as *A. lycopersic, A. pelekassi Aculus* spp. such as *A. schlechtendali; Colomerus vitis, Epitrimerus pyri, Phyllocoptruta oleivora; Eriophytes ribis* and *Eriophyes* spp. such as *Eriophyes sheldoni* Family Tarsonemidae including *Hemitarsonemus* spp., *Phytonemus pallidus* and *Polyphagotarsonemus latus, Stenotarsonemus* spp. *Steneotarsonemus spinki;* Family Tenuipalpidae including *Brevipalpus* spp. such as *B. phoenicis,* Family Tetranychidae including *Eotetranychus* spp., *Eutetranychus* spp., *Oligonychus* spp., *Petrobia latens, Tetranychus* spp. such as *T. cinnabarinus, T. evansi, T. kanzawa, T, pacificus, T. phaseulus, T. telarius* and *T. urticae; Bryobia praetiosa; Panonychus* spp. such as *P. ulmi P. citri, Metatetranychus* spp. and *Oligonychus* spp. such as *O. pratensis, O. perseae*), *Vasates lycopersici; Raoiella indica,* Family Carpoglyphidae including *Carpoglyphus* spp; *Penthaleidae* spp. such as *Halotydeus destructor;* Family Demodicidae with species such a *Demodex* spp; Family Trombicidea including Trombicula spp; Family Macronyssidae including Ornothonyssus spp; Family Pyemotidae including *Pyemotes tritici; Tyrophagus putrescentiae;* Family Acaridae including *Acarus siro;* Family Araneida including *Latrodectus mactans, Tegenaria agrestis, Chiracanthium* sp, *Lycosa* sp *Achaearanea tepidariorum* and *Loxosceles reclusa.*

Pests from the Phylum Nematoda, for example, plant parasitic nematodes such as root-knot nematodes, *Meloidogyne* spp. such as *M. hapla, M. incognita, M. javanica;* cyst-forming nematodes, *Globodera* spp. such as *G. rostochiensis; Heterodera* spp. such as *H. avenae, H. glycines, H. schachtii, H. trifolii;* Seed gall nematodes, *Anguina* spp.; Stem and foliar nematodes, *Aphelenchoides* spp. such as *A. besseyi;* Sting nematodes, *Belonolaimus* spp. such as *B. longicaudatus;* Pine nematodes, *Bursaphelenchus* spp. such as *B. lignicolus, B. xylophilus;* Ring nematodes, *Criconema* spp.; *Criconemella* spp. such as *C. xenoplax* and *C. ornata;* and, *Criconemoides* spp. such as *Criconemoides informis; Mesocriconema* spp.; Stem and bulb nematodes, *Ditylenchus* spp. such as *D. destructor, D. dipsaci;* Awl nematodes, *Dolichodorus* spp.; Spiral nematodes, *Heliocotylenchus multicinctus;* Sheath and sheathoid nematodes, *Hemicycliophora* spp. and *Hemicriconemoides* spp.; *Hirshmanniella* spp.; Lance nematodes, *Hoploaimus* spp.; False rootknot nematodes, *Nacobbus* spp.; Needle nematodes, *Longidorus* spp. such as *L. elongatus;* Lesion nematodes, *Pratylenchus* spp. such as *P. brachyurus, P. neglectus, P. penetrans, P. curvitatus, P. goodeyi;* Burrowing nematodes, *Radopholus* spp. such as *R. similis; Rhadopholus* spp.; *Rhodopholus* spp.; Reniform nematodes, *Rotylenchus* spp. such as *R. robustus, R. reniformis; Scutellonema* spp.; Stubby-root nematode, *Trichodorus* spp. such as *T. obtusus, T. primitivus; Paratrichodorus* spp. such as *P. minor;* Stunt nematodes, *Tylenchorhynchus* spp. such as *T. claytoni T. dubius;* Citrus nematodes, *Tylenchulus* spp. such as *T. semipenetrans;* Dagger nematodes, *Xiphinema* spp.; and other plant parasitic nematode species.

Insects from the order Isoptera for example *Calotermes flavicollis, Coptotermes* spp. such as *C. formosanus, C. gestro C. acinaciformis; Cornitermes cumulans, Cryptotermes* spp. such as *C. brevis, C. cavifrons; Globitermes sulfureus, Heterotermes* spp. such as *H. aureus, H. longi-*

*ceps, H. tenuis; Leucotermes flavipes, Odontotermes* spp., *Incisitermes* spp. such as *I. minor, I. Snyder, Marginitermes hubbard, Mastotermes* spp. such as *M. darwiniensis Neocapritermes* spp. such as *N. opacus, N. parvus; Neotermes* spp., *Procornitermes* spp., *Zootermopsis* spp. such as *Z. angusticolis, Z. nevadensis, Reticulitermes* spp. such as *R. hesperus, R. tibialis, R. speratus, R. flavipes, R. grassei, R. lucifugus, R. santonensis, R. virginicus; Termes natalensis,*

Insects from the order *Blattaria* for example *Blatta* spp. such as *B. orientalis, B. lateralis; Blattella* spp. such as *B. asahinae, B. germanica; Leucophaea maderae, Panchlora nivea, Periplaneta* spp. such as *P. americana, P. australasiae, P. brunnea, P. fuligginosa, P. japonica; Supella longipalpa, Parcoblatta pennsylvanica, Eurycotis floridana, Pycnoscelus surinamensis*

Insects from the order Siphonoptera for example *Cediopsylla simples, Ceratophyllus* spp., *Ctenocephalides* spp. such as *C. felis, C. canis, Xenopsylla cheopis, Pulex irritans, Trichodectes canis, Tunga penetrans,* and *Nosopsyllus fasciatus,*

Insects from the order Thysanura for example *Lepisma saccharina, Ctenolepisma urbana,* and *Thermobia domestica,*

Pests from the class Chilopoda for example *Geophilus* spp., *Scutigera* spp. such as *Scutigera coleoptrata;*

Pests from the class Diplopoda for example *Blaniulus guttulatus, Julus* spp., *Narceus* spp., Pests from the class Symphyla for example *Scutigerella immaculata.*

Insects from the order Dermaptera, for example *Forficula auricularia,*

Insects from the order Collembola, for example *Onychiurus* spp. such as *Onychiurus armatus.*

Pests from the order Isopoda for example, *Armadillidium vulgare, Oniscus asellus, Porcellio scaber.*

Insects from the order Phthiraptera, for example *Damalinia* spp., *Pediculus* spp. such as *Pediculus humanus capitis, Pediculus humanus corporis, Pediculus humanus humanus, Pthirus pubis, Haematopinus* spp. such as *Haematopinus eurysternus, Haematopinus suis; Linognathus* spp. such as *Linognathus vituli Bovicola bovis, Menopon gallinae, Menacanthus stramineus* and *Solenopotes capillatus, Trichodectes* spp., Examples of further pest species which may be controlled by compounds of formula (I) include: from the Phylum Mollusca, class Bivalvia, for example, *Dreissena* spp.; class Gastropoda, for example, *Arion* spp., *Biomphalaria* spp., *Bulinus* spp., *Deroceras* spp., *Galba* spp., *Lymnaea* spp., *Oncomelania* spp., *Pomacea canaliclata, Succinea* spp.; from the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp. such as *Haemonchus contortus; Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercora lis, Stronyloides* spp., *Taenia saginata, Taenia solium, Trichinella spiralis, Trichinella nativa, Trichinella britovi, Trichinella nelsoni Trichinella pseudopsiralis, Trichostrongulus* spp., *Trichuris trichiura, Wuchereria bancrofti;*

Further examples of pest species which may be controlled by compounds of formula (I) include: *Anisoplia austriaca, Apamea* spp., *Austroasca viridigrisea, Baliothrips biformis, Caenorhabditis elegans, Cephus* spp., *Ceutorhynchus napi, Chaetocnema aridula, Chilo auricilius, Chilo indicus, Chilo polychrysus, Chortiocetes terminifera, Cnaphalocroci medinalis, Cnaphalocrosis* spp., *Colias eurytheme, Collops* spp., *Cornitermes cumulans, Creontiades* spp., *Cyclocephala* spp., *Dalbulus maidis, Deraceras reticulatum, Diatrea saccharalis, Dichelops furcatus, Dicladispa armigera, Diloboderus* spp. such as *Diloboderus abderus; Edessa* spp., *Epinotia* spp., Formicidae, *Geocoris* spp., *Globitermes sulfureus,* Gryllotalpidae, *Halotydeus destructor, Hipnodes bicolor, Hydrellia philippina, Julus* spp., *Laodelphax* spp., *Leptocorsia acuta, Leptocorsia oratorius, Liogenys fuscus, Lucillia* spp., *Lyogenys fuscus, Mahanarva* spp., *Maladera matrida, Marasmia* spp., *Mastotermes* spp., *Mealybugs, Megascelis* ssp, *Metamasius hemipterus, Microtheca* spp., *Mocis latipes, Murgantia* spp., *Mythemina separata, Neocapritermes opacus, Neocapritermes parvus, Neomegalotomus* spp., *Neotermes* spp., *Nymphula depunctalis, Oebalus pugnax, Orseolia* spp. such as *Orseolia oryzae; Oxycaraenus hyalinipennis, Plusia* spp., *Pomacea canaliculata, Procornitermes* ssp, *Procornitermes triacifer, Psylloides* spp., *Rachiplusia* spp., *Rhodopholus* spp., *Scaptocoris castanea, Scaptocoris* spp., *Scirpophaga* spp. such as *Scirpophaga incertulas, Scirpophaga innotata; Scotinophara* spp. such as *Scotinophara coarctata; Sesamia* spp. such as *Sesamia inferens, Sogaella frucifera, Solenapsis geminata, Spissistilus* spp., Stalk borer, *Stenchaetothrips biformis, Steneotarsonemus spinki, Sylepta derogata, Telehin licus, Trichostrongylus* spp.

The compounds of the present invention, including their salts, stereoisomers and tautomers, are particularly useful for controlling insects, preferably sucking or piercing and chewing and biting insects such as insects from the genera Lepidoptera, Coleoptera and Hemiptera, in particular Lepidoptera, Coleoptera and true bugs. The compounds of the present invention, including their salts, stereoisomers and tautomers, are moreover useful for controlling insects of the orders Thysanoptera, Diptera (especially flies, mosquitos), Hymenoptera (especially ants) and Isoptera (especially termites.

The compounds of the present invention, including their salts, stereoisomers and tautomers, are particularly useful for controlling insects of the orders Lepidoptera and Coleoptera.

The invention also relates to agrochemical compositions comprising an auxiliary and at least one compound I according to the invention.

An agrochemical composition comprises a pesticidally effective amount of a compound I. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the species to be controlled, the treated cultivated plant or material, the climatic conditions and the specific compound I used.

The compounds I, their N-oxides and salts can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6$^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl-naphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-subsituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-subsitiitued fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:
i) Water-soluble concentrates (SL, LS)
10-60 wt % of a compound I according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.
ii) Dispersible concentrates (DC)
5-25 wt % of a compound I according to the invention and 1-10 wt % dispersant (e.g. polyvinylpyrrolidone) are dissolved in organic solvent (e.g. cyclohexanone) ad 100 wt %. Dilution with water gives a dispersion.
iii) Emulsifiable concentrates (EC)
15-70 wt % of a compound I according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)
5-40 wt % of a compound I according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.
v) Suspensions (SC, OD, FS)
In an agitated ball mill, 20-60 wt % of a compound I according to the invention are comminuted with addition of 2-10 wt % dispersants and wetting agents (e.g. sodium lignosulfonate and alcohol ethoxylate), 0, 1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.
vi) Water-dispersible granules and water-soluble granules (WG, SG)
50-80 wt % of a compound I according to the invention are ground finely with addition of dispersants and wetting agents (e.g. sodium lignosulfonate and alcohol ethoxylate) ad 100 wt % and prepared as water-dispersible or water-soluble granules by means of technical appliances (e.g. extrusion, spray tower, fluidized bed). Dilution with water gives a stable dispersion or solution of the active substance.
vii) Water-dispersible powders and water-soluble powders (WP, SP, WS)
50-80 wt % of a compound I according to the invention are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.
viii) Gel (GW, GF)
In an agitated ball mill, 5-25 wt % of a compound I according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.
ix) Microemulsion (ME)
5-20 wt % of a compound I according to the invention are added to 5-30 wt % organic solvent blend (e.g. fatty acid dimethylamide and cyclohexanone), 10-25 wt % surfactant blend (e.g. alkohol ethoxylate and arylphenol ethoxylate), and water ad 100%. This mixture is stirred for 1 h to produce spontaneously a thermodynamically stable microemulsion.
x) Microcapsules (CS)
An oil phase comprising 5-50 wt % of a compound I according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of a polyurea microcapsules. The monomers amount to 1-10 wt %. The wt % relate to the total CS composition.
xi) Dustable powders (DP, DS)
1-10 wt % of a compound I according to the invention are ground finely and mixed intimately with solid carrier (e.g. finely divided kaolin) ad 100 wt %.
xii) Granules (GR, FG)
0.5-30 wt % of a compound I according to the invention is ground finely and associated with solid carrier (e.g. silicate) ad 100 wt %. Granulation is achieved by extrusion, spray-drying or the fluidized bed.
xiii) Ultra-low volume liquids (UL)
1-50 wt % of a compound I according to the invention are dissolved in organic solvent (e.g. aromatic hydrocarbon) ad 100 wt %.

The compositions types i) to xiii) may optionally comprise further auxiliaries, such as 0, 1-1 wt % bactericides, 5-15 wt % anti-freezing agents, 0, 1-1 wt % anti-foaming agents, and 0, 1-1 wt % colorants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e.g. components comprising compounds I and/or active substances from the groups M) or F) (see below), may be mixed by the user in a spray tank and further auxiliaries and additives may be added, if appropriate.

In a further embodiment, either individual components of the composition according to the invention or partially premixed components, e. g. components comprising compounds I and/or active substances from the groups M.1 to M.UN.X or F.I to F.XIII, can be applied jointly (e.g. after tank mix) or consecutively.

The following list M of pesticides, grouped and numbered according the Mode of Action Classification of the Insecticide Resistance Action Committee (IRAC), together with which the compounds according to the invention can be used and with which potential synergistic effects might be produced, is intended to illustrate the possible combinations, but not to impose any limitation:

M.1 Acetylcholine esterase (AChE) inhibitors from the class of

M.1A carbamates, for example aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of M.1B organophosphates, for example acephate, azamethiphos, azinphos-ethyl, azinphosmethyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

M.2. GABA-gated chloride channel antagonists such as:
M.2A cyclodiene organochlorine compounds, as for example endosulfan or chlordane; or M.2B fiproles (phenylpyrazoles), as for example ethiprole, fipronil, flufiprole, pyrafluprole and pyriprole;

M.3 Sodium channel modulators from the class of

M.3A pyrethroids, for example acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, heptafluthrin, imiprothrin, meperfluthrin, metofluthrin, momfluorothrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; or M.3B sodium channel modulators such as DDT or methoxychlor;

M.4 Nicotinic acetylcholine receptor agonists (nAChR) from the class of

M.4A neonicotinoids, for example acetamiprid, chlothianidin, cycloxaprid, dinotefuran, imidacloprid, nitenpyram, thiacloprid and thiamethoxam; or the compounds M.4A.2: (2E-)-1-[(6-Chloropyridin-3-yl)methyl]-N'-nitro-2-pentylidenehydrazinecarboximidamide; or M4.A.3: 1-[(6-Chloropyridin-3-yl)methylmethyl-8-nitro-5-propoxy-1,2,3,5,6,7-hexahydroimidazo[1,2-a]pyridine;

or from the class M.4B nicotine;

M.5 Nicotinic acetylcholine receptor allosteric activators from the class of spinosyns, for example spinosad or spinetoram;

M.6 Chloride channel activators from the class of avermectins and milbemycins, for example abamectin, emamectin benzoate, ivermectin, lepimectin or milbemectin;

M.7 Juvenile hormone mimics, such as

M.7A juvenile hormone analogues as hydroprene, kinoprene and methoprene; or others as M.7B fenoxycarb or M.7C pyriproxyfen;

M.8 miscellaneous non-specific (multi-site) inhibitors, for example

M.8A alkyl halides as methyl bromide and other alkyl halides, or

M.8B chloropicrin, or M.8C sulfuryl fluoride, or M.8D borax, or M.8E tartar emetic;

M.9 Selective homopteran feeding blockers, for example M.9B pymetrozine, or M.9C flonicamid;

M.10 Mite growth inhibitors, for example

M.10A clofentezine, hexythiazox and diflovidazin, or M.10B etoxazole;

M.11 Microbial disruptors of insect midgut membranes, for example *bacillus thuringiensis* or *bacillus sphaericus* and the insecticdal proteins they produce such as *bacillus thuringiensis* subsp. *israelensis, bacillus sphaericus, bacillus thuringiensis* subsp. *aizawai, bacillus thuringiensis* subsp. *kurstaki* and *bacillus thuringiensis* subsp. *tenebrionis*, or the Bt crop proteins: Cry1Ab, Cry1Ac, Cry1 Fa, Cry2Ab, mCry3A, Cry3Ab, Cry3Bb and Cry34/35Ab1;

M.12 Inhibitors of mitochondrial ATP synthase, for example M.12A diafenthiuron, or M.12B organotin miticides such as azocyclotin, cyhexatin or fenbutatin oxide, or M.12C propargite, or M.12D tetradifon;

M.13 Uncouplers of oxidative phosphorylation via disruption of the proton gradient, for example chlorfenapyr, DNOC or sulfluramid;

M.14 Nicotinic acetylcholine receptor (nAChR) channel blockers, for example nereistoxin analogues as bensultap, cartap hydrochloride, thiocyclam or thiosultap sodium;

M.15 Inhibitors of the chitin biosynthesis type 0, such as benzoylureas as for example bistrifluron, chlorfluazuron, diflubenzuron, flucycloxuron, flufenoxuron, hexaflumuron, lufenuron, novaluron, noviflumuron, teflubenzuron or triflumuron;

M.16 Inhibitors of the chitin biosynthesis type 1, as for example buprofezin;

M.17 Moulting disruptors, Dipteran, as for example cyromazine;

M.18 Ecdyson receptor agonists such as diacylhydrazines, for example methoxyfenozide, tebufenozide, halofenozide, fufenozide or chromafenozide;

M.19 Octopamin receptor agonists, as for example amitraz;

M.20 Mitochondrial complex III electron transport inhibitors, for example

M.20A hydramethylnon, or M.20B acequinocyl, or M.20C fluacrypyrim;

M.21 Mitochondrial complex I electron transport inhibitors, for example

M.21A METI acaricides and insecticides such as fenazaquin, fenpyroximate, pyrimidifen, pyridaben, tebufenpyrad or tolfenpyrad, or M.21B rotenone;

M.22 Voltage-dependent sodium channel blockers, for example

M.22A indoxacarb, or M.22B metaflumizone, or M.22B.1: 2-[2-(4-Cyanophenyl)-1-[3-(trifluoromethyl)phenyl]ethylidene]-N-[4-(difluoromethoxy)phenyl]-hydrazinecarboxamide or M.22B.2: N-(3-Chloro-2-methylphenyl)-2-[(4-chlorophenyl)[4-[methyl(methylsulfonyl)amino]phenyl]methylene]-hydrazinecarboxamide;

M.23 Inhibitors of the of acetyl CoA carboxylase, such as Tetronic and Tetramic acid derivatives, for example spirodiclofen, spiromesifen or spirotetramat;

M.24 Mitochondrial complex IV electron transport inhibitors, for example

M.24A phosphine such as aluminium phosphide, calcium phosphide, phosphine or zinc phosphide, or M.24B cyanide;

M.25 Mitochondrial complex II electron transport inhibitors, such as beta-ketonitrile derivatives, for example cyenopyrafen or cyflumetofen;

M.28 Ryanodine receptor-modulators from the class of diamides, as for example flubendiamide, chlorantraniliprole (Rynaxypyr®), cyantraniliprole (Cyazypyr®), tetraniliprole or the phthalamide compounds M.28.1: (R)-3-Chlor-N1-{2-methyl-4-[1,2,2,2-tetrafluor-1-(trifluormethyl)ethyl]phenyl}-N2-(1-methyl-2-methylsulfonylethyl)phthalamid and M.28.2: (S)-3-Chlor-N1-{2-methyl-4-[1,2,2,2-tetrafluor-1-(trifluormethyl)ethyl]phenyl}-N2-(1-methyl-2-methylsulfonylethyl)phthalamid, or the compound M.28.3: 3-bromo-N-{2-bromo-4-chloro-6-[(1-cyclopropylethyl)carbamoyl]phenyl}-1-(3-chlorpyridin-2-yl)-1H-pyrazole-5-carboxamide (proposed ISO name: cyclaniliprole), or the compound M.28.4: methyl-2-[3,5-dibromo-2-({[3-bromo-1-(3-chlorpyridin-2-yl)-1H-pyrazol-5-yl]carbonyl}amino)benzoyl]-1,2-dimethylhydrazinecarboxylate; or a compound selected from M.28.5a) to M.28.5d) and M.28.5h) to M.28.5l):

M.28.5a) N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide;

M.28.5b) N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide;

M.28.5c) N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide;

M.28.5d) N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide;

M.28.5h) N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide;

M.28.5i) N-[2-(5-Amino-1,3,4-thiadiazol-2-yl)-4-chloro-6-methylphenyl]-3-bromo-1-(3-chloro-2-pyridinyl)-1H-pyrazole-5-carboxamide;

M.28.5j) 3-Chloro-1-(3-chloro-2-pyridinyl)-N-[2,4-dichloro-6-[[(1-cyano-1-methylethyl)amino]carbonyl]phenyl]-1H-pyrazole-5-carboxamide;

M.28.5k) 3-Bromo-N-[2,4-dichloro-6-(methylcarbamoyl)phenyl]-1-(3,5-dichloro-2-pyridyl)-1H-pyrazole-5-carboxamide;

M.28.5l) N-[4-Chloro-2-[[(1,1-dimethylethyl)amino]carbonyl]-6-methylphenyl]-1-(3-chloro-2-pyridinyl)-3-(fluoromethoxy)-1H-pyrazole-5-carboxamide;

or a compound selected from

M.28.6: cyhalodiamide; or

M.29. insecticidal active compounds of unknown or uncertain mode of action, as for example afidopyropen, afoxolaner, azadirachtin, amidoflumet, benzoximate, bifenazate, broflanilide, bromopropylate, chinomethionat, cryolite, dicloromezotiaz, dicofol, flufenerim, flometoquin, fluensulfone, fluhexafon, fluopyram, flupyradifurone, fluralaner, metoxadiazone, piperonyl butoxide, pyflubumide, pyridalyl, pyrifluquinazon, sulfoxaflor, tioxazafen, triflumezopyrim, or the compounds M.29.3: 11-(4-chloro-2,6-dimethylphenyl)-12-hydroxy-1,4-dioxa-9-azadispiro[4.2.4.2]-tetradec-11-en-10-one, or the compound M.29.4: 3-(4'-fluoro-2,4-dimethylbiphenyl-3-yl)-4-hydroxy-8-oxa-1-azaspiro[4.5]dec-3-en-2-one, or the compound M.29.5: 1-[2-fluoro-4-methyl-5-[(2,2,2-trifluoroethyl)sulfinyl]phenyl]-3-(trifluoromethyl)-1H-1,2,4-triazole-5-amine, or actives on basis of *bacillus firmus* (Votivo, I-1582); or a compound selected from the group of M.29.6, wherein the compound is selected from M.29.6a) to M.29.6k):

M.29.6a) (E/Z)—N-[1-[(6-chloro-3-pyridyl)methyl]-2-pyridylidene]-2,2,2-trifluoro-acetamide;

M.29.6b) (E/Z)—N-[1-[(6-chloro-5-fluoro-3-pyridyl)methyl]-2-pyridylidene]-2,2,2-trifluoro-acetamide;

M. 29.6c) (E/Z)-2,2,2-trifluoro-N-[1-[(6-fluoro-3-pyridyl)methyl]-2-pyridylidene]acetamide;

M. 29.6d) (E/Z)—N-[1-[(6-bromo-3-pyridyl)methyl]-2-pyridylidene]-2,2,2-trifluoro-acetamide;

M. 29.6e) (E/Z)—N-[1-[1-(6-chloro-3-pyridyl)ethyl]-2-pyridylidene]-2,2,2-trifluoro-acetamide;

M. 29.6f) (E/Z)—N-[1-[(6-chloro-3-pyridyl)methyl]-2-pyridylidene]-2,2-difluoro-acetamide;

M. 29.6g) (E/Z)-2-chloro-N-[1-[(6-chloro-3-pyridyl)methyl]-2-pyridylidene]-2,2-difluoro-acetamide;

M. 29.6h) (E/Z)—N-[1-[(2-chloropyrimidin-5-yl)methyl]-2-pyridylidene]-2,2,2-trifluoro-acetamide;

M. 29.6i) (E/Z)—N-[1-[(6-chloro-3-pyridyl)methyl]-2-pyridylidene]-2,2,3,3,3-pentafluoro-propanamide.);

M. 29.6j) N-[1-[(6-chloro-3-pyridyl)methyl]-2-pyridylidene]-2,2,2-trifluoro-thioacetamide or of the compound M. 29.6k) N-[1-[(6-chloro-3-pyridyl)methyl]-2-pyridylidene]-2,2,2-trifluoro-N'-isopropyl-acetamidine or M. 29.8: fluazaindolizine; or M. 29.9.a): 4-[5-(3,5-dichlorophenyl)-5-(trifluoromethyl)-4H-isoxazol-3-yl]-2-methyl-N-(1-oxothietan-3-yl)benzamide; or M.29.9.b): fluxametamide; or M. 29.10: 5-[3-[2,6-dichloro-4-(3,3-dichloroallyloxy)phenoxy]propoxy]-1H-pyrazole; or a compound selected from the group of M.UN.11, wherein the compound is selected from M.UN.11b) to M.UN.11p):

M. 29.11.b) 3-(benzoylmethylamino)-N-[2-bromo-4-[1,2,2,3,3,3-hexafluoro-1-(trifluoromethyl)propyl]-6-(trifluoromethyl)phenyl]-2-fluoro-benzamide;

M. 29.11.c) 3-(benzoylmethylamino)-2-fluoro-N-[2-iodo-4-[1,2,2,2-tetrafluoro-1-(trifluoromethyl)ethyl]-6-(trifluoromethyl)phenyl]-benzamide;

M. 29.11.d) N-[3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide;

M. 29.11.e) N-[3-[[[2-bromo-4-[1,2,2,2-tetrafluoro-1-(trifluoromethyl)ethyl]-6-(trifluoromethyl)phenyl]amino]carbonyl]-2-fluorophenyl]-4-fluoro-N-methyl-benzamide;

M. 29.11.f) 4-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide;

M. 29.11.g) 3-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide;

M. 29.11.h) 2-chloro-N-[3-[[[2-iodo-4-[1,2,2,2-tetrafluoro-1-(trifluoromethyl)ethyl]-6-(trifluoromethyl)phenyl]amino]carbonyl]phenyl]-3-pyridinecarboxamide;

M. 29.11.i) 4-cyano-N-[2-cyano-5-[[2,6-dibromo-4-[1,2,2,3,3,3-hexafluoro-1-(trifluoromethyl)propyl]phenyl]carbamoyl]phenyl]-2-methyl-benzamide;

M. 29.11.j) 4-cyano-3-[(4-cyano-2-methyl-benzoyl)amino]-N-[2,6-dichloro-4-[1,2,2,3,3,3-hexafluoro-1-(trifluoromethyl)propyl]phenyl]-2-fluoro-benzamide;

M. 29.11.k) N-[5-[[2-chloro-6-cyano-4-[1,2,2,3,3,3-hexafluoro-1-(trifluoromethyl)propyl]phenyl]carbamoyl]-2-cyano-phenyl]-4-cyano-2-methyl-benzamide;

M. 29.11.l) N-[5-[[2-bromo-6-chloro-4-[2,2,2-trifluoro-1-hydroxy-1-(trifluoromethyl)ethyl]phenyl]carbamoyl]-2-cyano-phenyl]-4-cyano-2-methyl-benzamide;

M. 29.11.m) N-[5-[[2-bromo-6-chloro-4-[1,2,2,3,3,3-hexafluoro-1-(trifluoromethyl)propyl]phenyl]carbamoyl]-2-cyano-phenyl]-4-cyano-2-methyl-benzamide;

M. 29.11.n) 4-cyano-N-[2-cyano-5-[[2,6-dichloro-4-[1,2,2,3,3,3-hexafluoro-1-(trifluoromethyl)propyl]phenyl]carbamoyl]phenyl]-2-methyl-benzamide;

M. 29.11.o) 4-cyano-N-[2-cyano-5-[[2,6-dichloro-4-[1,2,2,2-tetrafluoro-1-(trifluoromethyl)ethyl]phenyl]carbamoyl]phenyl]-2-methyl-benzamide;

M. 29.11.p) N-[5-[[2-bromo-6-chloro-4-[1,2,2,2-tetrafluoro-1-(trifluoromethyl)ethyl]phenyl]carbamoyl]-2-cyano-phenyl]-4-cyano-2-methyl-benzamide; or a compound selected from the group of M. 29.12, wherein the compound is selected from M. 29.12a) to M. 29.12m):

M. 29.12.a) 2-(1,3-Dioxan-2-yl)-6-[2-(3-pyridinyl)-5-thiazolyl]-pyridine;

M. 29.12.b) 2-[6-[2-(5-Fluoro-3-pyridinyl)-5-thiazolyl]-2-pyridinyl]-pyrimidine;

M. 29.12.c) 2-[6-[2-(3-Pyridinyl)-5-thiazolyl]-2-pyridinyl]-pyrimidine;

M. 29.12.d) N-Methylsulfonyl-6-[2-(3-pyridyl)thiazol-5-yl]pyridine-2-carboxamide M. 29.12.e) N-Methylsulfonyl-6-[2-(3-pyridyl)thiazol-5-yl]pyridine-2-carboxamide M. 29.12.f) N-Ethyl-N-[4-methyl-2-(3-pyridyl)thiazol-5-yl]-3-methylthio-propanamide M. 29.12.g) N-Methyl-N-[4-methyl-2-(3-pyridyl)thiazol-5-yl]-3-methylthio-propanamide M. 29.12.h) N,2-Dimethyl-N-[4-methyl-2-(3-pyridyl)thiazol-5-yl]-3-methylthio-propanamide M. 29.12.i) N-Ethyl-2-methyl-N-[4-methyl-2-(3-pyridyl)thiazol-5-yl]-3-methylthio-propanamide M. 29.12.j) N-[4-Chloro-2-(3-pyridyl)thiazol-5-yl]-N-ethyl-2-methyl-3-methylthio-propanamide M. 29.12.k) N-[4-Chloro-2-(3-pyridyl)thiazol-5-yl]-N,2-dimethyl-3-methylthio-propanamide M. 29.12.l) N-[4-Chloro-2-(3-pyridyl)thiazol-5-yl]-N-methyl-3-methylthio-propanamide M. 29.12.m) N-[4-Chloro-2-(3-pyridyl)thiazol-5-yl]-N-ethyl-3-methylthio-propanamide; or the compounds M. 29.14a) 1-[(6-Chloro-3-pyridinyl)methyl]-1,2,3,5,6,7-hexahydro-5-methoxy-7-methyl-8-nitro-imidazo[1,2-a]pyridine; or M. 29.14b) 1-[(6-Chloropyridin-3-yl)methyl]-7-methyl-8-nitro-1,2,3,5,6,7-hexahydroimidazo[1,2-a]pyridin-5-ol; or the compounds M.29.16a) 1-isopropyl-N,5-dimethyl-N-pyridazin-4-yl-pyrazole-4-carboxamide; or M.29.16b) 1-(1,2-dimethylpropyl)-N-ethyl-5-methyl-N-pyridazin-4-yl-pyrazole-4-carboxamide; M.29.16c) N,5-dimethyl-N-pyridazin-4-yl-1-(2,2,2-trifluoro-1-methyl-ethyl)pyrazole-4-carboxamide; M.29.16d) 1-[1-(1-cyanocyclopropyl)ethyl]-N-ethyl-5-methyl-N-pyridazin-4-yl-pyrazole-4-carboxamide; M.29.16e) N-ethyl-1-(2-fluoro-1-methyl-propyl)-5-methyl-N-pyridazin-4-yl-pyrazole-4-carboxamide; M.29.16f) 1-(1,2-dimethylpropyl)-N,5-dimethyl-N-pyridazin-4-yl-pyrazole-4-carboxamide; M.29.16g) 1-[1-(1-cyanocyclopropyl)ethyl]-N,5-dimethyl-N-pyridazin-4-yl-pyrazole-4-carboxamide;

M.29.16h) N-methyl-1-(2-fluoro-1-methyl-propyl)-5-methyl-N-pyridazin-4-yl-pyrazole-4-carboxamide;

M.29.16i) 1-(4,4-difluorocyclohexyl)-N-ethyl-5-methyl-N-pyridazin-4-yl-pyrazole-4-carboxamide; or M.29.16j) 1-(4,4-difluorocyclohexyl)-N,5-dimethyl-N-pyridazin-4-yl-pyrazole-4-carboxamide, or M.29.17 a compound selected from the compounds M.29.17a) to M.29.17j): M.29.17a) N-(1-methylethyl)-2-(3-pyridinyl)-2H-indazole-4-carboxamide; M.29.17b) N-cyclopropyl-2-(3-pyridinyl)-2H-indazole-4-carboxamide; M.29.17c) N-cyclohexyl-2-(3-pyridinyl)-2H-indazole-4-carboxamide; M.29.17d) 2-(3-pyridinyl)-N-(2,2,2-trifluoroethyl)-2H-indazole-4-carboxamide; M.29.17e) 2-(3-pyridinyl)-N-[(tetrahydro-2-furanyl)methyl]-2H-indazole-5-carboxamide; M.29.17f) methyl 2-[[2-(3-pyridinyl)-2H-indazol-5-yl]carbonyl]hydrazinecarboxylate; M.29.17g) N-[(2,2-difluorocyclopropyl)methyl]-2-(3-pyridinyl)-2H-indazole-5-carboxamide; M.29.17h) N-(2,2-difluoropropyl)-2-(3-pyridinyl)-2H-indazole-5-carboxamide;

M.29.17i) 2-(3-pyridinyl)-N-(2-pyrimidinylmethyl)-2H-indazole-5-carboxamide; M.29.17j) N-[(5-methyl-2-pyrazinyl)methyl]-2-(3-pyridinyl)-2H-indazole-5-carboxamide, or M.29.18 a compound selected from the compounds M.29.18a) to M.29.18d): M.29.18a) N-[3-chloro-1-(3-pyridyl)pyrazol-4-yl]-N-ethyl-3-(3,3,3-trifluoropropylsulfanyl)propanamide; M.29.18b) N-[3-chloro-1-(3-pyridyl)pyrazol-4-yl]-N-ethyl-3-(3,3,3-trifluoropropylsulfinyl)propanamide; M.29.18c) N-[3-chloro-1-(3-pyridyl)pyrazol-4-yl]-3-[(2,2-difluorocyclopropyl)methylsulfanyl]-N-ethyl-propanamide;

M.29.18d) N-[3-chloro-1-(3-pyridyl)pyrazol-4-yl]-3-[(2,2-difluorocyclopropyl)methylsulfinyl]-N-ethyl-propanamide; or the compound M.29.19 sarolaner, or the compound
M.29.20 lotilaner.

The commercially available compounds of the group M listed above may be found in The Pesticide Manual, 16th Edition, C. MacBean, British Crop Protection Council (2013) among other publications.

The online Pesticide Manual is updated regularly and is accessible through http://bcpcdata.com/pesticide-manual.html.

Another online data base for pesticides providing the ISO common names is http://www.alanwood.net/pesticides.

The M.4 neonicotinoid cycloxaprid is known from WO2010/069266 and WO2011/069456, and the neonicotinoid M.4A.2, sometimes also to be named as guadipyr, is known from WO2013/003977, and the neonicotinoid M.4A.3. (approved as paichongding in China) is known from WO2007/101369. The metaflumizone analogue M.22B.1 is described in CN 10171577 and the analogue M.22B.2 in CN102126994. The phthalamides M.28.1 and M.28.2 are both known from WO 2007/101540. The anthranilamide M.28.3 has been described in WO2005/077934. The hydrazide compound M.28.4 has been described in WO 2007/043677. The anthranilamides M.28.5a) to M.28.5d) and M.28.5h) are described in WO 2007/006670, WO2013/024009 and WO2013/024010, the anthranilamide compound M.28.5i) is described in WO2011/085575, the compound M.28.5j) in WO2008/134969, the compound M.28.5k) in US2011/046186 and the compound M.28.5l) in WO2012/034403. The diamide compound M.28.6 can be found in WO2012/034472.

The spiroketal-substituted cyclic ketoenol derivative M.29.3 is known from WO2006/089633 and the biphenyl-substituted spirocyclic ketoenol derivative M.29.4 from WO2008/067911. The triazoylphenylsulfide M.29.5 has been described in WO2006/043635, and biological control agents on basis of *bacillus firmus* are described in WO2009/124707.

The compounds M.29.6a) to M. 29.6i) listed under M. 29.6 have been described in WO2012/029672 and compounds M. 29.6j) and M. 29.6k) in WO2013/129688. The nematicide compound M. 29.8 is known from WO2013/055584. The isoxazoline M.29.9.a) is described in WO2013/050317. The isoxazoline M.29.9.b) is described in WO2014/126208. The pyridalyl-type analogue M. 29.10 is known from WO2010/060379. The carboxamide compounds broflanilide and M. 29.11.b) to M. 29.11.h) can be prepared as described in WO 2010/018714 and the carboxamide M. 29.11i) to M. 29.11.p) are described WO2010/127926. The pyridylthiazoles M. 29.12.a) to M. 29.12.c) are known from WO2010/006713, M. 29.12.d) and and M.29.12.e) are known from WO2012/000896 and M. 29.12.f) to M. 29.12.m) from WO2010/129497. The compounds M. 29.14a) and M. 29.14b) are known from WO2007/101369. The pyrazoles M.29.16.a) to M.29.16h) are described in WO2010/034737, WO2012/084670, and WO2012/143317, respectively, and the pyrazoles M.29.16i) and M.29.16j) are described in U.S. 61/891,437. The pyridinylindazoles M.29.17a) to M.29.17.j) are described in WO2015/038503. The pyridylpyrazoles M.29.18a) to M.29.18d) are described in US2014/0213448. The isoxazoline M.29.19 is described in WO2014/036056. The isoxazoline M.29.20 is known from WO2014/090918.

Especially combinations of compounds of the invention with fiproles, neonictinoids or pyrethroids may possibly exhibit synergistic control of stinkbugs (according to the Colby formula), in particular *Euschistus*, e.g. *Euschistus heros*.

The following list of fungicides, in conjunction with which the compounds according to the invention can be used, is intended to illustrate the possible combinations but does not limit them:

F.I) A) Respiration Inhibitorsinhibitors

F.I-1) Inhibitors of complex III at Qo site:
strobilurins: azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, triclopyricarb/chlorodincarb, trifloxystrobin, 2-[2-(2,5-dimethyl-phenoxymethyl)-phenyl]-3-methoxyacrylic acid methyl ester and 2 (2-(3-(2,6-dichlorophenyl)-1-methyl-allylideneaminooxymethyl)-phenyl)-2-methoxyimino-N methyl-acetamide; oxazolidinediones and imidazolinones: famoxadone, fenamidone;

F.I-2) Inhibitors of complex II (e.g. carboxamides):
carboxanilides: benodanil, benzovindiflupyr, bixafen, boscalid, carboxin, fenfuram, fenhexamid, fluopyram, flutolanil, furametpyr, isopyrazam, isotianil, mepronil, oxycarboxin, penflufen, penthi-opyrad, sedaxane, tecloftalam, thifluzamide, tiadinil, 2-amino-4 methyl-thiazole-5-carboxanilide, N-(3',4',5' trifluorobiphenyl-2 yl)-3-difluoromethyl-1-methyl-1H-pyrazole-4 carboxamide (fluxapy-roxad), N-(4'-trifluoromethylthiobiphenyl-2-yl)-3 difluoromethyl-1-methyl-1H pyrazole-4-carboxamide, N-(2-(1,3,3-trimethyl-butyl)-phenyl)-1,3-dimethyl-5 fluoro-1H-pyrazole-4 carbox-amide, 3 (difluoromethyl)-1-methyl-N-(1,1,3-trimethylindan-4-yl)pyrazole-4-carboxamide, 3 (trifluoromethyl)-1-methyl-N-(1,1,3-trimethylindan-4-yl) pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide, 3 (difluoromethyl)-1-methyl-N-(1,1,3-trimethyl¬indan-4-yl)pyrazole-4-carboxamide, 3 (trifluoromethyl)-1-methyl-N-(1,1,3-trimethyl¬indan-4-yl) pyrazole-4-carboxamide, 1,3-dimethyl-N-(1,1,3-trimethyl-indan-4-yl)pyr¬azole-4-carboxamide, 3-(trifluorometh¬yl)-1,5-dimethyl-N-(1,1,3-trimethylindan-4-yl)-pyrazole-4-carboxamide, 3-(difluoro¬methyl)-1,5-dimethyl-N-(1,1,3-trimethylindan-4 yl)pyrazole-4-carboxamide, 1,3,5-tri-methyl-N-(1,1,3-trimethylindan-4-yl) pyrazole-4-carboxamide;

F.I-3) Inhibitors-Inhibitors of complex III at Qo site (e. g. strobilurins): azoxystrobin (A.1.1), coumeth¬oxy¬strobin (A.1.2), coumoxystrobin (A.1.3), dimoxystrobin (A.1.4), enestroburin (A.1.5), fenaminstrobin (A.1.6), fenoxy¬strobin/flufenoxystrobin (A.1.7), fluoxastro¬bin (A.1.8), kresoxim-methyl (A.1.9), mandestrobin (A.1.10), meto¬minostrobin (A.1.11), orysastrobin (A.1.12), picoxy-.strobin (A.1.13), pyraclostrobin (A.1.14), pyrametostrobin (A.1.15), pyraoxystrobin (A.1.16), trifloxystrobin (A.1.17), 2 (2-(3-(2,6-dihchlorophenyl)-1-methyl-allylidene¬aminooxy¬methyl)-phenyl)-2-methoxyimino-N methyl-acetamide (A.1.18), pyribencarb (A.1.19), triclopyricarb/chlorodin-carb (A.1.20), famoxadone (A.1.21), fenamidone (A.1.21), methyl-N-[2-[(1,4-dimethyl-5-phenyl-pyrazol-3-yl)oxylmethyl]phenyl]-N-methoxy-carbamate (A.1.22), 1-[3-chloro-2-[[1-(4-chlorophenyl)-1H-pyrazol-3-yl]oxymethyl] phenyl]-4-methyl-tetrazol-5-one (A.1.23), 1-[3-bromo-2-[[1-(4-chlorophenyl)pyrazol-3-yl]-oxy-methyl]phenyl]-4-methyl-tetrazol-5-one (A.1.24), 1-[2-[[1-(4-chlorophenyl)pyrazol-3-yl]oxy-methyl]-3-methyl-phenyl]-4-methyl-tetrazol-5-one (A.1.25), 1-[2-[[1-(4- chlorophenyl)py-razol-3-yl]oxymethyl]-3-fluoro-phenyl]-4-methyl-tetrazol-5-one (A.1.26), 1-[2-[[1-(2,4-dichloro-phenyl)pyrazol-3-yl]oxymethyl]-3-fluoro-phenyl]-4-methyl-tetrazol-5-one (A.1.27), 1-[2-[[4-(4-chlorophenyl)thiazol-2-yl]oxymethyl]-3-methyl-phenyl]-4-methyl-tetrazol-5-one (A.1.28), 1-[3-chloro-2-[[4-(p-tolyl)thiazol-2-yl]oxymethyl] phenyl]-4-methyl-tetrazol-5-one (A.1.29), 1-[3-cyclopropyl-2-[[2-methyl-4-(1-methylpyrazol-3-yl)phenoxy]-methyl]phenyl]-4 methyl-tetrazol-5-one (A.1.30), 1-[3-(difluoromethoxy)-2-[[2-methyl-4-(1 methyl-pyrazol-3 yl)phenoxy]methyl]phenyl]-4-methyl-tetrazol-5-one (A.1.31), 1-methyl-4-[3-methyl-2 [[2 methyl-4-(1-methylpyrazol-3-yl)phenoxy]methyl]phenyl]tetrazol-5-one (A.1.32), 1-me-thyl-4-[3-methyl-2-[[1-[3-(trifluoromethyl)phenyl]-ethylideneamino]oxymethyl]phenyl]-tetrazol-5 one (A.1.33), (Z,2E)-5-[1-(2,4-dichlorophenyl)pyrazol-3-yl]-oxy-2-methoxyimino-N,3-dimethyl-pent-3-enamide (A.1.34), (Z,2E)-5-[1-(4-chlorophenyl)pyrazol-3-yl]oxy-2-methoxyimino-N,3-dimethyl-pent-3-enamide (A.1.35), (Z,2E)-5-[1-(4-chloro-2-fluoro-phenyl)pyrazol-3-yl]oxy-2-methoxyimino-N,3-dimethyl-pent-3-enamide (A.1.36), inhibitors of complex III at Qi site: cyazofamid, (A.2.1), amisulbrom, (A.2.2), [(3S,6S,7R,8R)-8-benz-yl-3-[(3-acetoxy-4 methoxy-pyridine-2-carbonyl)amino]-6-methyl-4,9-dioxo-1,5-di-oxonan-7-yl] 2 methylpropanoate, (A.2.3), [(3S,6S,7R,8R)-8-benzyl-3-[[3-(acetoxymeth-oxy)-4-methoxy-pyridine-2 carbonyl]amino]-6-methyl-4,9-dioxo-1,5-dioxonan-7-yl] 2 methylpropanoate, (A.2.4), [(3S,6S,7R,8R)-8-benzyl-3-[(3-isobut-oxycarbonyloxy-4-meth-oxy-pyri-dine-2 carbonyl]amino]-6-methyl-4,9-dioxo-1,5-dioxonan-7-yl] 2-methylpro-panoate, (A.2.5), [(3S,6S,7R,8R)-8-benzyl-3-[[3-(1,3-ben-zodioxol-5-ylmethoxy)-4-methoxy-pyri-dine-2-car-bonyl]amino]-6-methyl-4,9-di-oxo-1,5-dioxonan-7-yl] 2-methyl-propanoate, (A.2.6); (3S,6S,7R,8R)-3-[[(3-hydroxy-4-methoxy-2-pyridinyl)carbonyl]amino]-6-methyl-4,9-dioxo-8-(phenylmethyl (phenyl-methyl)-1,5-dioxonan-7-yl 2-methylpropanoate; (A.2.7), (3S,6S,7R,8R)-8-benzyl-3 [3 [(isobutyryloxy)methoxy]-4-methoxypicolinamido]-6-methyl-4,9-dioxo-1,5-dioxonan-7-yl isobutyrate (A.2.8);

F.I-4) Other respiration inhibitors (complex I, uncouplers) diflumetorim;—inhibitors of com-plex II (e. g. carboxamides): benodanil (A.3.1), benzovindiflupyr (A.3.2), bixafen (A.3.3), boscalid (A.3.4), carboxin (A.3.5), fen-furam (A.3.6), fluopyram (A.3.7), flutolanil (A.3.8), fluxapyroxad (A.3.9), furametpyr (A.3.10), isofetamid (A.3.11), iso-pyrazam (A.3.12), mepronil (A.3.13), oxycarboxin (A.3.14), penflufen (A.3.14), penthiopyrad (A.3.15), sedaxane (A.3.16), tecloftalam (A.3.17), thifluz-amide (A.3.18), N-(4'-trifluoromethylthiobiphenyl-2-yl)-3 difluoromethyl-1-methyl-1H pyrazole-4-carboxamide (A.3.19), N-(2-(1,3,3-trimethyl-butyl)-phenyl)-1,3-dimethyl-5 fluoro-1H-pyr-azole-4 carboxamide (A.3.20), 3 (difluoromethyl)-1-methyl-N-(1,1,3-trimethyl-indan-4-yl)pyrazole-4-carboxamide (A.3.21), 3 (trifluoromethyl)-1-methyl-N-(1,1,3-trimethyl-indan-4-yl)pyrazole-4-carboxamide (A.3.22), 1,3-dimethyl-N-(1,1,3-trimethylindan-4-yl)pyr-azole-4-carboxamide (A.3.23), 3-(trifluorometh-yl)-1,5-dimethyl-N-(1,1,3-trimethylindan-4-yl)-pyrazole-4-carboxamide (A.3.24), 1,3,5-tri-methyl-N-(1,1,3-trimethylindan-4-yl)pyrazole-4-car-boxamide (A.3.25), N-(7-fluoro-1,1,3-trim-ethyl-indan-4-yl)-1,3-dimethyl-pyrazole-4-carbox-amide (A.3.26), N-[2-(2,4-dichlorophenyl)-2-methoxy-1-methyl-ethyl]-3-(difluoromethyl)-1-methyl-pyrazole-4-carboxamide (A.3.27);

other respiration inhibitors (e. g. complex I, uncouplers): diflumetorim (A.4.1), (5,8-difluoro-quinazolin-4-yl)-{2-[2-fluoro-4-(4-trifluoromethylpyridin-2-yloxy)-phenyl]-ethyl}-amine; tecnazen; ametoctradin; silthiofam; (A.4.2); nitrophenyl derivates: binapacryl, (A.4.3), dinobuton, (A.4.4), dinocap, (A.4.5), fluazinam, (A.4.6); ferimzone, nitrthal-isopropyl, (A.4.7); organometal com-pounds: fentin salts, such as fentin-acetate (A.4.8), fentin chloride (A.4.9) or fentin hydroxide (A.4.10); ametoctradin (A.4.11); and silth-iofam (A.4.12);

and including organometal compounds: fentin salts, such as fentin-acetate, fentin chloride or fentin hydroxide;

F.II) B) Sterol biosynthesis inhibitors (SBI fungicides)

F.II-1)—C14 demethylase inhibitors (DMI fungicides, e.g.): triazoles, imidazoles) triazoles: azaconazole, (B.1.1), bitertanol, (B.1.2), bromuconazole, (B.1.3), cyproconazole, (B.1.4), difenoconazole, (B.1.5), diniconazole, (B.1.6), diniconazole-M, (B.1.7), epoxiconazole, (B.1.8), fenbuconazole, (B.1.9), fluquinconazole, (B.1.10), flusilazole, (B.1.11), flutriafol, (B.1.12), hexaconazole, (B.1.13), imibenconazole, (B.1.14), ipconazole, (B.1.15), metconazole, (B.1.17), myclobutanil, (B.1.18), oxpoconazole (B.1.19), paclobutrazole, (B.1.20), penconazole, (B.1.21), propiconazole, prothioconazole, (B.1.22), prothio-conazole (B.1.23), simeconazole, (B.1.24), tebuconazole, (B.1.25), tetraconazole, (B.1.26), triadimefon, (B.1.27), triadimenol, (B.1.28), triticonazole, (B.1.29), uniconazole, (B.1.30), 1-[rel-(2S;3R)-3-(2-chloro-phenyl)-2-(2,4-difluorophenyl)-oxiranylmethyl]-5 thio-cyanato-1H-[1,2,4]triazole,triazolo (B.1.31), 2-[rel-(2S;3R)-3-(2-chlorophenyl)-2-(2,4-difluorophenyl)-oxiranyl-methyloxi-ranyl-methyl]-2H [1,2,4]triazole-3-thiol;

(B.1.32), 2-[2-chloro-4-(4-chlorophenoxy)-phenyl]-1 (1,2,4-triazol-1-yl)pentan-2-ol (B.1.33), 1-[4-(4-chlorophenoxy)-2-(trifluoro-methyl)phenyl]-1 cyclopropyl-2-(1,2,4-triazol-1-yl)ethanol (B.1.34), 2-[4-(4-chloro-phenoxy)-2-(trifluorometh-yl)phenyl]-1-(1,2,4-triazol-1-yl)butan-2-ol (B.1.35), 2 [2 chloro-4-(4-chlorophenoxy)phenyl]-1-(1,2,4-triazol-1-yl)butan-2-ol (B.1.36), 2 [4 (4 chloro-phenoxy)-2-(trifluoromethyl)phenyl]-3-methyl-1-(1,2,4-triazol-1 yl)butan-2-ol (B.1.37), 2-[4-(4-chlorophenoxy)-2-(trifluoromethyl)-phenyl]-1-(1,2,4-triazol-1-yl)propan-2-ol (B.1.38), 2-[2-chloro-4-(4-chlorophenoxy)phenyl]-3-methyl-1-(1,2,4-triazol-1-yl)butan-2-ol (B.1.39), 2-[4-(4-chlorophenoxy)-2-(trifluoromethyl)-phenyl]-1-(1,2,4-triazol-1-yl)pentan-2-ol (B.1.40), 2-[4-(4-fluorophenoxy)-2-(trifluoromethyl)phenyl]-1-(1,2,4-triazol-1-yl)propan-2-ol (B.1.41), 2-[2-chloro-4-(4-chlorophenoxy)phenyl]-1-(1,2,4-triazol-1-yl)pent-3-yn-2-ol (B.1.51); imidazoles: imazalil, (B.1.42), pefurazoate, oxpoconazole, (B.1.43), prochloraz, triflumizole;

(B.1.44), triflumizol (B.1.45); pyrimidines, pyridines and piperazines: fenarimol, (B.1.46), nuarimol, (B.1.47), pyrifenox, (B.1.48), triforine, 1-[rel-(2S;3R)-3-(2-chloro-phenyl)-2-(2,4-difluorophenyl)-oxiranylmethyl]-5 thiocyanato-1H-[1,2,4]triazole, 2-[rel-(2S;3R)-3-(2-chlorophenyl)-2-(2,4-difluorophenyl)-oxiranylmethyl]-2H [1,2,4]triazole-3-thiol; (B.1.49), [3-(4-chloro-2-fluoro-phenyl)-5-(2,4-difluoro-phenyl)isoxazol-4-yl]-(3-pyridyl)methanol (B.1.50);

F.II-2)—Delta14-reductase inhitors (Amines, e.g. morpholines, piperidines) morpholinesinhibitors: aldimorph, (B.2.1), dodemorph, (B.2.2), dodemorph-acetate, (B.2.3), fenpropimorph, (B.2.4), tridemorph;

piperidines: (B.2.5), fenpropidin, (B.2.6), piperalin; spiroketalamines: (B.2.7), spiroxamine; (B.2.8);

F.II-3)—Inhibitors of 3-keto reductase: hydroxyanilides: fenhexamid; (B.3.1);

F.III) C) Nucleic acid synthesis inhibitors

F.III-1) RNA, DNA synthesis
phenylamides or acyl amino acid fungicides: benalaxyl, (C.1.1), benalaxyl-M, (C.1.2), kiralaxyl, (C.1.3), metalaxyl, (C.1.4), metalaxyl-M (mefenoxam, C.1.5), ofurace, (C.1.6), oxadix-yl; (C.1.7);
isoxazoles and iosothiazolones—others: hymexazole, (C.2.1), octhilinone;

F.III-2) DNA topisomerase inhibitors: (C.2.2), oxolinic acid;

F.III-3) Nucleotide metabolism (e.g. adenosin-deaminase), hydroxy (2-amino)-pyrimidines: (C.2.3), bupirimate; (C.2.4), 5-fluorocytosine (C.2.5), 5-fluoro-2-(p-tolyl-methoxy)pyrimidin-4-amine (C.2.6), 5-fluoro-2-(4-fluoro-phenylmethoxy)pyrimidin-4 amine (C.2.7);

F.IV) D) Inhibitors of cell division and or cytoskeleton

F.IV-1) Tubulin—tubulin inhibitors, such as benzimidazoles and, thiophanates: benomyl, (D1.1), carbendazim, (D1.2), fuberidazole, (D1.3), thiabendazole, (D1.4), thiophanate-methyl;
(D1.5); triazolopyrimidines: 5-chloro-7 ((4-methylpiperidin methyl¬piperidin-1-yl)-6-(2,4,6-trifluorophenyltrifluoro¬phenyl)-[1,2,4]triazolotri¬azolo [1,5 a]pyrimidine; (D1.6);

F.IV-2) Other—other cell division inhibitors
benzamides and phenyl acetamides: diethofencarb, (D2.1), ethaboxam, (D2.2), pencycuron, (D2.3), fluopicolide, (D2.4), zoxamide;

F.IV-3) Actin inhibitors: benzophenones: (D2.5), metrafenone, (D2.6), pyriofenone; (D2.7);

F.V) E) Inhibitors of amino acid and protein synthesis

F.V-1) Methionine—methionine synthesis inhibitors (anilino-pyrimidines) anilino-pyrimidines:): cyprodinil, mepanipyrim, nitrapyrin, (E.1.1), mepanihpyrim (E.1.2), pyrimethanil; (E.1.3);

F.V-2) Protein—protein synthesis inhibitors (anilino-pyrimidines)
antibiotics: blasticidin-S, (E.2.1), kasugamycin, (E.2.2), kasugamycin hydrochloride-hydrate, (E.2.3), mildiomycin, (E.2.4), streptomycin, oxytetracyclin, (E.2.5), oxytetra¬cyclin (E.2.6), polyoxine, (E.2.7), validamycin A; (E.2.8);

F.VI)) Signal transduction inhibitors

F.VI-1)—MAP/Histidinehistidine kinase inhibitors (e.g. anilino-pyrimidines) dicarboximides: fluoroimid, (F.1.1), iprodione, (F.1.2), procymidone, (F.1.3), vinclozolin; phenylpyrroles: (F.1.4), fenpiclonil, (F.1.5), fludioxonil; (F.1.6);

F.VI-2)—G protein inhibitors: quinolines: quinoxyfen; (F.2.1);

F.VII) G) Lipid and membrane synthesis inhibitors

F.VII-1)—Phospholipid biosynthesis inhibitors
organophosphorus compounds: edifenphos, (G.1.1), iprobenfos, pyrazophos; dithiolanes: (G.1.2), pyrazo-phos (G.1.3), isoprothiolane; (G.1.4);

F.VII-2) Lipid—lipid peroxidation: aromatic hydrocarbons: dicloran, (G.2.1), quintozene, (G.2.2), tecnazene, (G.2.3), tolclofos-methyl, (G.2.4), biphenyl, (G.2.5), chloroneb, (G.2.6), etridiazole; (G.2.7);

F.VII-3) Carboxyl acid amides (CAA fungicides)
cinnamic or mandelic acid amides-phospholipid biosynthesis and cell wall deposition: dimethomorph, (G.3.1), flumorph, mandiproamid, (G.3.2), mandipropamid (G.3.3), pyrimorph;
valinamide carbamates: (G.3.4), benthiavalicarb, iprovalicarb, pyribencarb, (G.3.5), iprovali¬carb (G.3.6), valifenal-ate (G.3.7) and N-(1-(1-(4-cyano-phenyl) ethanesulfonyl¬ethanesulfonyl)-but-2-yl) carbamic acid-(4-fluorophenyl) ester; (G.3.8);

F.VII-4) Compounds—compounds affecting cell membrane permeability and fatty acids: 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, carbamatesacides: propamocarb, propamocarb-hydrochlorid, (G.4.1);

F.VII-5)—fatty acid amide hydrolase inhibitors: oxathiapiprolin (G.5.1-[4-[4-[5-( ), 2,6-difluorophenyl)-4,5-dihydro-{3 isoxazolyl]-[2-thiazolyl]--(1-piperidinyl]-2-[5-methyl-{[3-(trifluoromethyl)-,5-bis(di¬fluoromethyl-1H-pyrazol-1-yl]ethanone;acetyl}piperidin-4-yl)-1,3-thiazol-4-yl]-4,5-dihydro-1,2 oxazol-5-yl}phenyl methanesulfonate (G.5.2), 2-{3-[2-(1-{[3,5-bis(difluoro¬me¬thyl)-1H-pyrazol-1-yl]acetyl}piperidin-4-yl) 1,3-thiazol-4-yl]-4,5-dihydro-1,2-oxazol-5 yl}-3-chlorophenyl methanesulfonate (G.5.3);

F.VIII) H) Inhibitors with Multi Site Action

F.VIII-1) Inorganic—inorganic active substances: Bordeaux mixture, (H.1.1), copper acetate, (H.1.2), copper hydroxide, (H.1.3), copper oxychloride, (H.1.4), basic copper sulfate, (H.1.5), sulfur; (H.1.6);

F.VIII-2) Thio—thio- and dithiocarbamates: ferbam, (H.2.1), mancozeb, (H.2.2), maneb, (H.2.3), metam, methasulphocarb, (H.2.4), metiram, (H.2.5), propineb, (H.2.6), thiram, (H.2.7), zineb, (H.2.8), ziram; (H.2.9);

F.VIII-3) Organochlorine—organochlorine compounds (e. g. phthalimides, sulfamides, chloronitriles):
anilazine, (H.3.1), chlorothalonil, (H.3.2), captafol, (H.3.3), captan, (H.3.4), folpet, (H.3.5), dichlofluanid, (H.3.6), dichlorophen, flusulfamide, hexachlorbenzene, (H.3.7), hexachloro-benzene (H.3.8), pentachlorphenole (H.3.9) and its salts, phthalide, (H.3.10), tolylfluanid, (H.3.11), N-((4-chloro-2-nitro-phenyl)-N-ethyl-4-methyl-benzenesulfonamide; (H.3.12);

F.VIII-4) Guanidines—guanidines and otherothers: guanidine, (H.4.1), dodine, (H.4.2), dodine free base, (H.4.3), guazatine, (H.4.4), guazatine-acetate, (H.4.5), iminoctadine, (H.4.6), iminoctadine-triacetate, (H.4.7), iminoctadine-tris (albesilate) (H.4.8), dithianon (H.4.9), 2,6-dimethyldi¬methyl-1H,5H-[1,4]dithiino[2,3-c:5,6-c']dipyrrole-1,3,5,7(2H,6H)-tetraone; (H.4.10);

F.VIII-5) Ahtraquinones: dithianon;

F.IX) I) Cell wall synthesis inhibitors

F.IX-1) Inhibitors-inhibitors of glucan synthesis: validamycin, (I.1.1), polyoxin B; (I.1.2);

F.IX-2) Melanin—melanin synthesis inhibitors: pyroquilon, (I.2.1), tricyclazole, carpropamide, (I.2.2), carpropamid (I.2.3), dicyclomet, (I.2.4), fenoxanil; (I.2.5);

F.X) J) Plant defence inducers

F.X-1) Salicylic acid pathway:—acibenzolar-S-methyl;

F.X-2) Others: (J.1.1), probenazole, (J.1.2), isotianil, (J.1.3), tiadinil, (J.1.4), prohexadione-calcium;
(J.1.5); phosphonates: fosetyl, (J.1.6), fosetyl-aluminum, (J.1.7), phosphorous acid and its salts; (J.1.8), potassium or sodium bicarbonate (J.1.9);

F.XI) K) Unknown mode of action:
bronopol, (K.1.1), chinomethionat, (K.1.2), cyflufenamid, (K.1.3), cymoxanil, (K.1.4), daz-omet, (K.1.5), debacarb, diclomezine, (K.1.6), diclo¬mezine (K.1.7), difenzoquat, (K.1.8), difen-zoquat-methylsulfate, (K.1.9), diphenylamin, (K.1.10), fenpyrazamine, (K.1.11), flumetover, (K.1.12), flusulfamide, (K.1.13), flutianil, (K.1.14), methasulfocarb, (K.1.15), nitrapyrin, (K.1.16), nitrothal-isopropyl, (K.1.18), oxathiapiprolin, (K.1.19), tolprocarb (K.1.20), oxin-copper, (K.1.21), proquinazid, (K.1.22), tebufloquin, (K.1.23), tecloftalam, (K.1.24), triazoxide, (K.1.25), 2-butoxy-6-iodo-3-propylchromen-4-one, (K.1.26), 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]etha-none (K.1.27), 2-[3,5-bis(difluoromethyl)-1H-pyrazol-1-yl]-1-[4-(4-{5-[2-fluoro-6-(prop-2-yn-1-yl-oxy)phenyl]-4,5-dihydro-1,2-oxazol-3-yl}-1,3-thihazol-2-yl)piperidin-1-yl] ethanone (K.1.28), 2 [3,5-bis(difluoromethyl)-1H-pyrazol-1-yl]-1-[4-(4-{5-[2-chloro-6-(prop-2-yn-1-ylhoxy)phenyl]-4,5-dihydro-1,2-oxazol-3-yl}-1,3-thiazol-2 yl)piperidin-1-yl]ethanone (K.1.29), N-(cyclopropylmethoxyiminocyclo¬propylmethoxyi mino-(6-difluoro-methoxy-2,3-difluoro di¬fluoro-phenyl)-methyl)-2-phenyl acetamide, (K.1.30), N'-(4-(4-chloro-3-trifluoromethyl-phenoxytrifluoro-methyl-phenroxy)-2,5-dimethyl-phenyl)-N-ethyl-N methyl formamidine, (K.1.31), N' ((4-(4-fluoro-3-trifluoromethyltrifluoro¬methyl-phenoxy)-2,5-dimethyl-phenyl)-N-ethyl-N-methyl formamidine, (K.1.32), N'-(2-methyl-5-trifluoromethyl-4-(3-trimethylsilanyl-propoxytrimethyl-silanyl-prop¬oxy)-phenyl)-N-ethyl-N-methyl formamidine,forma¬midine (K.1.33), N'-(5-difluoromethyl-2 methyl-4-(3-trimethylsilanyltri¬methylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, (K.1.34), methoxyacetic acid 6-tert-butyl-8-fluoro-2,3-dimethyl-quinolin-4-yl ester and N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide, 3-[(K.1.35), 3-[5-(4-methylphenyl)-2,3-dimethyl-isoxazolidin-3 yl]-pyridine (K.1.36), 3 [5-(4-chloro-phenyl)-2,3-dimethyl-isoxazolidin-3-yl]-pyridine, (pyrisoxazole, 5-amino-2-isopropyl-3-oxo-4-ortho-tolyl-2,3-dihydro-pyrazole-1 carbothioic acid S-allyl ester, N-(6-methoxy) (K.1.37), N-(6-meth¬oxy-pyridin-3-yl) cyclopropanecarboxyliccyclopropane¬carboxylic acid amide, (K.1.38), 5-chloro-1 ((4,6-dimethoxydi¬methoxy-pyrimidin-2-yl)-2-methyl-1H-benzoimidazole,ben-zoimidazole (K.1.39), 2-(4-chloro-phenyl)-N-[4-(3,4-dimethoxydimeth¬oxy-phenyl)-isoxazol-5-yl]-2-prop-2-ynyloxy-acetamide, ethyl (Z) 3 amino-2-cyano-3-phenyl-prop-2-enoate (K.1.40), picarbutrazox (K.1.41), pentyl N-[6-[[(Z)-[(1-methyltetrazol-5-yl)-phenyl-methylene]amino] oxy-methyl]-2-pyridyl]carbamate (K.1.42), 2-[2-[(7,8-difluoro-2-methyl-3-quinolyl)oxy]-6-fluoro-phenyl] propan-2-ol (K.1.43), 2-[2-fluoro-6-[(8-fluoro-2-methyl-3-quinolyl)oxy]¬phen-yl]propan-2-ol (K.1.44), 3-(5-fluoro-3,3,4,4-tetramethyl-3,4-dihydroiso¬quinolin-1-yl)¬quinoline (K.1.45), 3-(4,4-difluoro-3,3-dimethyl-3,4-dihydroisoquinolin-1-yl) ¬quin¬oline (K.1.46), 3-(4,4,5-trifluoro-3,3-dimethyl-3,4-dihydroisoquinolin-1-yl)quinoline (K.1.47), 9-fluoro-2,2-dimethyl-5-(3-quinolyl)-3H 1,4-benzoxazepine (K.1.48).

F.XII) Growth regulators: abscisic acid, amidochlor, ancymidol, 6-benzylaminopurine, brassino-lide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N 6-benzyladenine, paclobutrazol, pro-hexadione (prohexadione-calcium), pro-hydrojasmon, thidiazuron, triapenthenol, tributyl phosphorotrithioate, 2,3,5 tri iodobenzoic acid, trinexapac-ethyl and uniconazole. The commercially available compounds of the group F listed above may be found in The Pes-ticide Manual, 15th Edition, C. D. S. Tomlin, British Crop Protection Council (2011) among other publications. Their fungicides described by common names, their preparation and their activity e.g. against harmful fungi is known (cf.: http://www.alanwood.net/pesticides/); these substances are commercially available. The compounds fungicides described by IUPAC nomenclature, their preparation and their fun-gicidal pesticidal activity are is also known (cf. Can. J. Plant Sci. 48(6), 587-94, 1968; EP A 141 317; EP-A 152 031; EP-A 226 917; EP A 243 970; EP A 256 503; EP-A 428 941; EP-A 532 022; EP-A 1 028 125; EP-A 1 035 122; EP A 1 201 648; EP A 1 122 244, JP 2002316902; DE 19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657, WO2012/168188, WO 2007/006670, WO 2011/77514; WO13/047749, WO 10/069882, WO 13/047441, WO 03/16303, WO 09/90181, WO 13/007767, WO 13/010862, WO 13/127704, WO 13/024009, WO 13/024010 and WO 13/047441, WO 13/162072, WO 13/092224, WO 11/135833).

The compounds of the invention may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same The invertebrate pest (also referred to as "animal pest"), i.e. the insects, arachnids and nematodes, the plant, soil or water in which the plant is growing or may grow can be contacted with the compounds of the present invention or composition(s) comprising them by any application method known in the art. As such, "contacting" includes both direct contact (applying the compounds/compositions directly on the invertebrate pest or plant—typically to the foliage, stem or roots of the plant) and indirect contact (applying the compounds/compositions to the locus of the invertebrate pest or plant).

The compounds of the present invention or the pesticidal compositions comprising them may be used to protect growing plants and crops from attack or infestation by animal pests, especially insects, acaridae or arachnids by contacting the plant/crop with a pesticidally effective amount of compounds of the present invention. The term "crop" refers both to growing and harvested crops.

The compounds of the present invention and the compositions comprising them are particularly important in the control of a multitude of insects on various cultivated plants, such as cereal, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and *impatiens*.

The compounds of the present invention are employed as such or in form of compositions by treating the insects or the plants, plant propagation materials, such as seeds, soil, surfaces, materials or rooms to be protected from insecticidal attack with an insecticidally effective amount of the active compounds. The application can be carried out both before and after the infection of the plants, plant propagation materials, such as seeds, soil, surfaces, materials or rooms by the insects.

Moreover, invertebrate pests may be controlled by contacting the target pest, its food supply, habitat, breeding ground or its locus with a pesticidally effective amount of compounds of the present invention. As such, the application may be carried out before or after the infection of the locus, growing crops, or harvested crops by the pest.

The compounds of the present invention can also be applied preventively to places at which occurrence of the pests is expected.

The compounds of the present invention may be also used to protect growing plants from attack or infestation by pests by contacting the plant with a pesticidally effective amount of compounds of the present invention. As such, "contacting" includes both direct contact (applying the compounds/compositions directly on the pest and/or plant—typically to the foliage, stem or roots of the plant) and indirect contact (applying the compounds/compositions to the locus of the pest and/or plant). "Locus" means a habitat, breeding ground, plant, seed, soil, area, material or environment in which a pest or parasite is growing or may grow.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in treating crop plants, the rate of application of the active ingredients of this invention may be in the range of 0.1 g to 4000 g per hectare, desirably from 5 g to 500 g per hectare, more desirably from 5 g to 200 g per hectare.

The compounds of the present invention are effective through both contact (via soil, glass, wall, bed net, carpet, plant parts or animal parts), and ingestion (bait, or plant part).

The compounds of the present invention may also be applied against non-crop insect pests, such as ants, termites, wasps, flies, mosquitos, crickets, or cockroaches. For use against said non-crop pests, compounds of the present invention are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics. The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art. For use in bait compositions, the typical content of active ingredient is from 0.001 weight % to 15 weight %, desirably from 0.001 weight % to 5% weight % of active ingredient.

Formulations of compounds of the present invention as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of the present invention and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of the present invention and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethylcyclohexyl) acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets.

The compounds of the present invention and their compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of the present invention are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The compounds of the present invention are also suitable for the treatment of plant propagation material, especially seeds, in order to protect them from insect pest, in particular from soil-living insect pests and the resulting plant's roots and shoots against soil pests and foliar insects.

The compounds of the present invention are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with a compound of the present invention, including a salt thereof. Particularly preferred is a method, wherein the plant's roots and shoots are protected, more preferably a method, wherein the plants shoots are protected form piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and *impatiens. In addition, the active compound may also be used for the treatment seeds from plants, which tolerate the action of herbicides or fungicides or insecticides owing to breeding, including genetic engineering methods.*

For example, the active compound can be employed in treatment of seeds from plants, which are resistant to herbicides from the group consisting of the sulfonylureas, imidazolinones, glufosinate-ammonium or glyphosate-isopropylammonium and analogous active substances (see for example, EP-A 242 236, EP-A 242 246) (WO 92/00377) (EP-A 257 993, U.S. Pat. No. 5,013,659) or in transgenic crop plants, for example cotton, with the capability of producing *Bacillus thuringiensis* toxins (Bt toxins) which make the plants resistant to certain pests (EP-A 142 924, EP-A 193 259), Furthermore, the active compound can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is carried out by spraying or by dusting the seeds before sowing of the plants and before emergence of the plants. Compositions which are especially useful for seed treatment are e.g.:

A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter.

In a preferred embodiment a FS formulation is used for seed treatment. Typcially, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of compounds of the present invention for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed Treatment formulations may additionally also comprise binders and optionally colorants.

Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethyleneimines, polysaccharides like celluloses, tylose and starch, polyolefin homo- and copolymers like olefin/maleic anhydride copolymers, polyurethanes, polyesters, polystyrene homo and copolymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a gelling agent is carrageen (Satiagel®)

In the treatment of seed, the application rates of the compounds of the present invention are generally from 0.01 g to 10 kg per 100 kg of seed, preferably from 0.05 g to 5 kg per 100 kg of seed, more preferably from 0.1 g to 1000 g per 100 kg of seed and in particular from 0.1 g to 200 g per 100 kg of seed.

The invention therefore also relates to seed comprising a compound of the present invention, including an agriculturally useful salt of it, as defined herein. The amount of the compound of the present invention, including an agriculturally useful salt thereof will in general vary from 0.01 g to 10 kg per 100 kg of seed, preferably from 0.05 g to 5 kg per 100 kg of seed, in particular from 0.1 g to 1000 g per 100 kg of seed. For specific crops such as lettuce the rate can be higher.

Methods which can be employed for treating the seed are, in principle, all suitable seed treatment and especially seed dressing techniques known in the art, such as seed coating (e.g. seed pelleting), seed dusting and seed imbibition (e.g. seed soaking). Here, "seed treatment" refers to all methods that bring seeds and the compounds of the present invention into contact with each other, and "seed dressing" to methods of seed treatment which provide the seeds with an amount of the compounds of the present invention, i.e. which generate a seed comprising a compound of the present invention. In principle, the treatment can be applied to the seed at any time from the harvest of the seed to the sowing of the seed. The seed can be treated immediately before, or during, the planting of the seed, for example using the "planter's box" method. However, the treatment may also be carried out several weeks or months, for example up to 12 months, before planting the seed, for example in the form of a seed dressing treatment, without a substantially reduced efficacy being observed.

Expediently, the treatment is applied to unsown seed. As used herein, the term "unsown seed" is meant to include seed at any period from the harvest of the seed to the sowing of the seed in the ground for the purpose of germination and growth of the plant.

Specifically, a procedure is followed in the treatment in which the seed is mixed, in a suitable device, for example a mixing device for solid or solid/liquid mixing partners, with the desired amount of seed treatment formulations, either as such or after previous dilution with water, until the composition is distributed uniformly on the seed. If appropriate, this is followed by a drying step.

The compounds of the present invention, including their stereoisomers, veterinarily acceptable salts or N-oxides, are in particular also suitable for being used for combating parasites in and on animals.

An object of the present invention is therefore also to provide new methods to control parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions comprising a parasiticidally effective amount of compounds of the present invention, including their stereoisomers, veterinarily acceptable salts or N-oxides, and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of the present invention, including its stereoisomers, veterinarily acceptable salts or N-oxides, or a composition comprising it.

The invention also provides the use of a compound of the present invention, including its stereoisomers, veterinarily acceptable salts or N-oxides, for treating or protecting an animal from infestation or infection by invertebrate pests.

The invention also provides a process for the preparation of a composition for treating, controlling, preventing or protecting animals against infestation or infection by parasites which comprises a parasiticidally effective amount of a compound of the present invention, including its stereoisomers, veterinarily acceptable salts or N-oxides, or a composition comprising it.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that compounds of formula (I) and their stereoisomers, veterinarily acceptable salts, tautomers and N-oxides, are suitable for combating endo- and ectoparasites in and on animals.

The compounds of the present invention, especially compounds of formula (I) and their stereoisomers, veterinarily acceptable salts, tautomers and N-oxides, and compositions comprising them are preferably used for controlling and preventing infestations of and infections in animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of the present invention, including their stereoisomers, veterinarily acceptable salts or N-oxides, and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of the present invention, including their stereoisomers, veterinarily acceptable salts or N-oxides, and compositions comprising them are suitable for systemic and/or non-systemic control of ecto- and/or endoparasites. They are active against all or some stages of development.

The compounds of the present invention are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans*, and *Nosopsyllus fasciatus*, cockroaches (*Blattaria*-Blattodea), e.g. *Blattella germanica, Blattella asahinae, Periplaneta americana, Periplaneta japonica, Periplaneta brunnea, Periplaneta fuligginosa, Periplaneta australasiae*, and *Blatta orientalis*, flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola*, and *Tabanus similis*, lice (Phthiraptera), e.g. *Pediculus humanus* capitis, *Pediculus humanus* corporis, *Pthirus pubis, Haematopinus eurysternus, Haematopinus suis, Linognathus vituli, Bovicola bovis, Menopon gallinae, Menacanthus stramineus* and *Solenopotes capillatus*.

ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae*, Actinedida (Prostigmata) und Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp., Bugs (Heteropterida): *Cimex lectularius, Cimex hemipterus, Reduvius senilis, Triatoma* spp., *Rhodnius* ssp., *Panstrongylus* ssp. and *Arilus critatus*, Anoplurida, e.g. *Haematopinus* spp., *Linognathus* spp., *Pediculus* spp., *Phtirus* spp., and *Solenopotes* spp., Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp., Roundworms Nematoda:

Wipeworms and Trichinosis (Trichosyringida), e.g. Trichinellidae (*Trichinella* spp.), (Trichuridae) *Trichuris* spp., *Capillaria* spp., Rhabditida, e.g. *Rhabditis* spp., *Strongyloides* spp., *Helicephalobus* spp., Strongylida, e.g. *Strongylus* spp., *Ancylostoma* spp., *Necator americanus, Bunostomum* spp. (Hookworm),

*Trichostrongylus* spp., *Haemonchus contortus.*, *Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., Stephanurus *dentatus, Syngamus trachea, Ancylostoma* spp., *Uncinaria* spp., *Globocephalus* spp., *Necator* spp., *Metastrongylus* spp., Muellerius *capillaris, Protostrongylus* spp., *Angiostrongylus* spp., *Parelaphostrongylus* spp. *Aleurostrongylus abstrusus*, and *Dioctophyma renale*, Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi*, Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi*, and *Habronema* spp., Thorny headed worms (Acanthocephala), e.g. *Acanthocephalus* spp., *Macracanthorhynchus hirudinaceus* and *Oncicola* spp., Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp., Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The present invention relates to the therapeutic and the non-therapeutic use of compounds of the present invention and compositions comprising them for controlling and/or combating parasites in and/or on animals. The compounds of the present invention and compositions comprising them may be used to protect the animals from attack or infestation by parasites by contacting them with a parasiticidally effective amount of compounds of the present invention and compositions containing them. The compounds of the present invention and compositions comprising them can be effective through both contact (via soil, glass, wall, bed net, carpet, blankets or animal parts) and ingestion (e.g. baits). As such, "contacting" includes both direct contact (applying the pesticidal mixtures/compositions containing the compounds of the present invention directly on the parasite, which may include an indirect contact at its locus-P, and optionally also administrating the pesticidal mixtures/composition directly on the animal to be protected) and indirect contact (applying the compounds/compositions to the locus of the parasite). The contact of the parasite through application to its locus is an example of a non-therapeutic use of compounds of the present invention. "Locus-P" as used above means the habitat, food supply, breeding ground, area, material or environment in which a parasite is growing or may grow outside of the animal.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions of the present invention. A parasiticidally effective amount of the compositions will also vary according to the prevailing conditions such as desired parasiticidal effect and duration, target species, mode of application, and the like.

The compounds of the present invention can also be applied preventively to places at which occurrence of the pests or parasites are expected.

Administration can be carried out both prophylactically and therapeutically.

Administration of the active compounds is carried out directly or in the form of suitable preparations, orally, topically/dermally or parenterally.

The compounds of the invention are better bio-degradable than those of the prior art and in addition retain a high level of pest control. This makes them superior in terms of environmental safety. In light of the structural similarities of the compounds of formula I, this significant difference in bio-degradability in favour of the compounds of the invention is unexpected and cannot be derived from what is known from the prior art.

EXAMPLES

The present invention is now illustrated in further details by the following examples, without imposing any limitation thereto.

ABBREVIATIONS

TLC thin layer chromatography
r.t. room temperature (20-25° C.)
PE petrol ether
TFA trifluoroacetic acid
EtOAc ethyl acetate
THF tetrahydrofuran
t-BuOH tert-butanol
DMAP 4-(dimethylamino)-pyridine
LDA lithiumdiisopropylamide
TsCl tosylchloride
MTBE methyl-tert-butyl ether
DMF N,N-dimethylformamide
DCM dichloromethane
PyBrOP bromo-tris-pyrrolidino phosphoniumhexafluorophosphate
NBS N-bromosuccinimide
MeOH methanol
TEA trimethylamine
dppf 1,1'-bis(diphenylphosphino)ferrocen
MeCN acetonitrile
EtOH ethanol
m-CPBA meta-chloroperbenzoic acid
$PPh_3$ triphenylphosphine I. Preparation Examples Compounds can be characterized e.g. by coupled High Performance Liquid Chromatography/mass spectrometry (HPLC/MS), by $^1$H-NMR and/or by their melting points.

Analytical HPLC column:

HPLC method 1: Phenomenex Kinetex 1.7 μm XB-C18 100A; 50×2.1 mm; mobile phase: A: water+0.1% trifluoroacetic acid (TFA); B: acetonitrile+0.1% TFA; gradient: 5-100% B in 1.50 minutes; 100% B 0.20 min; flow: 0.8-1.0 ml/min in 1.51 minutes at 60° C.

HPLC method 2: Phenomenex Kinetex 1.7 μm XB-C18 100A; 50×2.1 mm; mobile phase: A: water+0.1% trifluoroacetic acid (TFA); B: acetonitrile+0.1% TFA; gradient:

5-100% B in 1.25 minutes; 100% B 0.70 min; flow: 0.8-1.0 ml/min in 1.51 minutes at 60° C. MS method: ESI positive, Mass range (m/z): 100-700.

$^1$H-NMR: The signals are characterized by chemical shift (ppm) vs. tetramethylsilane, by their multiplicity and by their integral (relative number of hydrogen atoms given). The following abbreviations are used to characterize the multiplicity of the signals: m=multiplett, q=quartett, t=triplett, d=doublet and s=singlett.

Preparation Examples

Example 1: Synthesis of 4-[5-(3,5-dichloro-4-fluoro-phenyl)-5-(trifluoromethyl)-4H-isoxazol-3-yl]-N-(1,1-dioxothietan-3-yl)-2,3-dihydrobenzothiophene-7-carboxamide (Compound I-7)

Step 1: Preparation of tert-butyl 4-bromo-2-fluoro-benzoate

To a solution of 4-bromo-2-fluoro-benzoic acid (100.0 g, 0.46 mol) in THF/t-BuOH (800 mL/400 mL) was added Boc$_2$O (150.0 g, 0.69 mol) and DMAP (5.6 g, 46.0 mmol), the mixture was stirred at 80° C. for 13 h. TLC (PE: EtOAc=10:1) showed the reaction was completed. After removal of the solvent, the residue was dissolved in water and extracted with EtOAc (500 mL×3), the organic layer was dried over Na$_2$SO$_4$ and concentrated to give the crude product, which was purified by column chromatography (PE:EtOAc=100:1) to give the title compound (120.0 g, 95.5%) as a colorless oil.

$^1$H-NMR (400 MHz, CDCl$_3$): δ=7.69-7.78 (m, 1H) 7.26-7.34 (m, 2H) 1.58 (s, 9H)

Step 2: tert-Butyl 4-bromo-2-fluoro-3-(2-hydroxyethyl)benzoate

To a solution of tert-butyl 4-bromo-2-fluoro-benzoate (60.0 g, 0.22 mol) in THF was added LDA (130 mL, 0.26 mol) drop wise at −78° C., the mixture was stirred at this temperature for 4 h, then oxirane (77.0 g, 1.75 mol) was added. The mixture was stirred at this temperature for another 6 h, then the reaction mixture was poured into aq. NH$_4$Cl (300 mL) and extracted with EtOAc (400 mL×3). The organic layer was dried over Na$_2$SO$_4$ and concentrated to give the crude product, which was purified by silica gel chromatograph (PE:EtOAc=10:1~5:1) to give the title compound (14.0 g, 20.0%) as a yellow solid.

$^1$H-NMR (400 MHz, CDCl$_3$): δ=7.61 (t, J=8.03 Hz, 1H) 7.40 (d, J=8.28 Hz, 1H) 3.87 (t, J=6.90 Hz, 2H) 3.16 (t, J=6.90, 2.51 Hz, 2H) 1.60 (s, 9H)

Step 3: tert-Butyl 4-bromo-2-fluoro-3-[2-(p-tolylsulfonyloxy)ethyl]benzoate

To a solution of tert-butyl 4-bromo-2-fluoro-3-(2-hydroxyethyl)benzoate (10.0 g, 31.4 mmol) in pyridine was added TsCl (9.0 g, 47.2 mmol) in portions at 0° C. The mixture was stirred at 15° C. for 14h. TLC (PE:EtOAc=10:1) showed the reaction was complete. After removal of the solvent, the residue was dissolved in water, extracted with MTBE (200 mL×3), the organic layer was dried over Na$_2$SO$_4$ and concentrated to give the crude product (17 g), which was used directly in the next step without further purification.

$^1$H-NMR (400 MHz, CDCl$_3$): δ=7.61 (t, J=8.16 Hz, 1H) 7.40 (d, J=8.82 Hz, 1H) 3.87 (t, =6.84 Hz, 2H) 3.15 (td, = 6.84, 2.65 Hz, 2H) 1.59 (s, 9H)

Step 4: tert-Butyl 4-bromo-2,3-dihydrobenzothiophene-7-carboxylate

To a solution of tert-butyl 4-bromo-2-fluoro-3-[2-(p-tolylsulfonyloxy)ethyl]benzoate (17.0 g crude, 54.1 mmol) in DMF (200 mL) was added Na$_2$S (5.0 g, 65.0 mmol), the mixture was stirred at 60° C. for 14 h. TLC (PE:EtOAc=10:1) showed the reaction was complete. After removal of the solvent, the residue was dissolved in EtOAc and washed with water (100 mL×2), the organic layer was dried over Na$_2$SO$_4$ and concentrated to give the crude product, which was purified by column chromatography (PE:EtOAc=10:1) to give the title compound (6.9 g, 70.0% for 2 steps) as a colorless oil.

$^1$H-NMR (400 MHz, CDCl$_3$): δ=7.62 (d, J=8.38 Hz, 1H) 7.19 (d, J=8.38 Hz, 1H) 3.38 (d, J=7.06 Hz, 2H) 3.31 (d, J=7.06 Hz, 2H) 1.60 (s, 9H)

Step 5: tert-butyl 4-acetyl-2,3-dihydrobenzothiophene-7-carboxylate

To a solution of tert-butyl 4-bromo-2,3-dihydrobenzothiophene-7-carboxylate (6.9 g, 22.0 mmol) in DMF/H$_2$O (200 mL/60 mL) was added K$_2$CO$_3$ (6.2 g, 44.9 mmol) and Pd(PPh$_3$)$_2$Cl$_2$ (0.34 g, 0.44 mmol), then tributyl(1-ethoxyvinyl)stannane (9.5 g, 26.4 mmol) was added, the mixture was stirred at 110° C. under N$_2$ for 3 h. TLC (PE:EtOAc=5:1) showed the reaction was completed. To the resulting mixture was added KF (50 g) and stirred for an additional 1 h. After removal of the solvent, the residue was dissolved in water and extracted with EtOAc (100 mL×3), the organic layer was dried over Na$_2$SO$_4$ and concentrated, then the residue was dissolved in aq. HCl/THF (0.6 M) and stirred for 12 h. After that, it was extracted with EtOAc (100 mL×3), the organic layer was dried over Na$_2$SO$_4$ and concentrated to give the crude product, which was purified by column chromatography (PE:EtOAc=20:1) to give the title compound (2.8 g, 45.8%) as a yellow solid.

$^1$H-NMR (400 MHz, CDCl$_3$): δ=7.86 (d, J=7.94 Hz, 1H) 7.48 (d, J=7.94 Hz, 1H) 3.62 (t, J=8.16 Hz, 2H), 3.21-3.31 (m, 2H) 2.60 (s, 3H) 1.62 (s, 9H)

Step 6: tert-Butyl 4-[(E/Z)-3-(3,5-dichloro-4-fluorophenyl)-4,4,4-trifluoro-but-2-enoyl]-2,3-dihydrobenzothiophene-7-carboxylate

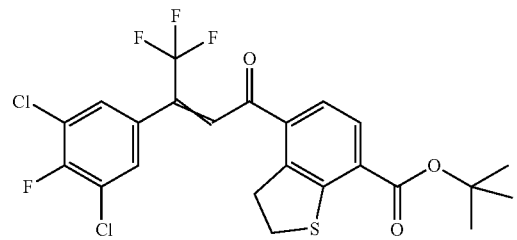 [SMILES: CC(C)(C)OC(=O)c1ccc(C(=O)C=C(c2cc(Cl)c(F)c(Cl)c2)C(F)(F)F)c2c1SCC2]

To a solution of tert-butyl 4-acetyl-2,3-dihydrobenzothiophene-7-carboxylate (2.8 g, 10.1 mmol) and 1-(3,5-dichloro-4-fluoro-phenyl)-2,2,2-trifluoro-ethanone 3 (5.2 g, 20.1 mol) in 1,2-dichloroethane (80 mL) was added K$_2$CO$_3$ (2.1 g, 15.1 mmol), then triethylamine (1.5 g, 15.1 mmol)

was added. The mixture was stirred for at 120° C. under N₂ for 14 h. TLC (PE:EtOAc=10:1) showed the reaction was complete. After removal of the solvent, the residue was purified by silica gel chromatography (PE:EtOAc=80:1) to give the title compound (6.0 g, crude as a mixture of E/Z isomers) as a yellow solid.

$^1$H-NMR (400 MHz, CDCl₃): δ=7.30-7.36 (m, 2H) 7.21 (d, J=6.02 Hz, 2H) 3.45-3.53 (m, 2H) 3.22-3.32 (m, 2H), 1.64 (s, 9H)

Step 7: tert-Butyl 4-[5-(3,5-dichloro-4-fluoro-phenyl)-5-(trifluoromethyl)-4H-isoxazol-3-yl]-2,3-dihydrobenzothiophene-7-carboxylate

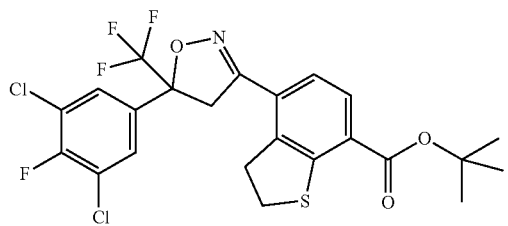 [SMILES: CC(C)(C)OC(=O)c1ccc(C2=NOC(c3cc(Cl)c(F)c(Cl)c3)(C(F)(F)F)C2)c2c1SCC2]

To a solution of tert-butyl 4-[(E/Z)-3-(3,5-dichloro-4-fluoro-phenyl)-4,4,4-trifluoro-but-2-enoyl]-2,3-dihydrobenzothiophene-7-carboxylate (6.0 g crude, 11.5 mol) in 1,2-dichloroethane (120 mL) was added NH₂OH·HCl (1.6 g, 23.0 mmol) and tetrabutylammoniumbromide (0.6 g, 1.9 mmol), then a solution of NaOH (1.8 g, 45.0 mmol) in water (30 mL) was added drop wise. The mixture was stirred for 3 h, TLC (PE:EtOAc=10:1) showed the reaction was complete. Then the reaction solution was separated and the organic layer was dried over Na₂SO₄, concentrated to give the crude product, which was purified by silica gel chromatograph (PE:EtOAc=80:1) to give the title compound (3.8 g, 70.3% for 2 steps) as a solid.

$^1$H-NMR (400 MHz, CDCl₃): δ=7.84 (d, J=7.94 Hz, 1H) 7.59 (d, J=6.17 Hz, 2H) 7.01 (d, J=8.38 Hz, 1H) 4.14 (d, J=17.20 Hz, 1H) 3.75 (d, J=17.20 Hz, 1H) 3.64 (q, J=8.09 Hz, 2H) 3.29-3.38 (m, 2H) 1.63 (s, 9H)

Step 8: 4-[5-(3,5-Dichloro-4-fluoro-phenyl)-5-(trifluoromethyl)-4H-isoxazol-3-yl]-2,3-dihydrobenzothiophene-7-carboxylic acid

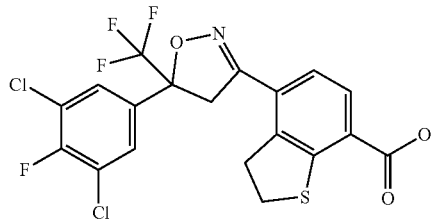 [SMILES: O=C(O)c1ccc(C2=NOC(c3cc(Cl)c(F)c(Cl)c3)(C(F)(F)F)C2)c2c1SCC2]

To a solution of tert-butyl 4-[5-(3,5-dichloro-4-fluoro-phenyl)-5-(trifluoromethyl)-4H-isoxazol-3-yl]-2,3-dihydrobenzothiophene-7-carboxylate (3.8 g, 7.1 mmol) in DCM (100 mL) was added TFA (30 mL), then the mixture was stirred at r.t. for 3 h. TLC (PE:EtOAc=10:1) showed the reaction was complete. After removal of the solvent, the residue was washed with hexane to give the title compound (2.8 g, 82%) as a solid.

$^1$H-NMR (400 MHz, DMSO-d₆): δ=13.29 (br. s., 1H) 7.75-7.91 (m, 4H) 7.35 (d, J=7.94 Hz, 1H) 4.30-4.43 (m, 2H), 3.45-3.52 (m, 2H) 3.21-3.28 (m, 2H)

Step 9: 4-[5-(3,5-Dichloro-4-fluoro-phenyl)-5-(trifluoromethyl)-4H-isoxazol-3-yl]-N-(1,1-dioxothietan-3-yl)-2,3-dihydrobenzothiophene-7-carboxamide (compound I-7)

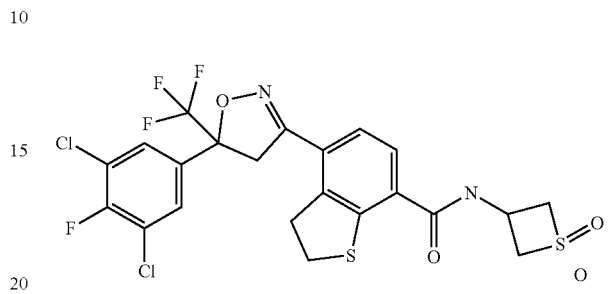

To a solution of 4-[5-(3,5-dichloro-4-fluoro-phenyl)-5-(trifluoromethyl)-4H-isoxazol-3-yl]-2,3-dihydrobenzothiophene-7-carboxylic acid (200 mg, 0.42 mmol), 1,1-dioxothietan-3-amine hydrochloride (0.08 g, 0.5 mmol, 1.2 equiv.) and PyBrop (0.23 g, 0.5 mmol, 1.2 equiv.) in dichloromethane (20 mL) was added Hünig base (0.17 g, 1.33 mmol, 3.2 equiv.) at room temperature. The mixture was stirred over night and a saturated aqueous solution of NH₄Cl was added. Extraction with dichloromethane (50 mL×2) afforded an organic layer that was washed with water, dried over Na₂SO₄ and concentrated in vacuum. Purification of the residue via silica gel chromatography afforded the title compound (190 mg, 76%).

$^1$H-NMR (400 MHz, CDCl₃): δ=7.59 (m, 3H), 7.28 (m, 1H), 7.01 (m, 1H), 4.86 (m, 1H), 4.61 (m, 2H), 4.15 (m, 3H), 3.76 (d, 1H), 3.50-3.68 (m, 2H), 3.31 (m, 2H).

Example 2

In analogy to steps 5 to 9 of example 1, compounds of the formulae I-1 to I-5, I-11 to I-12, I-14 to I-19 and I-28 were prepared. The starting material tert-butyl 4-bromo-2,3-dihydrobenzofuran-7-carboxylate was used instead.

Step 1: tert-Butyl 4-bromo-2,3-dihydrobenzofuran-7-carboxylate

To a solution of tert-butyl 4-bromo-2-fluoro-3-(2-hydroxyethyl)benzoate (10.0 g, 31.4 mmol) in DMF (2 L) was added Cs₂C0₃ (15.4 g, 47.2 mmol), the mixture was stirred at 90° C. for 14 h. TLC (PE:EtOAc=5:1) showed the reaction was complete. After removal of the solvent, the residue was dissolved in water and extracted with EtOAc (300 mL×3), the organic layer was dried over Na₂SO₄ and concentrated to give the crude product, which was purified by column chromatography (PE:EtOAc=10:1) to give the title compound (6.5 g, 69.5%) as a solid.

$^1$H-NMR (400 MHz, CDCl₃): δ=7.52 (d, J=8.38 Hz, 1H) 6.98 (d, J=8.82 Hz, 1H) 4.75 (t, J=8.82 Hz, 2H) 3.21 (t, J=8.82 Hz, 2H) 1.57 (s, 9H).

Example 3

In analogy to steps 5 to 9 of example 1, compounds of the formulae I-22 to I-24, I-29, I-35 to I-41 were prepared. The starting material methyl 7-bromo-1,3-dihydroisobenzofuran-4-carboxylate was used instead.

Step 1: 1,2-Bis(bromomethyl)-3-nitro-benzene

To a solution of 1,2-dimethyl-3-nitro-benzene (102 g, 0.675 mol) and NBS (258.3 g, 1.45 mol) in CCl$_4$ (450 mL) was added benzoyl peroxide (1.68 g, 6.8 mmol) in one portion. The reaction mixture was stirred and refluxed at 90° C. under N$_2$ for 2 h, additional benzoyl peroxide (6.5 g, 0.027 mol) was added and the reaction mixture was stirred and refluxed at 90° C. under N$_2$ for 2 h and then cooled to room temperature. The reaction mixture was filtered and washed with CCl$_4$. The yellow filtrate was concentrated to give 1,2-bis(bromomethyl)-3-nitrobenzene as a crude oil. The crude product was purified by column chromatography (PE:EtOAc=60:1) to give the title compound (crude 180 g, 87.3%) as an oil.

$^1$H-NMR (400 MHz, CDCl$_3$): δ=7.85 (d, J=7.94 Hz, 1H) 7.73 (d, J=7.94 Hz, 1H) 7.47-7.55 (m, 1H) 4.87 (s, 2H) 4.78 (s, 2H).

Step 2: 4-Nitro-1,3-dihydroisobenzofuran

To a flask containing 1,2-bis(bromomethyl)-3-nitro-benzene (180 g, 0.59 mol,) was added neutralized alumina (816 g, 8 mol) and toluene (1 L) and the suspension was heated at an external temperature of 120° C. for 18 hours. The reaction mixture was filtered to remove the alumina and washed with ethyl acetate. The filtrate was concentrated to give a yellow solid which was purified by silica gel chromatography (PE:EtOAc=20:1) to give the title compound (17.5 g, 18%) as an oil.

$^1$H-NMR (400 MHz, CDCl$_3$): δ=8.14 (d, J=7.94 Hz, 1H), 7.55-7.59 (m, 1H), 7.47-7.52 (m, 1H), 5.54 (s, 2H), 5.21 (s, 2H).

Step 3: 1,3-Dihydroisobenzofuran-4-amine

A solution of 4-nitro-1,3-dihydroisobenzofuran (50 g, 0.303 mol) in MeOH (800 mL) was hydrogenated with Pd/C (5 g) under H$_2$ at 50 psi. The reaction was filtered and then concentrated to give the desired title compound (35 g, 85.5%) as a solid.

$^1$H-NMR (400 MHz, CDCl$_3$): δ=7.05-7.15 (m, 1H), 6.68 (d, J=7.15 Hz, 1H), 6.58 (d, J=7.65 Hz, 1H), 5.12 (br. s., 2H), 5.04 (br. s., 2H), 3.56 (br. s., 2H).

Step 4: tert-Butyl N-(1,3-dihydroisobenzofuran-4-yl)carbamate

To a solution of 1,3-dihydroisobenzofuran-4-amine (36 g, 0.267 mol) in THF (500 mL) was added TEA (54.4 g, 0.533 mol) and Boc$_2$O (87.2 g, 0.400 mol) in dropwise. The mixture was stirred and heated at an external temperature of 80° C. for 6 h. The reaction was filtered, diluted into water (300 mL), extracted with EtOAc (500 mL×3), the organic layer was washed brine (100 mL), dried over Na$_2$SO$_4$, filtered and concentrated under reduce pressure to give the crude product. The crude product was purified by column chromatography (PE:EtOAc=30:1) to give the title compound (35 g, 55.9%) as a solid.

$^1$H-NMR (400 MHz, CDCl$_3$): δ=7.59 (d, J=7.94 Hz, 1H), 7.23-7.32 (m, 1H), 6.98 (d, J=7.50 Hz, 1H), 6.30 (br. s., 1H), 5.15 (s, 2H), 5.11 (s, 2H), 1.55 (s, 9H).

Step 5: tert-Butyl N-(7-bromo-1,3-dihydroisobenzofuran-4-yl)carbamate

To a solution of tert-butyl N-(1,3-dihydroisobenzofuran-4-yl)carbamate (25 g, 0.085 mol) in DMF (300 mL), NBS (16.6 g, 0.094 mol) was added in portions at 0° C. The reaction mixture was stirred at 25° C. under N$_2$ for 3 h. The reaction was filtered, diluted into water (1000 mL), extracted with EtOAc (500 mL×3), the organic layer was washed brine (300 mL), dried over Na$_2$SO$_4$, filtered and concentrated under reduced pressure to give the crude product. The crude product was purified by column chromatography (PE:EtOAc=50:1) to give the title compound (25 g, 74.8%).

$^1$H-NMR (400 MHz, CDCl$_3$): δ=7.49 (d, J=8.28 Hz, 1H), 7.33 (d, J=8.53 Hz, 1H), 6.26 (br. s., 1H), 5.16 (s, 2H), 5.08 (s, 2H), 1.51 (s, 9H).

Step 6: Methyl 7-(tert-butoxycarbonylamino)-1,3-dihydroisobenzofuran-4-carboxylate To a stirred solution of tert-butyl N-(7-bromo-1,3-dihydroisobenzofuran-4-yl)carbamate (30 g, 0.095 mol) in MeOH (800 mL) in a 1 L autoclave, Na$_2$CO$_3$ (30.4 g, 0.286 mol) and Pd(dppf)Cl$_2$ (5 g) was added, the mixture was stirred and heated at 120° C. under CO at 1 MPa for 18 h. After cooling to room temperature, the mixture was filtered, concentrated, the residue was purified by chromatography on silica gel (PE:EtOAc=10:1) to give the title compound (24 g, 85.7%).

$^1$H-NMR (400 MHz, CDCl$_3$): δ=7.93 (q, J=8.53 Hz, 2H) 6.28 (br. s., 1H) 5.42 (s, 2H) 5.10 (s, 2H) 3.90 (s, 3H) 1.55 (s, 9H).

Step 7: Methyl 7-amino-1,3-dihydroisobenzofuran-4-carboxylate

To a stirred solution of methyl 7-(tert-butoxycarbonylamino)-1,3-dihydroisobenzofuran-4-carboxylate (20 g, 0.095 mol) in DCM (800 mL), TFA (80 mL) was added dropwise at 0°C, the mixture was stirred at 18° C. for 18 h. The mixture was concentrated, diluted into aq. Na$_2$CO$_3$ solution (500 mL), extracted with EtOAc (300 mL×3) dried over Na$_2$SO$_4$, concentrated to give the title compound (15 g, crude).

$^1$H-NMR (400 MHz, CDCl$_3$): δ=7.76 (d, J=8.28 Hz, 1H) 6.56 (d, J=8.28 Hz, 1H) 5.35 (s, 2H) 4.99 (s, 2H) 3.83 (s, 3H)

Step 8: Methyl 7-bromo-1,3-dihydroisobenzofuran-4-carboxylate

To a stirred solution of methyl 7-amino-1,3-dihydroisobenzofuran-4-carboxylate (15 g, 0.078 mol) in MeCN (500 mL), CuBr (16.8 g, 0.116 mol) and tert-butyl nitrite (12 g, 0.116 mol) was added, the mixture was stirred at 68° C. for 18 h. The mixture was filtered, concentrated, the residue was purified by chromatography on silica gel (PE:EtOAc=50:1) to give the title compound (15 g, crude).

$^1$H-NMR (400 MHz, CDCl$_3$): δ=8.05 (d, J=7.94 Hz, 1H) 7.86 (d, J=7.94 Hz, 1H) 5.38 (dd, J=10.36, 1.54 Hz, 4H) 3.95 (s, 3H) 2.64 (s, 3H).

Example 4

In analogy to example 3, compounds of formulae I-51 and I-52 were prepared using 4-nitro-1,3-dihydro-2-benzothiophene as starting material To a solution of 1,2-bis(bromomethyl)-3-nitro-benzene (185.0 g, 0.6 mol) in EtOH (3 L) was added the Na₂S.9H2O (144.2 g, 0.6 mol), then the mixture was heated under reflux for 10 h. The mixture was concentrated to remove EtOH, then water (500 mL) was added and extracted with DCM (500 mL×4), the combined organic layer was washed with brine (300 mL×2), dried over Na₂SO₄ and concentrated, purified by silica gel column chromatography (PE:EtOAc=50: 1 to 20:1) to give the title compound (80.1 g, yield 36.9%).

¹H-NMR (400 MHz, CDCl₃): δ=4.34 (s, 2H) 4.72 (s, 2H) 7.38-7.48 (m, 1H) 7.57 (d, J=7.5 Hz, 1H) 8.11 (d, J=8.4 Hz, 1H).

Example 5: 7-[5-(3,5-Dichloro-4-fluoro-phenyl)-5-(trifluoromethyl)-4H-isoxazol-3-yl]-2,2-dioxo-1,3-dihydro-2-benzothiophene-4-carboxylic acid

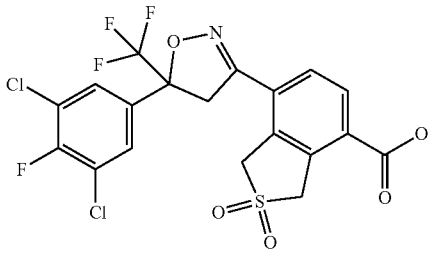 [SMILES: O=C(O)c1ccc(C2=NOC(c3cc(Cl)c(F)c(Cl)c3)(C(F)(F)F)C2)c2c1CS(=O)(=O)C2]

To a solution of 7-[5-(3,5-dichloro-4-fluoro-phenyl)-5-(trifluoromethyl)-4H-isoxazol-3-yl]-1,3-dihydro-2-benzothiophene-4-carboxylic acid (2.5 g, 0.0052 mol) in DCM (100 mL) was added m-CPBA (2.4 g, 0.0115 mol) at 0° C. Then it was stirred at 20° C. under N₂ for 12 h. The reaction mixture was concentrated. The crude product was purified by preparative HPLC to give the title compound (1.5 g, 58%).

¹H-NMR (400 MHz, CDCl₃): δ=4.33-4.51 (m, 2H) 4.63 (d, J=5.29 Hz, 2H) 4.77 (s, 2H) 7.71-7.85 (m, 3H) 8.07 (d, J=8.38 Hz, 1H).

Example 6

In analogy to example 5, all other sulfur oxidation products, such as compounds I-42 to I-50 were prepared.

Example 7: Synthesis of N-[[4-[5-(3,5-dichloro-4-fluoro-phenyl)-5-(trifluoromethyl)-4H-isoxazol-3-yl]-2,3-dihydrobenzofuran-7-yl]methyl]butanamide (compound I-16)

Step 1: [4-[5-(3,5-Dichloro-4-fluoro-phenyl)-5-(trifluoromethyl)-4H-isoxazol-3-yl]-2,3-dihydrobenzofuran-7-yl]methanol

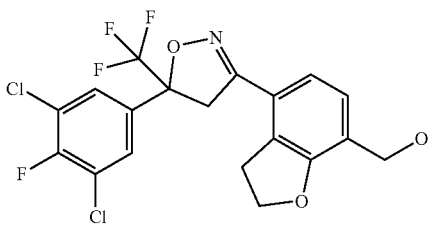

To a solution of 4-[5-(3,5-dichloro-4-fluoro-phenyl)-5-(trifluoromethyl)-4H-isoxazol-3-yl]-2,3-dihydrobenzofuran-7-carboxylic acid (6 g, 13 mmol) in THF (100 mL) was added BH₃.Me₂S (3.9 mL, 39 mmol) at 0° C. The mixture was stirred at 25° C. for 15 h. The reaction mixture was quenched with MeOH (39 mL) and concentrated to give the product, which was purified by column chromatography (PE:EtOAc=20:1~10:1) to give the title compound (4 g, 69%).

¹H-NMR (400 MHz, CDCl₃): δ=3.42-3.52 (m, 2H) 3.73 (d, J=17.07 Hz, 1H) 4.14 (br. s., 1H) 4.64-4.73 (m, 4H) 6.82 (d, J=7.78 Hz, 1H) 7.20 (d, J=7.78 Hz, 1H) 7.59 (d, J=6.02 Hz, 2H).

Step 2: [4-[5-(3,5-Dichloro-4-fluoro-phenyl)-5-(trifluoromethyl)-4H-isoxazol-3-yl]-2,3-dihydrobenzofuran-7-yl]methyl methanesulfonate

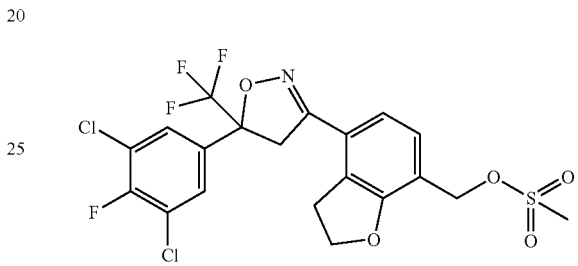

To a solution of [4-[5-(3,5-dichloro-4-fluoro-phenyl)-5-(trifluoromethyl)-4H-isoxazol-3-yl]-2,3-dihydrobenzofuran-7-yl]methanol (4 g, 9 mmol) in DCM (60 mL) was added TEA (2.7 g, 27 mmol) and MsCl (2 g, 18 mmol) at 0° C. The mixture was stirred at 25° C. for 10 h. Then the reaction mixture was diluted with aq. NH₄Cl (100 mL) and extracted with EtOAc (100 mL×3), the combined organic layers were dried over Na₂SO₄ and concentrated, then the residue was purified by silica gel chromatograph (PE:EtOAc=15:1~10:1) to give the title compound (4.6 g, 98%).

¹H-NMR (400 MHz, CDCl₃): δ=3.16 (s, 3H) 3.46-3.57 (m, 2H) 3.70 (s, 1H) 4.16 (s, 1H) 4.61 (s, 2H) 4.72 (t, J=8.91 Hz, 2H) 6.84 (d, J=8.03 Hz, 1H) 7.23-7.29 (m, 1H) 7.60 (d, J=6.02 Hz, 2H)

Step 3: 3-[7-(Azidomethyl)-2,3-dihydrobenzofuran-4-yl]-5-(3,5-dichloro-4-fluoro-phenyl)-5-(trifluoromethyl)-4H-isoxazole

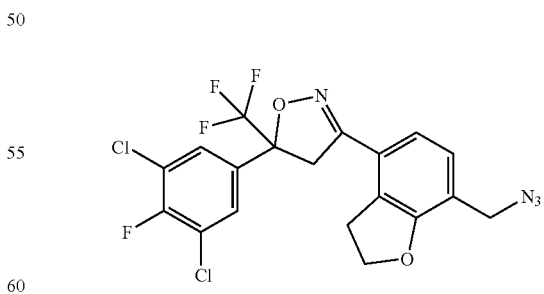

To a solution of [4-[5-(3,5-dichloro-4-fluoro-phenyl)-5-(trifluoromethyl)-4H-isoxazol-3-yl]-2,3-dihydrobenzofuran-7-yl]methyl methanesulfonate (4.6 g, 9 mmol) in DMF (60 mL) was added NaN₃ (1.2 g, 18 mmol) and the mixture was stirred at 25° C. under N₂ for 13 h. The reaction mixture was diluted with water (100 mL) and extracted with MTBE (100 mL×3), the combined organic layers are dried over with Na$_2$SO$_4$ and concentrated to give the title compound (4 g, 97.6%).

$^1$H-NMR (400 MHz, CDCl$_3$): δ=3.38-3.49 (m, 2H) 3.71 (d, J=17.64 Hz, 1H) 4.06-4.11 (m, 1H) 4.27 (br. s., 2H) 4.60 (t, J=8.82 Hz, 2H) 6.80 (d, J=7.94 Hz, 1H) 7.08 (d, J=7.94 Hz, 1H) 7.53 (d, J=5.73 Hz, 2H).

Step 4: [4-[5-(3,5-Dichloro-4-fluoro-phenyl)-5-(trifluoromethyl)-4H-isoxazol-3-yl]-2,3-dihydrobenzofuran-7-yl]methanamine

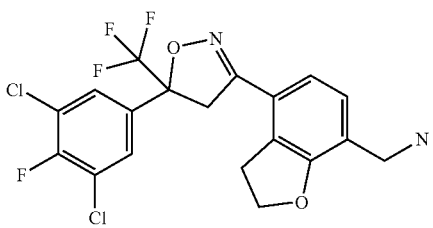 [SMILES: NCc1ccc(C2=NOC(c3cc(Cl)c(F)c(Cl)c3)(C(F)(F)F)C2)c2c1OCC2]

To a solution of 3-[7-(azidomethyl)-2,3-dihydrobenzofuran-4-yl]-5-(3,5-dichloro-4-fluoro-phenyl)-5-(trifluoromethyl)-4H-isoxazole (4 g, 8 mmol) in THF (80 mL) and H$_2$O (80 mL) was added PPh$_3$ (2.7 g, 10 mmol), the mixture was stirred at 85° C. under N$_2$ for 2 h. The mixture was extracted with EtOAc (100 mL×3), the combined organic layers are dried over Na$_2$SO$_4$ and concentrated, then the residue was purified by silica gel chromatography (DCM:MeOH=15:1~10:1) to give the title compound (1.5 g, 40%).

$^1$H-NMR (400 MHz, CDCl$_3$): δ=3.39-3.54 (m, 2H) 3.72 (d, J=17.20 Hz, 1H) 3.83 (s, 2H) 4.12 (d, J=17.20 Hz, 1H), 4.66 (t, J=8.82 Hz, 2H) 6.80 (d, J=7.50 Hz, 1H) 7.13 (d, J=7.94 Hz, 1H) 7.59 (d, J=6.17 Hz, 2H).

Step 5: N-[[4-[5-(3,5-Dichloro-4-fluoro-phenyl)-5-(trifluoromethyl)-4H-isoxazol-3-yl]-2,3-dihydrobenzofuran-7-yl]methyl]butanamide (compound I-16)

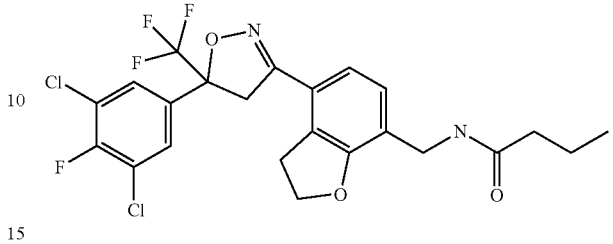

To a solution of 4-[5-(3,5-dichloro-4-fluoro-phenyl)-5-(trifluoromethyl)-4H-isoxazol-3-yl]-2,3-dihydrobenzofuran-7-yl]methanamine (0.15 g, 0.33 mmol) in THF (10 mL) was added triethylamine (0.07 g, 0.67 mmol, 2.0 equiv.), followed by n-butyric chloride (0.04 g, 0.4 mmol, 1.2 equiv.) at room temperature and stirred over night. The reaction mixture was concentrated in vacuum and the residue was purified via silica gel chromatography to yield the title compound (0.11 g, 65%).

$^1$H-NMR (400 MHz, CDCl$_3$): δ=0.93 (t, 3H), 1.63 (m, 2H), 2.18 (m, 2H), 3.37-3.55 (m, 2H), 3.72 (d, 1H), 4.11 (d, 1H), 4.40 (m, 1H), 4.65 (m, 2H), 6.10 (br. s, 1H), 6.79 (m, 1H), 7.17 (m, 1H), 7.69 (m, 2H).

In analogy to the above described examples, compounds I-1 to I-57 as shown in tables C.1 and C.2 were prepared.

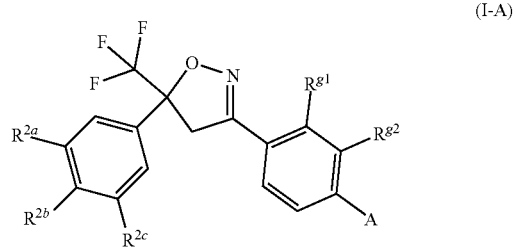

(I-A)

TABLE C.1 compounds of formula I-A with R$^{2a}$ = R$^{2c}$ = Cl, R$^{2b}$ = F

| No. | R$^{g1}$ | R$^{g2}$ | A | method | t$_R$ [min] | m/z [M + H]$^+$ |
|---|---|---|---|---|---|---|
| I-1 | # | —CH$_2$—CH$_2$—O—* | pyrimidin-2-ylmethylcarbamoyl | 1 | 1.354 | 554.9 |
| I-2 | # | —CH$_2$—CH$_2$—O—* | (1,1-dioxothietan-3-yl)carbamoyl | 1 | 1.341 | 567.0 |
| I-3 | # | —CH$_2$—CH$_2$—O—* | [2-oxo-2-(2,2,2-trifluoroethylamino)ethyl]carbamoyl | 1 | 1.366 | 602.1 |
| I-4 | # | —CH$_2$—CH$_2$—O—* | 2-pyridylmethylcarbamoyl | 1 | 1.169 | 554.1 |
| I-5 | # | —CH$_2$—CH$_2$—O—* | [2-(allylamino)-2-oxo-ethyl]carbamoyl | 1 | 1.336 | 560.1 |
| I-6 | # | —CH$_2$—CH$_2$—S—* | pyrimidin-2-ylmethylcarbamoyl | 1 | 1.356 | 570.9 |
| I-7 | # | —CH$_2$—CH$_2$—S—* | (1,1-dioxothietan-3-yl)carbamoyl | see Example 1 | | |
| I-8 | # | —CH$_2$—CH$_2$—S—* | [2-oxo-2-(2,2,2-trifluoroethylamino)ethyl]carbamoyl | 1 | 1.353 | 618.0 |
| I-9 | # | —CH$_2$—CH$_2$—S—* | 2-pyridylmethylcarbamoyl | 1 | 1.192 | 570.0 |
| I-10 | # | —CH$_2$—CH$_2$—S—* | [2-(allylamino)-2-oxo-ethyl]carbamoyl | 1 | 1.347 | 576.0 |
| I-11 | # | —CH$_2$—CH$_2$—O—* | (3,3,3-trifluoropropanoylamino)methyl | 1 | 1.407 | 559.0 |
| I-12 | # | —CH$_2$—CH$_2$—O—* | [(4S)-2-ethyl-3-oxo-isoxazolidin-4-yl]carbamoyl | 1 | 1.387 | 576.0 |
| I-13 | # | —CH$_2$—CH$_2$—S—* | [(4S)-2-ethyl-3-oxo-isoxazolidin-4-yl]carbamoyl | 1 | 1.385 | 592.0 |

TABLE C.1-continued compounds of formula I-A with $R^{2a} = R^{2c} = Cl$, $R^{2b} = F$

| No. | $R^{g1}$ | $R^{g2}$ | A | method | $t_R$ [min] | m/z [M + H]$^+$ |
|---|---|---|---|---|---|---|
| I-14 | #—CH$_2$—CH$_2$—O—* | | [(2-ethylsulfonylacetyl)amino]methyl | 1 | 1.334 | 583.0 |
| I-15 | #—CH$_2$—CH$_2$—O—* | | (cyclopropanecarbonylamino)methyl | 1 | 1.385 | 517.0 |
| I-16 | #—CH$_2$—CH$_2$—O—* | | (butanoylamino)methyl | 1 | 1.402 | 519.0 |
| I-17 | #—CH$_2$—CH$_2$—O—* | | acetamidomethyl | 1 | 1.318 | 491.0 |
| I-18 | #—CH$_2$—CH$_2$—O—* | | (propanoylamino)methyl | 1 | 1.360 | 505.0 |
| I-19 | #—CH$_2$—CH$_2$—O—* | | [(2-methylsulfonylacetyl)amino]methyl | 1 | 1.306 | 569.1 |
| I-20 | #—CH$_2$—CH$_2$—S(=O)—* | | pyrimidin-2-ylmethylcarbamoyl | 1 | 1.146 | 586.9 |
| I-21 | #—CH$_2$—CH$_2$—S(=O)$_2$—* | | pyrimidin-2-ylmethylcarbamoyl | 1 | 1.215 | 602.9 |
| I-22 | #—CH$_2$—O—CH$_2$—* | | [2-oxo-2-(2,2,2-trifluoroethylamino)ethyl]carbamoyl | 1 | 1.331 | 601.9 |
| I-23 | #—CH$_2$—O—CH$_2$—* | | (2-ethyl-3-oxo-isoxazolidin-4-yl)carbamoyl | 1 | 1.336 | 576.0 |
| I-24 | #—CH$_2$—O—CH$_2$—* | | pyrimidin-2-ylmethylcarbamoyl | 1 | 1.303 | 555.0 |
| I-26 | #—CH$_2$—CH$_2$—CH$_2$—O—* | | methoxycarbonyl | 1 | 1.443 | 492.0 |
| I-27 | #—CH$_2$—CH$_2$—CH$_2$—O—* | | CO$_2$H | 1 | 1.341 | 477.9 |
| I-28 | #—CH$_2$—CH$_2$—O—* | | (2-ethyl-3-oxo-isoxazolidin-4-yl)carbamoyl | 1 | 1.404 | 576.0 |
| I-29 | #—CH$_2$—O—CH$_2$—* | | 2-pyridylmethylcarbamoyl | 1 | 1.154 | 554.0 |
| I-30 | #—CH$_2$—CH$_2$—CH$_2$—O—* | | pyrimidin-2-ylmethylcarbamoyl | 1 | 1.352 | 569.0 |
| I-31 | #—CH$_2$—CH$_2$—CH$_2$—O—* | | 2-pyridylmethylcarbamoyl | 2 | 1.162 | 568.0 |
| I-32 | #—CH$_2$—CH$_2$—CH$_2$—O—* | | [2-oxo-2-(2,2,2-trifluoroethylamino)ethyl]carbamoyl | 1 | 1.357 | 616.0 |
| I-33 | #—CH$_2$—CH$_2$—CH$_2$—O—* | | (1,1-dioxothietan-3-yl)carbamoyl | 1 | 1.328 | 580.9 |
| I-34 | #—CH$_2$—CH$_2$—CH$_2$—O—* | | [(4R)-2-ethyl-3-oxo-isoxazolidin-4-yl]carbamoyl | 1 | 1.376 | 590.0 |
| I-35 | #—CH$_2$—O—CH$_2$—* | | [2-(allylamino)-2-oxo-ethyl]carbamoyl | 1 | 1.300 | 229.6 |
| I-36 | #—CH$_2$—O—CH$_2$—* | | cyclobutylcarbamoyl | 1 | 1.423 | 516.7 |
| I-37 | #—CH$_2$—O—CH$_2$—* | | thietan-3-ylcarbamoyl | 1 | 1.372 | 534.9 |
| I-38 | #—CH$_2$—O—CH$_2$—* | | cyclopropylmethylcarbamoyl | 1 | 1.377 | 517.0 |
| I-39 | #—CH$_2$—O—CH$_2$—* | | cyclopropylcarbamoyl | 1 | 1.325 | 502.9 |
| I-40 | #—CH$_2$—O—CH$_2$—* | | [(4S)-2-ethyl-3-oxo-isoxazolidin-4-yl]carbamoyl | 1 | 1.296 | 575.9 |
| I-41 | #—CH$_2$—O—CH$_2$—* | | (1,1-dioxothietan-3-yl)carbamoyl | 1 | 1.259 | 567.0 |
| I-42 | #—CH$_2$—S(=O)$_2$—CH$_2$—* | | pyrimidin-2-ylmethylcarbamoyl | 1 | 1.239 | 602.6 |
| I-43 | #—CH$_2$—S(=O)$_2$—CH$_2$—* | | 2-pyridylmethylcarbamoyl | 1 | 1.137 | 603.4 |
| I-44 | #—CH$_2$—S(=O)$_2$—CH$_2$—* | | [2-oxo-2-(2,2,2-trifluoroethylamino)ethyl]carbamoyl | 1 | 1.235 | 649.9 |
| I-45 | #—CH$_2$—S(=O)$_2$—CH$_2$—* | | [2-(allylamino)-2-oxo-ethyl]carbamoyl | 1 | 1.206 | 608.0 |
| I-46 | #—CH$_2$—S(=O)$_2$—CH$_2$—* | | cyclobutylcarbamoyl | 1 | 1.297 | 565.0 |
| I-47 | #—CH$_2$—S(=O)$_2$—CH$_2$—* | | cyclopropylmethylcarbamoyl | 1 | 1.332 | 564.6 |
| I-48 | #—CH$_2$—S(=O)$_2$—CH$_2$—* | | cyclopropylcarbamoyl | 1 | 1.248 | 550.9 |
| I-49 | #—CH$_2$—S(=O)$_2$—CH$_2$—* | | [(4S)-2-ethyl-3-oxo-isoxazolidin-4-yl]carbamoyl | 1 | 1.266 | 623.6 |
| I-50 | #—CH$_2$—S(=O)$_2$—CH$_2$—* | | thietan-3-ylcarbamoyl | 1 | 1.322 | 582.5 |
| I-51 | #—CH$_2$—S—CH$_2$—* | | (1,1-dioxothietan-3-yl)carbamoyl | 1 | 1.380 | 580.8 |
| I-52 | #—CH$_2$—S—CH$_2$—* | | pyrimidin-2-ylmethylcarbamoyl | 1 | 1.333 | 571.0 |
| I-53 | #—CH$_2$—S(=O)$_2$—CH$_2$—* | | (1,1-dioxothietan-3-yl)carbamoyl | 1 | 1.332 | 564.6 |
| I-54 | #—CH$_2$—S(=O)$_2$—CH$_2$—* | | [(4R)-2-ethyl-3-oxo-isoxazolidin-4-yl]carbamoyl | 1 | 1.249 | 624.0 |
| I-58 | #—CH$_2$—CH$_2$—CH$_2$—O—* | | (butanoylamino)methyl | 1 | 1.344 | 519.1[a] |

[a]H-NMR of I-58 (400 MHz, CDCl$_3$): δ = 1.15 (m, 3H), 1.94-2.08 (m, 2H), 2.22 (m, 2H), 3.01 (m, 2H), 3.73 (d, 1H), 4.09 (d, 1H), 4.18-4.29 (m, 2H), 4.40 (d, 2H), 5.97 (m, 1H), 6.85 (d, 1H), 7.17 (d, 1H), 7.58 (m, 2H).
attachment point in position of $R^{g1}$
*attachment point in position of $R^{g2}$

TABLE C.2 compounds of formula I-A with $R^{2a} = R^{2c} = Cl$, $R^{2b} = H$

| No. | $R^{g1}$ | $R^{g2}$ | A | method | $t_R$ [min] | m/z [M + H]$^+$ |
|---|---|---|---|---|---|---|
| I-56 | #—O—CH$_2$—O—* | | pyrimidin-2-ylmethylcarbamoyl | 1 | 1.272 | 539.0 |
| I-57 | #—CH$_2$—CH$_2$—CH$_2$—O—* | | pyrimidin-2-ylmethylcarbamoyl | 1 | 1.377 | 552.4 |

II. Evaluation of Pesticidal Activity

The activity of the compounds of formula I of the present invention can be demonstrated and evaluated by the following biological test.

B.1 Diamond Back Moth (*Plutella xylostella*)

The active compound was dissolved at the desired concentration in a mixture of 1:1 (vol:vol) distilled water: aceteone. Surfactant (Kinetic HV) was added at a rate of 0.01% (vol/vol).The test solution was prepared at the day of use.

Leaves of cabbage were dipped in test solution and air-dried. Treated leaves were placed in petri dishes lined with moist filter paper and inoculated with ten $3^{rd}$ instar larvae. Mortality was recorded 72 hours after treatment. Feeding damages were also recorded using a scale of 0-100%.

In this test, compounds I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-28, I-29, I-30, I-31, I-32, I-33, I-34, I-35, I-36, I-37, I-38, I-39, I-41, I-42, I-44, I-46, I-47, I-48, I-51, I-52, I-56, I-57 at 300 ppm showed at least 75% mortality in comparison with untreated controls.

B.2 Green Peach Aphid (*Myzus persicae*)

For evaluating control of green peach aphid (*Myzus persicae*) through systemic means the test unit consisted of 96-well-microtiter plates containing liquid artificial diet under an artificial membrane.

The compounds were formulated using a solution containing 75% v/v water and 25% v/v DMSO. Different concentrations of formulated compounds were pipetted into the aphid diet, using a custom built pipetter, at two replications.

After application, 5-8 adult aphids were placed on the artificial membrane inside the microtiter plate wells. The aphids were then allowed to suck on the treated aphid diet and incubated at about 23±1° C. and about 50±5% relative humidity for 3 days. Aphid mortality and fecundity was then visually assessed.

In this test, compounds I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-26, I-28, I-30, I-31, I-32, I-33, I-34, I-37, I-41, I-42, I-43, I-44, I-45, I-46, I-47, I-48, I-49, I-50, I-54, I-56, I-57 at 2500 ppm showed at least 75% mortality in comparison with untreated controls.

B.3 Vetch Aphid (*Megoura viciae*)

For evaluating control of vetch aphid (*Megoura viciae*) through contact or systemic means the test unit consisted of 24-well-microtiter plates containing broad bean leaf disks.

The compounds were formulated using a solution containing 75% v/v water and 25% v/v DMSO. Different concentrations of formulated compounds were sprayed onto the leaf disks at 2.5 μl, using a custom built micro atomizer, at two replications.

After application, the leaf disks were air-dried and 5-8 adult aphids placed on the leaf disks inside the microtiter plate wells. The aphids were then allowed to suck on the treated leaf disks and incubated at about 23±10C and about 50±5% relative humidity for 5 days. Aphid mortality and fecundity was then visually assessed.

In this test, compounds I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-28, I-30, I-31, I-32, I-33, I-34, I-37, I-41, I-43, I-46, I-47, I-48, I-50, I-54 at 2500 ppm showed at least 75% mortality in comparison with untreated controls.

B.4 Tobacco Budworm (*Heliothis virescens*)

For evaluating control of tobacco budworm (*Heliothis virescens*) the test unit consisted of 96-well-microtiter plates containing an insect diet and 15-25 *H. virescens* eggs.

The compounds were formulated using a solution containing 75% v/v water and 25% v/v DMSO. Different concentrations of formulated compounds were sprayed onto the insect diet at 10 μl, using a custom built micro atomizer, at two replications.

After application, microtiter plates were incubated at about 28±10C and about 80±5% relative humidity for 5 days. Egg and larval mortality was then visually assessed.

In this test, compounds I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-26, I-28, I-30, I-31, I-32, I-33, I-34, I-37, I-40, I-41, I-42, I-43, I-44, I-45, I-46, I-47, I-48, I-49, I-50, I-54, I-56, I-57 at 2500 ppm showed at least 75% mortality in comparison with untreated controls.

B.5 Boll Weevil (*Anthonomus grandis*)

For evaluating control of boll weevil (*Anthonomus grandis*) the test unit consisted of 96-well-microtiter plates containing an insect diet and 5-10 *A. grandis* eggs.

The compounds were formulated using a solution containing 75% v/v water and 25% v/v DMSO. Different concentrations of formulated compounds were sprayed onto the insect diet at 5 μl, using a custom built micro atomizer, at two replications.

After application, microtiter plates were incubated at about 25±1° C. and about 75±5% relative humidity for 5 days. Egg and larval mortality was then visually assessed.

In this test, I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-26, I-27, I-28, I-30, I-31, I-32, I-33, I-34, I-37, I-40, I-41, I-42, I-43, I-44, I-45, I-46, I-47, I-48, I-49, I-50, I-54, I-56, I-57 at 2500 ppm showed at least 75% mortality in comparison with untreated controls.

B.6 Mediterranean Fruitfly (*Ceratitis capitata*)

For evaluating control of Mediterranean fruitfly (*Ceratitis capitata*) the test unit consisted of microtiter plates containing an insect diet and 50-80 *C. capitata* eggs. The compounds were formulated using a solution containing 75% v/v water and 25% v/v DMSO. Different concentrations of formulated compounds were sprayed onto the insect diet at 5 μl, using a custom built micro atomizer, at two replications.

After application, microtiter plates were incubated at about 28±1° C. and about 80+5% relative humidity for 5 days. Egg and larval mortality was then visually assessed.

In this test, I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-28, I-30, I-31, I-32, I-33, I-34, I-37, I-40, I-41, I-42, I-43, I-44, I-45, I-46, I-47, I-48, I-49, I-50, I-54 at 2500 ppm showed at least 75% mortality in comparison with untreated controls.

B.7 Orchid Thrips (*Dichromothrips Corbetti*)

Dichromothrips corbettiadults used for bioassay were obtained from a colony maintained continuously under laboratory conditions. For testing purposes, the test compound is diluted in a 1:1 mixture of acetone:water (vol:vol), plus Kinetic HV at a rate of 0.01% v/v.

*Thrips* potency of each compound was evaluated by using a floral-immersion technique. All petals of individual, intact orchid flowers were dipped into treatment solution and allowed to dry in Petri dishes. Treated petals were placed into individual re-sealable plastic along with about 20 adult *thrips*. All test arenas were held under continuous light and a temperature of about 28° C. for duration of the assay. After 3 days, the numbers of live *thrips* were counted on each petal. The percent mortality was recorded 72 hours after treatment.

In this test, I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-50, I-51, I-52, I-53, I-54, I-56, I-57 at 300 ppm showed at least 75% mortality in comparison with untreated controls.

B.8 Rice Green Leafhopper (*Nephotettix virescens*)

Rice seedlings were cleaned and washed 24 hours before spraying. The active compounds were formulated in 1:1 acetone:water (vol:vol), and 0.01% vol/vol surfactant (Kinetic HV) was added. Potted rice seedlings were sprayed with 5-6 ml test solution, air dried, covered with Mylar cages cages and inoculated with 10 adults. Treated rice plants were kept at about 28-29° C. and relative humidity of about 50-60%. Percent mortality was recorded after 72 hours.

In this test, I-1, I-2, I-4, I-6, I-7, I-8, I-9, I-10, I-11, I-12, I-14, I-15, I-16, I-17, I-18, I-19, I-20, I-21, I-22, I-23, I-24, I-28, I-30, I-31, I-33, I-34, I-36, I-37, I-38, I-39, I-52 at 300 ppm showed at least 75% mortality in comparison with untreated controls.

B.9 Red Spider Mite (*Tetranychus kanzawai*)

The active compound was dissolved at the desired concentration in a mixture of 1:1 (vol:vol) distilled water: acetone. Add surfactant (Kinetic HV) was added at a rate of 0.01% (vol/vol).The test solution was prepared at the day of use.

Potted cowpea beans of 4-5 days of age were cleaned with tap water and sprayed with 1-2 ml of the test solution using air driven hand atomizer. The treated plants were allowed to air dry and afterwards inoculated with 30 or more mites by clipping a cassava leaf section from rearing population. Treated plants were placed inside a holding room at about 25-27° C. and about 50-60% relative humidity. Percent mortality was assessed 72 hours after treatment.

In this test, I-7, I-9, I-11, I-14, I-15, I-16, I-17, I-18, I-19, I-20, I-21, I-22, I-23, I-28, I-29, I-34, I-54 at 300 ppm showed at least 75% mortality in comparison with untreated controls.

B.10 Southern Armyworm (*Spodoptera eridania*)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Lima bean plants (variety Sieva) were grown 2 plants to a pot and selected for treatment at the 1$^{st}$ true leaf stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. About 10 to 11 armyworm larvae were placed into the bag and the bags zipped closed. Test plants were maintained in a growth room at about 250C and about 20-40% relative humidity for 4 days, avoiding direct exposure to fluorescent light (24 hour photoperiod) to prevent trapping of heat inside the bags. Mortality and reduced feeding were assessed 4 days after treatment, compared to untreated control plants.

In this test, I-6, I-7, I-9, I-10, I-11, I-15, I-17, I-18, I-20, I-21, I-33, I-34, I-37, I-38, I-39, I-42, I-43, I-47, I-48 at 10 ppm showed at least 75% mortality in comparison with untreated controls.

B.11 Green Soldier Stink Bug (*Nezara viridula*)

The active compound was dissolved at the desired concentration in a mixture of 1:1 (vol:vol) distilled water: acetone. Surfactant (Kinetic HV) was added at a rate of 0.01% (vol/vol).The test solution was prepared at the day of use.

Soybean pods were placed in glass Petri dishes lined with moist filter paper and inoculated with ten late 3rd instar *N. viridula*. Using a hand atomizer, approximately 2 ml solution is sprayed into each Petri dish. Assay arenas were kept at about 25° C. Percent mortality was recorded after 5 days.

In this test, I-1, I-2, I-3, I-4, I-6, I-7, I-8, I-9, I-10, I-11, I-13, I-14, I-15, I-16, I-17, I-18, I-19, I-20, I-21, I-22, I-23, I-28, I-29, I-33, I-34 at 300 ppm showed at least 75% mortality in comparison with untreated controls.

B.12 Neotropical Brown Stink Bug (*Euschistus heros*)

The active compound was dissolved at the desired concentration in a mixture of 1:1 (vol:vol) distilled water: acetone. Surfactant (Kinetic HV) was added at a rate of 0.01% (vol/vol).The test solution was prepared at the day of use.

Soybean pods were placed in microwavable plastic cups and inoculated with ten adult stage *E. heros*. Using a hand atomizer, approximately 1 ml solution is sprayed into each cup, insects and food present. A water source was provided (cotton wick with water). Each treatment was replicated 2-fold. Assay arenas were kept at about 25° C. Percent mortality was recorded after 5 days.

In this test, I-1, I-2, I-6, I-7, I-9, I-10, I-11, I-15, I-17, I-18, I-20, I-23 at 100 ppm showed at least 75% mortality in comparison with untreated controls.

B.13 Brown Marmorated Stink Bug (*Halyomorpha halys*)

The active compound was dissolved at the desired concentration in a mixture of 1:1 (vol:vol) distilled water: acetone. Surfactant (Kinetic HV) was added at a rate of 0.01% (vol/vol).The test solution was prepared at the day of use.

Row peanuts and soybean seeds were placed into microwavable plastic cups and inoculated with five adult stage *H. halys*. Using a hand atomizer, approximately 1 ml solution is sprayed into each cup, insects and food present. A water source was provided (cotton wick with water). Each treatment is replicated 4-fold. Assay arenas are kept at about 25° C. Percent mortality was recorded after 5 days.

In this test I-6, I-7, I-8, I-9, I-15, I-17, I-18, I-20, I-21, I-34, I-37 at 100 ppm showed at least 75% mortality in comparison with untreated controls.

We claim:

1. A compound of formula (Ia.21)

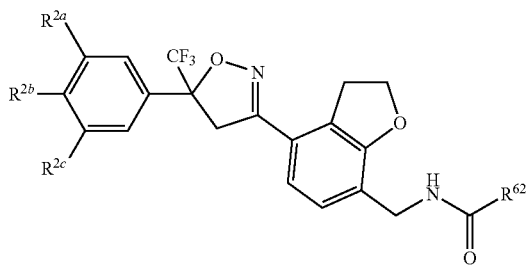

(Ia.21)

wherein

R$^{2a}$, R$^{2b}$ and R$^{2c}$, independently of each other, are selected from the group consisting of hydrogen, halogen, C$_1$-C$_2$-haloalkoxy, and C$_1$-C$_2$-haloalkyl; and R$^{62}$ is selected from the group consisting of hydrogen, C$_1$-C$_6$-alkyl, C$_1$-C$_6$-haloalkyl, C$_1$-C$_6$-alkyl substituted by one or two radicals R$^{82}$, C$_1$-C$_6$-haloalkyl which carries one radical R$^{82}$, C$_2$-C$_6$-alkenyl, C$_2$-C$_6$-haloalkenyl, C$_2$-C$_6$-alkynyl, C$_2$-C$_6$-haloalkynyl, C$_3$-C$_6$-cycloalkyl, C$_3$-C$_6$-cycloalkyl which carries a CN substituent, C$_3$-C$_6$-halocycloalkyl, —N(R$^{102a}$)R$^{102b}$, —C(=O)N(R$^{112a}$)R$^{112b}$, —CH=NOR$^{92}$, phenyl, phenyl which is substituted with 1, 2, 3, 4 or 5 substituents R$^{16}$; and a heterocyclic ring selected from the group consisting of rings of formulae E-1 to E-63:

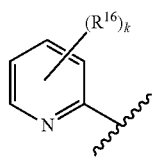 E-1

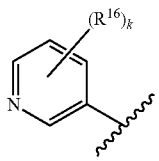 E-2

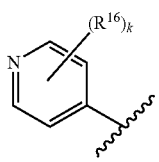 E-3

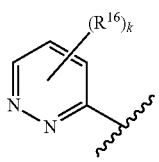 E-4

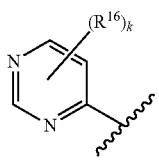 E-5

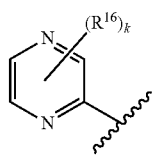 E-6

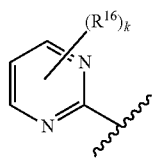 E-7

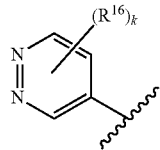 E-8

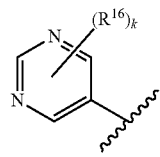 E-9

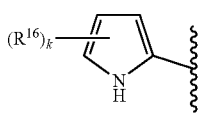 E-10

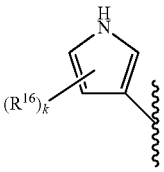 E-11

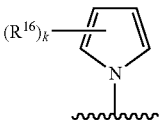 E-12

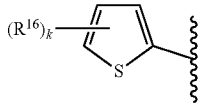 E-13

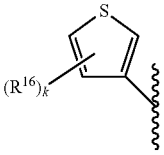 E-14

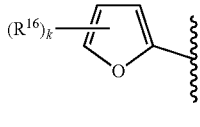 E-15

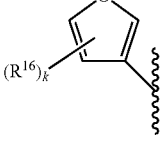 E-16

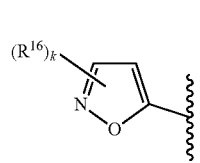 E-17

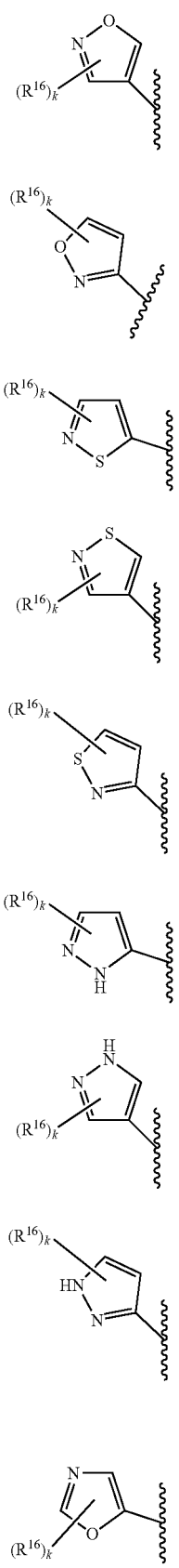
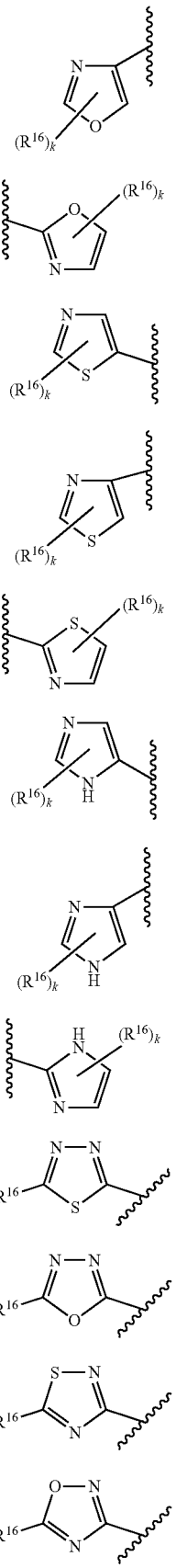

-continued
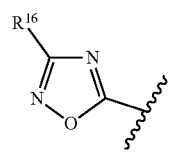 E-39
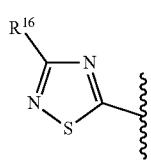 E-40
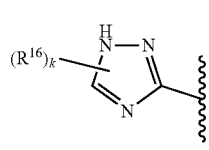 E-41
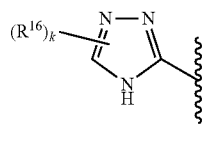 E-42
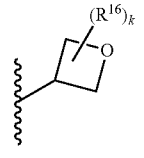 E-43
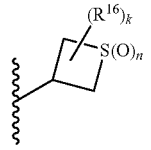 E-44
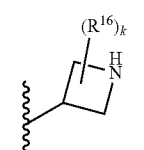 E-45
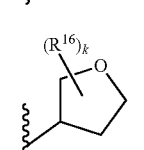 E-46
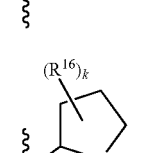 E-47
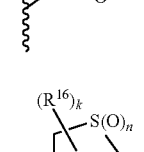 E-48
-continued
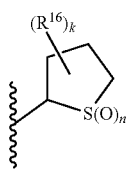 E-49
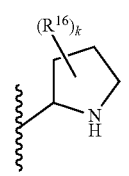 E-50
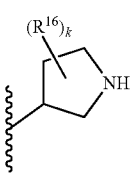 E-51
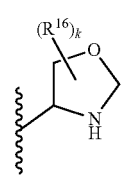 E-52
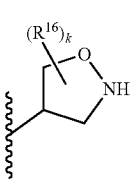 E-53
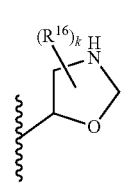 E-54
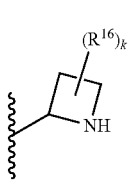 E-55
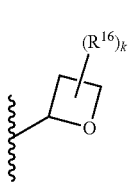 E-56
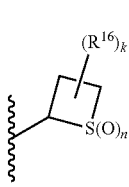 E-57

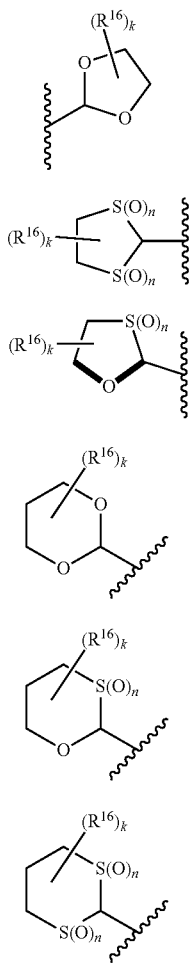

wherein rings E-1 to E-63
the zigzag line denotes the attachment point to the remainder of the molecule;

k is 0, 1, 2 or 3;

n is 0, 1 or 2; and $R^{16}$ is as defined below;

each $R^{82}$ is independently selected from the group consisting of OH, CN, $C_3$-$C_6$-cycloalkyl, $C_3$-$C_6$-cycloalkyl which carries a CN or $C_1$-haloalkyl substituent, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —C(=O)N($R^{102c}$)$R^{102d}$, phenyl, phenyl substituted with 1, 2, 3, 4 or 5 substituents $R^{16}$, and a heterocyclic ring selected from the group consisting of rings E-1 to E-63 as defined above;

$R^{92}$ is selected from the group consisting of hydrogen, $C_1$-$C_6$-alkyl, and $C_1$-$C_6$-haloalkyl;

$R^{102a}$, $R^{102c}$ and $R^{112a}$, independently of each other, are selected from the group consisting of hydrogen and $C_1$-$C_6$-alkyl;

$R^{102b}$ is selected from the group consisting of hydrogen, $C_1$-$C_6$-alkyl, $C_1$-$C_6$-haloalkyl, $CH_2$—CN, $C_2$-$C_4$-alkenyl, $C_2$-$C_4$-alkynyl, $C_3$-$C_6$-cycloalkyl, $C_3$-$C_6$-halocycloalkyl, $C_3$-$C_6$-cycloalkylmethyl, $C_3$-$C_6$-halocycloalkylmethyl, phenyl, phenyl substituted with 1, 2, 3, 4 or 5 substituents $R^{16}$; and a heterocyclic ring selected from the group consisting of rings of formulae E-1 to E-42 as defined above;

$R^{102d}$ and $R^{112b}$, independently of each other, are selected from the group consisting of hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-cycloalkyl which carries a CN substituent, $C_3$-$C_6$-halocycloalkyl, $C_3$-$C_6$-cycloalkylmethyl and $C_3$-$C_6$-halocycloalkylmethyl;

each $R^{16}$ is independently selected from the group consisting of halogen, cyano, nitro, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_3$-$C_6$-cycloalkyl-$C_1$-$C_4$-alkyl, $C_3$-$C_6$-halocycloalkyl-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)-aminocarbonyl; or two $R^{16}$ present on the same carbon atom of a saturated ring may form together =O or =S; or two $R^{16}$ present on the same S or SO ring member of a heterocyclic ring may together form a group =N($C_1$-$C_6$-alkyl), =NO($C_1$-$C_6$-alkyl), =NN(H)($C_1$-$C_6$-alkyl) or =NN($C_1$-$C_6$-alkyl)$_2$;

or an N-oxide, stereoisomer, or an agriculturally or veterinarily acceptable salt thereof.

2. The compound as claimed in claim 1, wherein $R^{2a}$, $R^{2b}$ and $R^{2c}$, independently of each other, are selected from the group consisting of hydrogen, halogen, $OCF_3$ and $CF_3$.

3. The compound as claimed in claim 2, wherein $R^{2a}$, $R^{2b}$ and $R^{2c}$, independently of each other, are selected from the group consisting of hydrogen and halogen.

4. The compound as claimed in claim 3, wherein $R^{2a}$, $R^{2b}$ and $R^{2c}$, independently of each other, are selected from the group consisting of hydrogen, F and Cl.

5. The compound as claimed in claim 4, wherein
$R^{2a}$ is Cl, $R^{2b}$ is H and $R^{2c}$ is Cl; or
$R^{2a}$ is Cl, $R^{2b}$ is F and $R^{2c}$ is H; or
$R^{2a}$ is Cl, $R^{2b}$ is F and $R^{2c}$ is Cl.

6. The compound as claimed in claim 1, wherein $R^{62}$ is selected from the group consisting of hydrogen, $C_1$-$C_6$-alkyl, $C_1$-$C_6$-haloalkyl, $C_1$-$C_6$-alkyl substituted by one or two radicals $R^{82}$, $C_1$-$C_6$-haloalkyl which carries one radical $R^{82}$, $C_3$-$C_6$-cycloalkyl, $C_3$-$C_6$-cycloalkyl which carries a CN substituent, and $C_3$-$C_6$-halocycloalkyl.

7. The compound as claimed in claim 6, wherein $R^{62}$ is selected from the group consisting of hydrogen, $C_1$-$C_6$-alkyl, $C_1$-$C_6$-haloalkyl, $C_1$-$C_6$-alkyl substituted by one radical $R^{82}$, $C_3$-$C_6$-cycloalkyl, and $C_3$-$C_6$-cycloalkyl which carries a CN substituent.

8. The compound as claimed in claim 1, wherein $R^{82}$ is selected from the group consisting of $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl and $C_1$-$C_6$-haloalkylsulfonyl.

9. The compound as claimed in claim 7, wherein $R^{62}$ is selected from the group consisting of methyl, ethyl, n-propyl, cyclopropyl, —$CH_2CF_3$, —$CH_2SCH_3$, —$CH_2SCH_2CH_3$, —$CH_2S(O)CH_3$, —$CH_2S(O)CH_2CH_3$, —$CH_2S(O)_2CH_3$, —$CH_2S(O)_2CH_2CH_3$, —$CH_2OCH_3$, and —$CH_2CH_2OCH_3$.

10. The compound as claimed in claim 1, wherein
$R^{2a}$ is Cl, $R^{2b}$ is H and $R^{2c}$ is Cl; and $R^{62}$ is selected from the group consisting of methyl, ethyl, n-propyl, cyclopropyl, —$CH_2CF_3$, —$CH_2SCH_3$, —$CH_2SCH_2CH_3$, —$CH_2S(O)CH_3$, —$CH_2S(O)CH_2CH_3$, —$CH_2S(O)_2CH_3$, —$CH_2S(O)_2CH_2CH_3$, —$CH_2OCH_3$, and —$CH_2CH_2OCH_3$; or $R^{2a}$ is Cl, $R^{2b}$ is F and $R^{2c}$ is H; and $R^{62}$ is selected from the group consisting of methyl, ethyl, n-propyl, cyclopropyl, —$CH_2CF_3$, —$CH_2SCH_3$, —$CH_2SCH_2CH_3$, —$CH_2S(O)CH_3$, —$CH_2S(O)CH_2CH_3$, —$CH_2S(O)_2CH_3$, —$CH_2S(O)_2CH_2CH_3$, —$CH_2OCH_3$, and —$CH_2CH_2OCH_3$; or $R^{2a}$ is Cl, $R^{2b}$ is F and $R^{2c}$ is Cl; and $R^{62}$ is selected from the group consisting of methyl, ethyl, n-propyl, cyclopropyl, —$CH_2CF_3$, —$CH_2SCH_3$, —$CH_2SCH_2CH_3$, —$CH_2S(O)CH_3$, —$CH_2S(O)CH_2CH_3$, —$CH_2S(O)_2CH_3$, —$CH_2S(O)_2CH_2CH_3$, —$CH_2OCH_3$, and —$CH_2CH_2OCH_3$.

11. The compound as claimed in claim 1, wherein
$R^{2a}$ is Cl, $R^{2b}$ is F and $R^{2c}$ is Cl; and $R^{62}$ is —$CH_2CH_2CH_3$; or
$R^{2a}$ is Cl, $R^{2b}$ is F and $R^{2c}$ is Cl; and $R^{62}$ is —$CH_2CH_3$; or
$R^{2a}$ is Cl, $R^{2b}$ is F and $R^{2c}$ is Cl; and $R^{62}$ is —$CH_3$; or
$R^{2a}$ is Cl, $R^{2b}$ is F and $R^{2c}$ is Cl; and $R^{62}$ is —$CH_2S(O)_2CH_2CH_3$; or
$R^{2a}$ is Cl, $R^{2b}$ is F and $R^{2c}$ is Cl; and $R^{62}$ is —$CH_2S(O)_2CH_3$; or
$R^{2a}$ is Cl, $R^{2b}$ is F and $R^{2c}$ is Cl; and $R^{62}$ is cyclopropyl.

12. The compound as claimed in claim 1, wherein
$R^{2a}$ is $C_1$, $R^{2b}$ is H and $R^{2c}$ is Cl; and $R^{62}$ is —$CH_2CH_2CH_3$; or
$R^{2a}$ is Cl, $R^{2b}$ is H and $R^{2c}$ is Cl; and $R^{62}$ is —$CH_2CH_3$; or
$R^{2a}$ is $C_1$, $R^{2b}$ is H and $R^{2c}$ is Cl; and $R^{62}$ is —$CH_3$; or
$R^{2a}$ is Cl, $R^{2b}$ is H and $R^{2c}$ is Cl; and $R^{62}$ is —$CH_2S(O)_2CH_2CH_3$; or
$R^{2a}$ is Cl, $R^{2b}$ is H and $R^{2c}$ is Cl; and $R^{62}$ is —$CH_2S(O)_2CH_3$; or
$R^{2a}$ is Cl, $R^{2b}$ is H and $R^{2c}$ is Cl; and $R^{62}$ is cyclopropyl.

13. An agricultural or veterinary composition comprising at least one compound of the formula Ia.21 as defined in claim 1, a stereoisomer thereof and/or at least one agriculturally or veterinarily acceptable salt thereof, and at least one inert liquid and/or solid agriculturally or veterinarily acceptable carrier.

14. The agricultural composition according to claim 13, further a surfactant.

15. The agricultural or veterinary composition according to claim 13, comprising additionally a further active ingredient.

16. A method for controlling invertebrate pests, which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials, soils, surfaces or spaces to be protected from pest attack or infestation with a pesticidally effective amount of a compound of formula Ia.21 as defined in claim 1, a stereoisomer thereof and/or at least one agriculturally acceptable salt thereof.

17. A method for protecting plant propagation material and/or the plants which grow therefrom from attack or infestation by invertebrate pests, which method comprises treating the plant propagation material with a pesticidally effective amount of at least one compound of the formula Ia.21 as defined in claim 1, a stereoisomer thereof and/or at least one agriculturally acceptable salt thereof.

18. A method for treating or protecting an animal from infestation or infection by invertebrate pests, which method comprises bringing the animal in contact with a pesticidally effective amount of a compound of the formula Ia.21 as defined in claim 1, a stereoisomer thereof and/or at least one veterinarily acceptable salt thereof.

19. A seed treated with at least one compound of the formula Ia.21 as defined in claim 1, a stereoisomer thereof and/or at least one agriculturally acceptable salt thereof, in an amount of from 0.01 g to 10 kg per 100 kg of seed.

* * * * *